US010507183B2

(12) United States Patent
Guild et al.

(10) Patent No.: US 10,507,183 B2
(45) Date of Patent: Dec. 17, 2019

(54) CLEAVABLE LIPIDS

(71) Applicant: Translate Bio, Inc., Lexington, MA (US)

(72) Inventors: Braydon Charles Guild, Concord, MA (US); Michael Heartlein, Boxborough, MA (US); Frank DeRosa, Chelmsford, MA (US); Jerry Chi Zhang, Lexington, MA (US)

(73) Assignee: Translate Bio, Inc., Lexington, MA (US)

( * ) Notice: Subject to any disclaimer, the term of this patent is extended or adjusted under 35 U.S.C. 154(b) by 0 days.

(21) Appl. No.: 15/887,693

(22) Filed: Feb. 2, 2018

(65) Prior Publication Data

US 2018/0169020 A1 Jun. 21, 2018

Related U.S. Application Data

(63) Continuation of application No. 15/651,832, filed on Jul. 17, 2017, which is a continuation of application No. 14/124,615, filed as application No. PCT/US2012/041663 on Jun. 8, 2012, now Pat. No. 9,717,690.

(60) Provisional application No. 61/494,745, filed on Jun. 8, 2011, provisional application No. 61/494,882, filed on Jun. 8, 2011.

(51) Int. Cl.
| | |
|---|---|
| *A61K 9/14* | (2006.01) |
| *A61K 9/19* | (2006.01) |
| *C07D 233/64* | (2006.01) |
| *A61K 9/127* | (2006.01) |
| *C07C 323/25* | (2006.01) |
| *C07C 323/44* | (2006.01) |
| *C12N 15/88* | (2006.01) |
| *A61K 38/45* | (2006.01) |
| *A61K 38/46* | (2006.01) |
| *A61K 38/47* | (2006.01) |
| *A61K 38/50* | (2006.01) |
| *A61K 31/7088* | (2006.01) |
| *C07C 323/27* | (2006.01) |
| *C07J 41/00* | (2006.01) |
| *C07J 43/00* | (2006.01) |
| *A61K 9/51* | (2006.01) |

(52) U.S. Cl.
CPC ............ *A61K 9/19* (2013.01); *A61K 9/1271* (2013.01); *A61K 9/1272* (2013.01); *A61K 31/7088* (2013.01); *A61K 38/45* (2013.01); *A61K 38/465* (2013.01); *A61K 38/47* (2013.01); *A61K 38/50* (2013.01); *C07C 323/25* (2013.01); *C07C 323/27* (2013.01); *C07C 323/44* (2013.01); *C07D 233/64* (2013.01); *C07J 41/0055* (2013.01); *C07J 43/003* (2013.01); *C12N 15/88* (2013.01); *A61K 9/5123* (2013.01); *C12Y 201/03003* (2013.01); *C12Y 203/01* (2013.01); *C12Y 207/08015* (2013.01); *C12Y 301/06* (2013.01); *C12Y 302/01022* (2013.01); *C12Y 302/01035* (2013.01); *C12Y 302/01046* (2013.01); *C12Y 302/01076* (2013.01); *C12Y 305/03001* (2013.01)

(58) Field of Classification Search
CPC .......... A61K 9/00; A61K 9/19; A61K 9/1271; A61K 9/5123; A61K 31/00; A61K 1/7088; A61K 38/00; A61K 38/47; A61K 38/465; A61K 38/50; A61K 38/45; A61K 9/91272; A61K 31/7088; C07J 43/003; C07J 41/0055; C07C 323/27; C07C 323/44; C07C 323/25; C12N 15/88; C07D 233/64; C12Y 302/01076; C12Y 301/06; C12Y 207/08015; C12Y 201/03003; C12Y 302/01035; C12Y 302/01046; C12Y 302/01022; C12Y 203/01; C12Y 305/03001
USPC ...... 424/1.11, 1.65, 1.73, 9.1, 9.2, 400, 489, 424/490; 977/773
See application file for complete search history.

(56) References Cited

U.S. PATENT DOCUMENTS

| | | | |
|---|---|---|---|
| 4,737,323 A | 4/1988 | Martin et al. | |
| 4,897,355 A | 1/1990 | Eppstein et al. | |
| 5,171,678 A | 12/1992 | Behr et al. | |
| 5,194,654 A | 3/1993 | Hostetler et al. | |
| 5,223,263 A | 6/1993 | Hostetler et al. | |

(Continued)

FOREIGN PATENT DOCUMENTS

| | | |
|---|---|---|
| DE | 3728917 A1 | 3/1989 |
| JP | 2008/520600 A2 | 6/2008 |

(Continued)

OTHER PUBLICATIONS

Anchordoquy, T.J. and Koe, G.S., Physical Stability of Nonviral Plamid-Based Therapeutics, J. Pharm. Sci., 89:289-296 (2000).

(Continued)

*Primary Examiner* — D. L. Jones
(74) *Attorney, Agent, or Firm* — Proskauer Rose LLP; Fangli Chen

(57) ABSTRACT

Disclosed herein are novel compounds, pharmaceutical compositions comprising such compounds and related methods of their use. The compounds described herein are useful, e.g., as liposomal delivery vehicles to facilitate the delivery of encapsulated polynucleotides to target cells and subsequent transfection of said target cells, and in certain embodiments are characterized as having one or more properties that afford such compounds advantages relative to other similarly classified lipids.

3 Claims, 2 Drawing Sheets

Specification includes a Sequence Listing.

(56) References Cited

U.S. PATENT DOCUMENTS

| | | |
|---|---|---|
| 5,334,761 A | 8/1994 | Gebeyehu et al. |
| 5,744,335 A | 4/1998 | Wolff et al. |
| 5,885,613 A | 3/1999 | Holland et al. |
| 5,948,441 A | 9/1999 | Lenk et al. |
| 5,965,434 A | 10/1999 | Wolff et al. |
| 6,153,434 A | 11/2000 | Hughes et al. |
| 6,214,804 B1 | 4/2001 | Feigner et al. |
| 6,379,698 B1 | 4/2002 | Leamon |
| 7,005,140 B2 | 2/2006 | Zhang |
| 8,450,298 B2 | 5/2013 | Anderson et al. |
| 8,853,377 B2 | 10/2014 | DeRosa et al. |
| 8,936,942 B2 | 1/2015 | Heyes et al. |
| 8,969,353 B2 | 3/2015 | Anderson et al. |
| 8,999,351 B2 | 4/2015 | Manoharan et al. |
| 8,999,950 B2 | 4/2015 | MacLachlan et al. |
| 9,018,187 B2 | 4/2015 | Heyes et al. |
| 9,061,021 B2 | 6/2015 | DeRosa et al. |
| 9,074,208 B2 | 7/2015 | MacLachlan et al. |
| 9,181,321 B2 | 11/2015 | DeRosa et al. |
| 9,308,281 B2 | 4/2016 | DeRosa et al. |
| 9,512,073 B2 | 11/2016 | Alabi et al. |
| 9,522,176 B2 | 12/2016 | Dias et al. |
| 9,546,128 B2 | 1/2017 | DeRosa et al. |
| 9,556,110 B2 | 1/2017 | Anderson et al. |
| 9,597,413 B2 | 3/2017 | DeRosa et al. |
| 9,629,804 B2 | 4/2017 | Anderson et al. |
| 9,668,980 B2 | 6/2017 | DeRosa et al. |
| 9,713,626 B2 | 7/2017 | DeRosa et al. |
| 9,717,690 B2 * | 8/2017 | Guild .................... C07D 233/64 |
| 9,850,269 B2 | 12/2017 | Dias et al. |
| 9,877,919 B2 | 1/2018 | DeRosa et al. |
| 9,943,595 B2 | 4/2018 | DeRosa et al. |
| 9,956,271 B2 | 5/2018 | DeRosa et al. |
| 9,957,499 B2 | 5/2018 | Dias et al. |
| 9,970,047 B2 | 5/2018 | Heartlein et al. |
| 10,022,455 B2 | 7/2018 | DeRosa et al. |
| 10,052,284 B2 | 8/2018 | Heartlein et al. |
| 10,065,919 B2 | 9/2018 | DeRosa et al. |
| 10,086,013 B2 | 10/2018 | Dong et al. |
| 10,087,247 B2 | 10/2018 | Heartlein et al. |
| 10,130,649 B2 | 11/2018 | DeRosa et al. |
| 10,137,086 B2 | 11/2018 | DeRosa et al. |
| 10,137,087 B2 | 11/2018 | DeRosa et al. |
| 10,138,213 B2 | 11/2018 | DeRosa et al. |
| 10,143,758 B2 | 12/2018 | Guild et al. |
| 10,144,942 B2 | 12/2018 | Strack-Logue et al. |
| 10,155,785 B2 | 12/2018 | DeRosa et al. |
| 10,172,924 B2 | 1/2019 | DeRosa et al. |
| 10,208,295 B2 | 2/2019 | DeRosa et al. |
| 2003/0082154 A1 | 5/2003 | Leamon |
| 2003/0083272 A1 | 5/2003 | Wiederholt et al. |
| 2009/0270481 A1 | 10/2009 | MacLachlan et al. |
| 2010/0158869 A1 | 6/2010 | Kaemmerer |
| 2011/0038941 A1 * | 2/2011 | Lee ........................ C12N 15/88 424/498 |
| 2011/0092739 A1 | 4/2011 | Chen et al. |
| 2011/0244026 A1 | 10/2011 | DeRosa et al. |
| 2013/0195967 A1 | 8/2013 | DeRosa et al. |
| 2014/0206753 A1 | 7/2014 | DeRosa et al. |
| 2014/0288160 A1 | 9/2014 | Guild et al. |
| 2014/0294940 A1 | 10/2014 | DeRosa et al. |
| 2015/0005372 A1 | 1/2015 | Hoge et al. |
| 2015/0017211 A1 | 1/2015 | de Fougerolles et al. |
| 2015/0044277 A1 | 2/2015 | Bancel et al. |
| 2015/0050354 A1 | 2/2015 | Bouchon et al. |
| 2015/0051268 A1 | 2/2015 | Bancel et al. |
| 2015/0064235 A1 | 3/2015 | Bancel et al. |
| 2015/0064236 A1 | 3/2015 | Bancel et al. |
| 2015/0064242 A1 | 3/2015 | Heyes et al. |
| 2015/0086613 A1 | 3/2015 | DeRosa et al. |
| 2015/0086614 A1 | 3/2015 | Bancel et al. |
| 2015/0110857 A1 | 4/2015 | DeRosa et al. |
| 2015/0110859 A1 | 4/2015 | DeRosa et al. |
| 2015/0111248 A1 | 4/2015 | Bancel et al. |
| 2015/0157565 A1 | 6/2015 | DeRosa et al. |
| 2015/0265708 A1 | 9/2015 | Manoharan et al. |
| 2015/0267192 A1 | 9/2015 | DeRosa et al. |
| 2015/0366997 A1 | 12/2015 | DeRosa et al. |
| 2015/0376144 A1 | 12/2015 | DeRosa et al. |
| 2016/0002705 A1 | 1/2016 | DeRosa et al. |
| 2016/0031928 A1 | 2/2016 | DeRosa et al. |
| 2016/0031981 A1 | 2/2016 | DeRosa et al. |
| 2016/0032356 A1 | 2/2016 | DeRosa et al. |
| 2016/0122727 A1 | 5/2016 | DeRosa et al. |
| 2016/0151409 A1 | 6/2016 | DeRosa et al. |
| 2016/0184458 A1 | 6/2016 | Heartlein et al. |
| 2016/0287725 A1 | 10/2016 | DeRosa et al. |
| 2016/0324940 A1 | 11/2016 | DeRosa et al. |
| 2017/0073648 A1 | 3/2017 | DeRosa et al. |
| 2017/0143848 A1 | 5/2017 | Calias et al. |
| 2017/0159093 A1 | 6/2017 | DeRosa et al. |
| 2017/0165290 A1 | 6/2017 | Alabi et al. |
| 2017/0239371 A1 | 8/2017 | DeRosa et al. |
| 2017/0240501 A1 | 8/2017 | DeRosa et al. |
| 2017/0246319 A1 | 8/2017 | DeRosa et al. |
| 2017/0281542 A1 | 10/2017 | Anderson et al. |
| 2017/0314041 A1 | 11/2017 | Crawford et al. |
| 2017/0348244 A1 | 12/2017 | DeRosa et al. |
| 2018/0008543 A1 | 1/2018 | DeRosa et al. |
| 2018/0008680 A1 | 1/2018 | DeRosa et al. |
| 2018/0015116 A1 | 1/2018 | DeRosa et al. |
| 2018/0028445 A1 | 2/2018 | DeRosa et al. |
| 2018/0125989 A1 | 5/2018 | DeRosa et al. |
| 2018/0153822 A1 | 6/2018 | Karve et al. |
| 2018/0161451 A1 | 6/2018 | Fotin-Mleczek et al. |
| 2018/0236047 A1 | 8/2018 | Guild et al. |
| 2018/0237766 A1 | 8/2018 | Heartlein et al. |
| 2018/0251754 A1 | 9/2018 | DeRosa et al. |
| 2018/0251755 A1 | 9/2018 | DeRosa et al. |
| 2018/0256741 A1 | 9/2018 | Dias et al. |
| 2018/0258423 A1 | 9/2018 | Dias et al. |
| 2018/0263918 A1 | 9/2018 | DeRosa et al. |
| 2018/0272002 A1 | 9/2018 | DeRosa et al. |
| 2018/0272003 A1 | 9/2018 | DeRosa et al. |
| 2018/0272004 A1 | 9/2018 | DeRosa et al. |
| 2018/0272005 A1 | 9/2018 | DeRosa et al. |
| 2018/0291425 A1 | 10/2018 | Heartlein et al. |
| 2018/0333457 A1 | 11/2018 | Heartlein et al. |
| 2018/0353616 A1 | 12/2018 | Guild et al. |
| 2018/0360961 A1 | 12/2018 | DeRosa et al. |
| 2018/0369144 A1 | 12/2018 | Heartlein et al. |
| 2018/0369413 A1 | 12/2018 | Heartlein et al. |

FOREIGN PATENT DOCUMENTS

| | | |
|---|---|---|
| WO | WO1995/04523 | 2/1995 |
| WO | 1998/51278 A2 | 11/1998 |
| WO | 1999045966 A1 † | 9/1999 |
| WO | WO-1999/045966 A1 | 9/1999 |
| WO | 2000/064484 A2 | 11/2000 |
| WO | 2001/05375 A1 | 1/2001 |
| WO | 2002/085434 A1 | 10/2002 |
| WO | 2004/033620 A2 | 4/2004 |
| WO | 2005/121348 A1 | 12/2005 |
| WO | 2007/031091 A2 | 3/2007 |
| WO | 2009026328 A2 † | 2/2009 |
| WO | WO-2009/026328 A2 | 2/2009 |
| WO | WO-2009/142892 | 11/2009 |
| WO | WO-2010/019718 A2 | 2/2010 |
| WO | 2010/042877 A1 | 4/2010 |
| WO | 2010054401 A1 † | 5/2010 |
| WO | WO 2010/053572 | 5/2010 |
| WO | WO-2010/054401 A1 | 5/2010 |
| WO | 2011/003834 A1 | 1/2011 |
| WO | 2011/039144 A1 | 4/2011 |
| WO | 2011/068810 A1 | 6/2011 |
| WO | 2011/069528 A1 | 6/2011 |
| WO | 2011/069529 A1 | 6/2011 |
| WO | 2011/069586 A1 | 6/2011 |
| WO | WO 2011/068810 | 6/2011 |
| WO | WO 2011/071860 A2 | 6/2011 |
| WO | 2011/144358 A1 | 11/2011 |
| WO | WO 2012/075040 | 6/2012 |
| WO | 2012/170889 A1 | 12/2012 |

(56) References Cited

FOREIGN PATENT DOCUMENTS

| WO | 2012/170889 A2 | 12/2012 |
|---|---|---|
| WO | 2012/170899 A1 | 12/2012 |
| WO | 2012/170930 A9 | 12/2012 |
| WO | WO 2012/170930 | 12/2012 |
| WO | WO 2013/063468 | 5/2013 |
| WO | 2013/090186 A1 | 6/2013 |
| WO | 2013/143555 A1 | 10/2013 |
| WO | 2013/151669 A1 | 10/2013 |
| WO | WO 2013/149140 | 10/2013 |
| WO | WO 2013/149141 | 10/2013 |
| WO | 2013/174409 A1 | 11/2013 |
| WO | WO 2013/185067 | 12/2013 |
| WO | WO 2013/185069 | 12/2013 |
| WO | 2014/089486 A1 | 6/2014 |
| WO | 2014/152940 A1 | 9/2014 |
| WO | WO 2014/144196 | 9/2014 |
| WO | WO 2014/152513 | 9/2014 |
| WO | WO 2014/152659 | 9/2014 |
| WO | WO 2014/152673 | 9/2014 |
| WO | WO 2014/152774 | 9/2014 |
| WO | WO 2014/152966 | 9/2014 |
| WO | WO 2014/153052 | 9/2014 |
| WO | 2014/207231 A1 | 12/2014 |
| WO | WO 2014/201252 | 12/2014 |
| WO | 2015/006747 A2 | 1/2015 |
| WO | 2015/011633 A1 | 1/2015 |
| WO | 2015/023939 A1 | 2/2015 |
| WO | 2015/023941 A1 | 2/2015 |
| WO | 2015/023975 A1 | 2/2015 |
| WO | 2015/024664 A1 | 2/2015 |
| WO | 2015/024666 A1 | 2/2015 |
| WO | 2015/043613 A1 | 4/2015 |
| WO | WO 2015/061461 | 4/2015 |
| WO | WO 2015/061467 | 4/2015 |
| WO | WO 2015/061491 | 4/2015 |
| WO | WO 2015/061500 | 4/2015 |
| WO | 2015/128030 A2 | 9/2015 |
| WO | 2015/149944 A1 | 10/2015 |
| WO | WO 2015/148247 | 10/2015 |
| WO | WO 2015/164773 | 10/2015 |
| WO | WO 2015/184256 | 12/2015 |
| WO | WO 2015/200465 | 12/2015 |
| WO | WO 2016/004318 | 1/2016 |
| WO | WO 2016/090262 | 6/2016 |
| WO | WO 2016/149508 | 9/2016 |
| WO | 2016/165825 A1 | 10/2016 |
| WO | 2016/165831 A1 | 10/2016 |
| WO | 2016/180430 A1 | 11/2016 |
| WO | 2016/184577 A1 | 11/2016 |
| WO | WO 2017/066573 | 4/2017 |
| WO | WO 2017/177169 | 10/2017 |
| WO | 2017/218704 A1 | 12/2017 |
| WO | WO 2017/218524 | 12/2017 |

OTHER PUBLICATIONS

Barton et al., "A New Procedure for the Conversion of Thiois into Reactive Sulfenylating", J. Org. Chem., 56(23), 6697-702 (1991).
Behr, J-P. et al., Efficient gene transfer into mammalian primary endocrine cells with lipopolyamine-coated DNA, Proc. Natl. Acad. Sci., 86: 6982-6986 (1989).
Bloomfield, V.A., Quasi-elastic light scattering applications in biochemistry and biology, Ann. Rev. Biophys. Bioeng., 10: 421-450 (1981).
Budker, V. et al., Protein/Amphipathic Polyamine ComplexesEnable Highly Efficient Transfection withMinimalToxicity, BioTechniques, 23: 139-147 (1997).
Caplen, N.J. et al., In vitro liposome-mediated DNA transfection of epithelial cell lines using the cationic liposome DC-Chol/DOPE, Gene Ther., 2(9): 603-613 (1995).
Chau, Y. et al., Investigation of targeting mechanism of new dextran-peptide-methotrexate conjugates using biodistribution study in matrix-metalloproteinase-overexpressing tumor xenograft model, J. Pharm. Sci., 95(3): 542-551 (2006).
Christensen, U.B. et al., Intercalating nucleic acids containing insertions of 1-O-(1-pyrenylmethyl)glycerol: stabilisation of dsDNA and discrimination of DNA over RNA, Nucl. Acids. Res., 30(22): 4918-4925 (2002).
Denardo, S.J. et al., Enhanced Therapeutic Index of Radioimmunotherapy (RIT) in Prostate Cancer Patients Comparison of Radiation Dosimetry for 1,4,7,10-Tetraazacyclododecane-N,N',N'',N'''-Tetraacetic Acid (DOTA)-Peptide versus 2IT-DOTA Monoclonal Antibody Linkage for RIT1, Clin. Cancer Res., 9: 3665s (2003).
Fechter, P. et al., Recognition of mRNA cap structures by viral and cellular proteins, J. Gen. Virology, 86(5): 1239-1249 (2005).
Felgner, P.F. et al., Lipofection: A highly efficient, lipid-mediated DNA-transfection procedure, Proc. Natl. Acad. Sci., 84: 7413-7417 (1987).
Gao, X. and Huang, L., A novel cationic liposome reagent for efficient transfection of mammalian cells, Biochem. Biophys. Res. Comm., 179(1): 280-285 (1991).
Guttman, M. et al., Chromatin signature reveals over a thousand highly conserved large non-coding RNAs in mammals, Nature, 458: 223-227 (2009).
Heidenreich, O. et al., High activity and stability of hammerhead ribozymes containing 2'-modified pyrimidine nucleosides and phosphorothioates, J. Biol. Chem., 269(3): 2131-2138 (1994).
Heyes, J., et al., Cationic lipid saturation influences intracellular delivery of encapsulated nucleic acids, J. Controlled Release, 107: 276-287 (2005).
Huang, Z. et al, Thiocholesterol-based lipids for; ordered assembly of bioresponsive gene carriers. Molecular Therapy, 11(3):409-17 (2005).
Kariko, K. et al., Incorporation of Pseudouridine Into mRNA Yields Superior Nonimmunogenic Vector With Increased Translational Capacity and Biological Stability, Molecular Therapy, 16(11): 1833-1840 (2008).
Klibanov, A.L. et al., Amphipathic polyethyleneglycols effectively prolong the circulation time of liposomes, FEBS Letters, 268(1): 235-237 (1990).
Kozak M., An analysis of 5'-noncoding sequences from 699 vertebrate messenger RNAs, Nucleic Acids Res 15 (20): 8125-48 (1987).
Lasic, D.D. et al., Gelation of liposome interior. A novel method for drug encapsulation., FEBS Lett., 312(2-3): 255-258, (1992).
Li, S. and Huang, L., In vivo gene transfer via intravenous administration of cationic lipid-protamine-DNA (LPD) complexes, Gene Ther., 4(9): 891-900 (1997).
Li, W. et al., Lipid-based nanoparticles for nucleic acid delivery, Pharm Res., 24(3): 438-449 (2007).
Manjappa et al., Antibody derivatization and conjugation strategies: Application in preparation of stealth immunoliposome to target chemotherapeutics to tumor, Journal of Controlled Release, 150:2-22. (2011).
Mevel et al., "DODAG; a versatile new cationic lipid that mediates efficient delivery of pDNA and siRNA", Journal of Controlled Release, 143: 222-232 (2010).
Monia, B.P. et al., Evaluation of 2'-Modified Oligonucleotides Containing 2'-Deoxy Gaps as Antisense Inhibitors of Gene Expression, J. Biol. Chem., 268: 14514-15222 (1993).
Morrissey, D V. et al., Potent and persistence in vivo anti-HBV activity of chemically modified siRNAs, Nature Biotechnology, 23(8): 1003-1007 (2005).
Ng, J.H. et al., LincRNAs join the pluripotency alliance, Nature Genetics 42(12): 1035-1036 (2010).
Nori, A. et al., Tat-conjugated synthetic macromolecules facilitate cytoplasmic drug delivery to human ovarian carcinoma cells, Bioconj. Chern., 14(1): 44-50 (2003).
Pons, M. et al., Liposomes obtained by the ethanol injection method, Int. J. Pham., 95: 51-56. (1993).
Semple, S.C. et al, Rational design of cationic lipids for siRNA delivery, Nature Biotechnology, 28(2): 172-176 (2010).
Semple, S.C., et al., Efficient encapsulation of antisense oligonucleotides in lipid vesicles using iionizable aminolipids: formation of navel small multilamellar vesicle structures, Biochimica et Biophysica Acta, 1510: 152-166 (2001).
Sherwood, R.F. Advanced drug delivery reviews: enzyme prodrug therapy, Adv. Drug Del. Rev., 22: 269-288 (1996).

(56) References Cited

OTHER PUBLICATIONS

Stern, L. et al., A novel antitumor prodrug platform designed to be cleaved by the endoprotease legumain, Bioconj. Chem., 20: 500-510 (2009).
Tang, F. and Hughes, J, Introduction of a disulfide bond into a cationic lipid enhances transgene expression of plasmid DNA. Biochemical Biophysical Research Communications, 242(1):141-5 (1998).
Toki, B.E. et al., Protease-mediated fragmentation of p-amidobenzyl ethers: a new strategy for the activation of anticancer prodrugs, J. Org. Chem., 67(6): 1866-1872 (2002).
Veronese, F.M. et al., PEG-doxorubicin conjugates: influence of polymer structure on drug release, in vitro cytotoxicity, biodistribution, and antitumor activity, Bioconj. Chem, 16(4): 775-784 (2005).
Wetzer, B. et al., Reducible cationic lipids for gene transfer, Biochemical Journal, 356:747-756 (2001).
Yokoe, H. and Meyer, T. et al., Spatial dynamics of GFP-tagged proteins investigated by local fluorescence enhancement, Nature Biotechnology, 14: 1252-1256 (1996).
Yoneda et al., A cell-penetrating peptidic GRP78 ligand for tumor cell-specific prodrug therapy, Bioorg. Med. Chem. Lett., 18(5): 1632-1636 (2008).
International Search Report for PCT/US2012/041663, 4 pages (dated Oct. 8, 2012).
Written Opinion for PCT/US2012/041663, 7 pages (dated Oct. 8, 2012).
International Search Report for PCT/US2013/034604, 4 pages (dated Jun. 17, 2013).
Written Opinion for PCT/US2013/034604, 9 pages (dated Jun. 17, 2013).
U.S. Appl. No. 12/613,968, filed Nov. 6, 2009, Daniel Griffith Anderson et al.
U.S. Appl. No. 15/809,605, filed Nov. 10, 2017, Frank DeRosa et al.
U.S. Appl. No. 15/809,680, filed Nov. 10, 2017, Zarna Bhavsar et al.
U.S. Appl. No. 15/831,252, filed Dec. 4, 2017, Frank DeRosa et al.
U.S. Appl. No. 15/878,131, filed Jan. 23, 2018, Frank DeRosa et al.
U.S. Appl. No. 15/878,137, filed Jan. 23, 2018, Frank DeRosa et al.
U.S. Appl. No. 15/887,693, filed Feb. 2, 2018, Frank DeRosa et al.
U.S. Appl. No. 15/906,864, filed Feb. 27, 2018, Jonathan Abysalh et al.
U.S. Appl. No. 15/907,086, filed Feb. 27, 2018, Jonathan Abysalh et al.
U.S. Appl. No. 15/907,131, filed Feb. 27, 2018, Jonathan Abysalh et al.
U.S. Appl. No. 15/907,163, filed Feb. 27, 2018, Jonathan Abysalh et al.
U.S. Appl. No. 15/913,783, filed Mar. 6, 2018, Frank DeRosa et al.
U.S. Appl. No. 15/936,289, filed Mar. 26, 2018, Frank DeRosa et al.
U.S. Appl. No. 15/936,293, filed Mar. 26, 2018, Frank DeRosa et al.
U.S. Appl. No. 15/937,359, filed Mar. 27, 2018, Frank DeRosa et al.
Wu et al., "Development of a Novel Method for Formulating Stable siRNA-loaded Lipid Particles for In vivo Use" (Pharm Res. 2009; 26(3):512-522).
Yadava et al., "Effect of Lyophilization and Freeze-thawing on the Stability of siRNA-liposome Complexes" (AAPS PharmSciTech. 2008; 9(2):335-41).
U.S. Appl. No. 15/977,756, filed May 11, 2018, Heartlein et al.
U.S. Appl. No. 15/983,635, filed May 18, 2018, Heartlein et al.
U.S. Appl. No. 16/100,853, filed Aug. 10, 2018, DeRosa et al.
U.S. Appl. No. 16/126,897, filed Sep. 10, 2018, Dong et al.
U.S. Appl. No. 16/129,412, filed Sep. 12, 2018, Heartlein et al.
U.S. Appl. No. 16/157,050, filed Oct. 10, 2018, DeRosa et al.
U.S. Appl. No. 16/165,372, filed Oct. 19, 2018, Strack-Logue et al.
U.S. Appl. No. 16/178,142, filed Nov. 1, 2018, DeRosa et al.
U.S. Appl. No. 16/182,090, filed Nov. 6, 2018, DeRosa et al.
U.S. Appl. No. 16/191,017, filed Nov. 14, 2018, DeRosa et al.
U.S. Appl. No. 16/196,664, filed Nov. 20, 2018, DeRosa et al.
U.S. Appl. No. 16/228,596, filed Dec. 20, 2018, Askew et al.
U.S. Appl. No. 16/233,031, filed Dec. 26, 2018, Guild et al.
U.S. Appl. No. 16/245,828, filed Jan. 11, 2019, DeRosa et al.
U.S. Appl. No. 16/258,191, filed Jan. 25, 2019, Heartlein et al.
Chen et al., "An overview of liposome lyophilization and its future potential", Journal of Controlled Release, 142:299-311 (2010).
Danaei et al., Impact of Particle Size and Polydispersity Index on the Clinical Applications of Lipidic Nanocarrier Systems, Pharmaceutics, 10(57): 1-17 (2018).
Eberhardt et al., "Modulation of mRNA stability as a novel therapeutic approach", Pharmacology and Therapeutics, 114(1): 56-73 (2007).
Ewert et al., "Cationic lipid-DNA complexes for non-viral gene therapy: relating supramolecular structures to cellular pathways", Expert Opin Biol Ther., 5(1): 33-53 (2005).
Franks, "Freeze-drying of bioproducts: putting principles into practice", European Journal of Pharmaceutics and Biopharmaceutics, 45:221-229 (1998).
Gaumet et al., "Nanoparticles for drug delivery: the need for precision in reporting particle size parameters", Eur J Pharm Biopharm., 69(1):1-9 (2008).
Kasper et al., "The freezing step in lyophilization: Physico-chemical fundamentals, freezing methods and consequences on process performance and quality attributes of biopharmaceuticals", European Journal of Pharmaceutics and Biopharmaceutics, 78: 248-263 (2011).
Lechardeur et al., "Metabolic instability of plasmid DNA in the cytosol: a potential barrier to gene transfer", Gene Ther., 6: 482-497 (1999).
Melton et al., "Efficient in vitro synthesis of biologically active RNA and RNA hybridization probes from plasmids containing a bacteriophage SP6 promoter", Nucleic Acid Research, 12(18): 7035-7056 (1984).
Montana et al., "Employment of Cationic Solid-Lipid Nanoparticles as RNA Carriers", Bioconjugate Chemistry, 18(2): 302-308 (2007).
Mukai et al., "2-5A antisense telomerase RNA therapy for intracranial malignant gliomas", Cancer Res., 60(16): 4461-4467 (2000).
Robinson et al., "Lipid Nanoparticle-Delivered Chemically Modified mRNA Restores Chloride Secretion in Cystic Fibrosis", Molecular Therapy 26(8): 1-13 (2018).
Su et al., "In vitro and in vivo mRNA delivery using lipid-enveloped pH-responsive polymer nanoparticles", Molecular Pharmaceutics, 8(3): 774-787 (2011).
Tsui et al., "Stability of endogenous and added RNA in blood specimens, serum, and plasma", Clinical Chemistry 48(10): 1647-1653 (2002).
Tuschl et al., "Targeted mRNA degradation by double-stranded RNA in vitro", Genes & Development, 13: 3191-3197 (1999).
Nelson, D. L. et al., "Nucleotides and Nucleic Acids", Chapter 8, Lehninger Principles of Biochemistry, Fifth Edition, W. H. Freeman and Company, New York, (2008), pp. 271-302. (Exhibit A).
[No Author Cited], "Which is Bigger, mRNA or the protein it codes for?" [online] Aug. 15, 2019, [retrieved on Aug. 15, 2019], Retrieved from the Internet: <URL:http:/book.bionumbers.org/which-is-bigger-mrna-or-the-protein-it-codes-for/, 3 pages. (Exhibit B).
Montana et al., "Employment of cationic solid-lipid nanoparticles as RNA carriers," Bioconjugate Chem., 18:302-308, 2007.†

\* cited by examiner
† cited by third party

CLEAVABLE LIPIDS

CROSS-REFERENCE TO RELATED APPLICATIONS

The present application is a continuation of U.S. patent application Ser. No. 15/651,832 filed Jul. 17, 2017; which is a continuation of U.S. patent application Ser. No. 14/124,615, filed on Jun. 4, 2014, which issued as U.S. Pat. No. 9,717,690 on Aug. 1, 2017; which is the U.S. National Stage Entry claiming priority to International Application PCT/US2012/041663 filed on Jun. 8, 2012; which claims priority to U.S. Provisional Application No. 61/494,882 filed Jun. 8, 2011, and U.S. Provisional Application No. 61/494,745 filed Jun. 8, 2011, the disclosures of which are hereby incorporated by reference.

SEQUENCE LISTING

The instant application contains a Sequence Listing which has been submitted electronically in ASCII format and is hereby incorporated by reference in its entirety. Said ASCII copy, created on Jan. 23, 2018, is named "MRT-1053U53_Sequence Listing.txt" and is 7,914 bytes in size.

Liposomal delivery of nucleic acids has been employed for the site-specific delivery of encapsulated plasmid DNA, antisense oligonucleotides, short interfering RNA and microRNA-based therapies. However, the efficient delivery of nucleic acids to targeted cells and tissues, as well as the subsequent transfection of such targeted cells and tissues remains a technical challenge. Despite the availability of multiple liposomal-based systems and vehicles to facilitate the delivery of therapeutic agents to target cells and tissues, many problems still exist both in in vivo and in vitro applications. For example, a significant drawback of liposomal delivery systems relates to the construction of liposomes that have sufficient cell culture or in vivo stability to reach desired target cells and/or intracellular compartments, and the ability of such liposomal delivery systems to efficiently release their encapsulated materials to such target cells. Furthermore, many of the cationic lipids that are employed to construct such liposomal-based vehicles are generally toxic to the targeted cells, and accordingly may be of limited use, particularly in quantities necessary to successfully deliver encapsulated materials to such target cells.

Despite the foregoing limitations, and as a results of their ability to protect and facilitate the delivery of encapsulated materials to one or more target cells, liposomal-based vehicles are considered an attractive carrier for therapeutic agents and remain subject to continued development efforts. While liposomal-based vehicles that comprise a cationic lipid component have shown promising results with regards to encapsulation, stability and site localization, there remains a great need for improvement of liposomal-based delivery systems. In particular, there remains a need for improved cationic and lipids which are capable of delivering macromolecules such as nucleic acids to a wide variety cell types and tissues with enhanced efficiency. There also remains a particular need for novel lipids that incorporate a multifunctional approach for delivering encapsulated nucleic acids and polynucleotides.

Thus, the invention provides novel compounds, pharmaceutical compositions comprising such compounds and related methods of their use. In some embodiments, the compounds described herein are useful as liposomal compositions or as components of liposomal compositions to facilitate the delivery to, and subsequent transfection of one or more target cells. In certain embodiments, the compositions disclosed herein are cationic and/or ionizable lipids. In some embodiments, the compounds described herein have been designed based on desired characteristics or properties, for example to enhance transfection efficiency or to promote specific biological outcomes. Furthermore, in certain embodiments the compounds described herein employ a multifunctional strategy to facilitate the delivery of encapsulated materials (e.g., one or more polynucleotides) to, and the subsequent transfection of one or more target cells. For example, in certain embodiments the compounds described herein are characterized as having one or more of fusogenic, endosomal or lysosomal disruption and/or releasable properties that afford such compounds advantages relative other similarly classified lipids.

The compounds disclosed herein generally comprise one or more cleavable (e.g., cleavable enzymatically or by reduction, oxidation or hydrolysis) functional groups to which are bound (e.g., covalently bound) two or more functional groups or moieties (e.g., a hydrophobic $R_1$ group and a hydrophilic $R_2$ group). For example, disclosed herein are compounds that comprise a cleavable disulfide (S—S) functional group. Also contemplated are compounds that comprise any functional groups that are capable of being cleaved, for example upon exposure to biological conditions, and that for the purposes hereof such groups may include, but are not limited to, esters and ethers. In certain embodiments, the two or more functional groups (e.g., a head-group and a tail-group) that comprise the compounds render such compounds amphiphilic. For example, in certain embodiments, at least one of the functional groups is a non-polar, lipophilic or hydrophobic tail-group (e.g., a naturally-occurring lipid such as cholesterol or a $C_6$-$C_{20}$ alkyl). In certain embodiments, at least one of the functional groups is a polar or hydrophilic head-group (e.g., imidazole).

In certain embodiments, the compounds described herein (e.g., HGT4001, HGT4002, HGT4003, HGT4004 and/or HGT4005) are cationic or ionizable lipids that may be used as a component of a liposomal composition to facilitate or enhance the delivery and release of encapsulated materials (e.g., one or more therapeutic agents) to one or more target cells (e.g., by permeating or fusing with the lipid membranes of such target cells). In certain embodiments, the one or more cleavable functional groups (e.g., a disulfide) that comprise such compounds allow, for example, a hydrophilic functional head-group to dissociate (e.g., upon exposure to oxidative, reducing or acidic conditions) from a lipophilic functional tail-group of the compound, thereby facilitating a phase transition in the lipid bilayer of the one or more target cells. For example, when a liposomal composition (e.g., a lipid nanoparticle) comprises one or more of the compounds disclosed herein, the phase transition in the lipid bilayer of the one or more target cells facilitates the delivery of the encapsulated materials (e.g., one or more therapeutic polynucleotides encapsulated in a lipid nanoparticle) into the one or more target cells. Similarly, enriching liposomal compositions with one or more of the compounds disclosed herein may improve the fusogenicity of such liposomal compositions, thereby enhancing the ability of such compounds to deliver materials (e.g., polynucleotides) encapsulated therein intracellularly.

In certain embodiments, the compounds have the structure of formula (I),

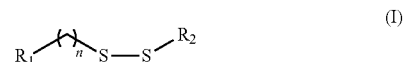

(I)

wherein $R_1$ is selected from the group consisting of imidazole, guanidinium, amino, imine, enamine, an optionally-substituted alkyl amino (e.g., an alkyl amino such as dimethylamino) and pyridyl; wherein $R_2$ is selected from the group consisting of formula II and formula III;

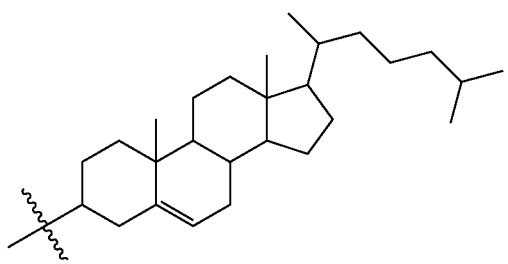

(II)

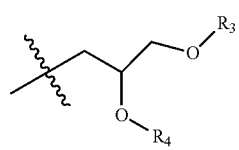

(III)

wherein $R_3$ and $R_4$ are each independently selected from the group consisting of an optionally substituted, variably saturated or unsaturated $C_6$-$C_{20}$ alkyl and an optionally substituted, variably saturated or unsaturated $C_6$-$C_{20}$ acyl; and wherein n is zero or any positive integer (e.g., one, two, three, four, five, six, seven, eight, nine, ten, eleven, twelve, thirteen, fourteen, fifteen, sixteen, seventeen, eighteen, nineteen, twenty or more). In certain embodiments, $R_3$ and $R_4$ are each an optionally substituted, polyunsaturated $C_{18}$ alkyl, while in other embodiments $R_3$ and $R_4$ are each an unsubstituted, polyunsaturated $C_{18}$ alkyl. In certain embodiments, one or more of $R_3$ and $R_4$ are (9Z,12Z)-octadeca-9,12-dien.

Also disclosed herein are pharmaceutical compositions that comprise the compound of formula I, wherein $R_1$ is selected from the group consisting of imidazole, guanidinium, amino, imine, enamine, an optionally-substituted alkyl amino (e.g., an alkyl amino such as dimethylamino) and pyridyl; wherein $R_2$ is formula II; and wherein n is zero or any positive integer. Further disclosed herein are pharmaceutical compositions comprising the compound of formula I, wherein $R_1$ is selected from the group consisting of imidazole, guanidinium, amino, imine, enamine, an optionally-substituted alkyl amino (e.g., an alkyl amino such as dimethylamino) and pyridyl; wherein $R_2$ is formula III; wherein $R_3$ and $R_4$ are each independently selected from the group consisting of an optionally substituted, variably saturated or unsaturated $C_6$-$C_{20}$ alkyl and an optionally substituted, variably saturated or unsaturated $C_6$-$C_{20}$ acyl; and wherein n is zero or any positive integer. In certain embodiments, $R_3$ and $R_4$ are each an optionally substituted, polyunsaturated $C_{18}$ alkyl, while in other embodiments $R_3$ and $R_4$ are each an unsubstituted, polyunsaturated $C_{18}$ alkyl (e.g., octadeca-9,12-dien).

In certain embodiments, the $R_1$ group or head-group is a polar or hydrophilic group (e.g., one or more of the imidazole, guanidinium and amino groups) and is bound to the $R_2$ lipid group by way of the disulfide (S—S) cleavable linker group, for example as depicted in formula I. Other contemplated cleavable linker groups may include compositions that comprise one or more disulfide (S—S) linker group bound (e.g., covalently bound) to, for example an alkyl group (e.g., $C_1$ to $C_{10}$ alkyl). In certain embodiments, the $R_1$ group is covalently bound to the cleavable linker group by way of a $C_1$-$C_{20}$ alkyl group (e.g., where n is one to twenty), or alternatively may be directly bound to the cleavable linker group (e.g., where n is zero). In certain embodiments, the disulfide linker group is cleavable in vitro and/or in vivo (e.g., enzymatically cleavable or cleavable upon exposure to acidic or reducing conditions).

In certain embodiments, the inventions relate to the compound 5-(((10,13-dimethyl-17-(6-methylheptan-2-yl)-2,3,4,7,8,9,10,11,12,13,14,15,16,17-tetradecahydro-1H-cyclopenta[a]phenanthren-3-yl)disulfanyl)methyl)-1H-imidazole, having the structure of formula IV (referred to herein as "HGT4001").

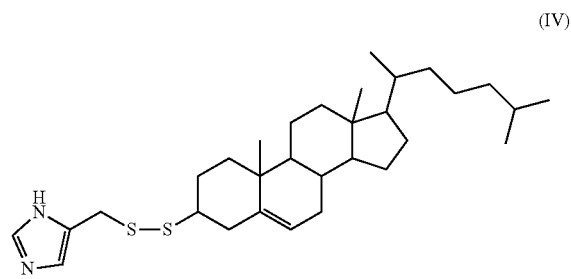 [SMILES: CC(C)CCCC(C)C1CCC2C3CC=C4CC(SSCc5cnc[nH]5)CCC4(C)C3CCC12C]

(IV)

In certain embodiments, the inventions relate to the compound -(2-(((3S,10R,13R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yl)disulfanyl) ethyl)guanidine, having the structure of formula V (referred to herein as "HGT4002").

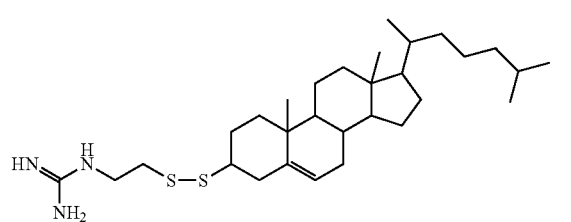

(V)

In certain embodiments, the inventions relate to the compound 2-((2,3-Bis((9Z,12Z)-octadeca-9,12-dien-1-yloxy)propyl)disulfanyl)-N,N-dimethylethanamine, having the structure of formula VI (referred to herein as "HGT4003").

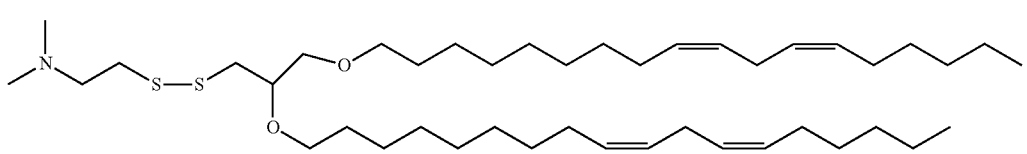

(VI)

In other embodiments, the inventions relate to the compound 5-(((2,3-bis((9Z,12Z)-octadeca-9,12-dien-1-yloxy)propyl)disulfanyl)methyl)-1H-imidazole having the structure of formula VII (referred to herein as "HGT4004").

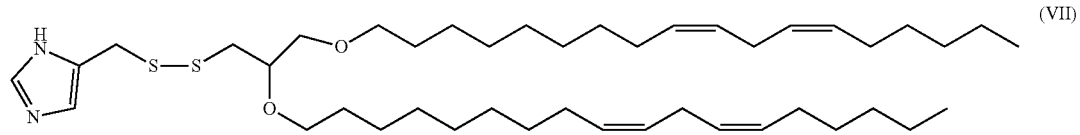 [SMILES: CCCCC/C=C\C/C=C\CCCCCCCCOCC(CSSCc1cnc[nH]1)OCCCCCCCC/C=C\C/C=C\CCCCC]

(VII)

In still other embodiments, the inventions relate to the compound 1-(((2,3-bis((9Z,12Z)-octadeca-9,12-dien-1-yloxy)propyl)disulfanyl)methyl)guanidine having the structure of Formula VIII (referred to herein as "HGT4005").

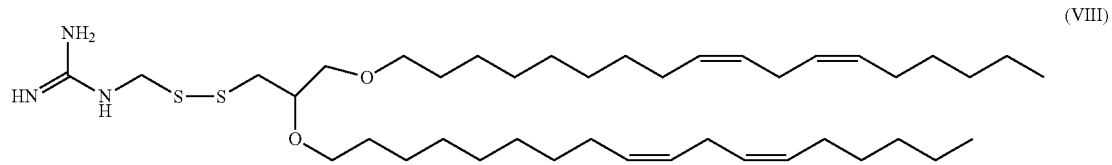 [SMILES: CCCCC/C=C\C/C=C\CCCCCCCCOCC(CSSCNC(=N)N)OCCCCCCCC/C=C\C/C=C\CCCCC]

(VIII)

In certain embodiments, the compounds disclosed herein are cationic and/or ionizable lipids, that may be used as a liposomal composition or alternatively as component of a liposomal composition (e.g., a lipid nanoparticle): In certain embodiments, the compounds disclosed herein are used to enrich a liposomal composition (e.g., lipid nanoparticles), thereby conferring improved properties to such enriched liposomal composition (e.g., improved delivery of encapsulated polynucleotides to one or more target cells and/or reduced in vivo toxicity of a liposomal composition). Accordingly, also contemplated are pharmaceutical compositions, and in particular liposomal compositions, that comprise one or more of the compounds disclosed herein. In certain embodiments, such pharmaceutical and liposomal compositions comprise one or more of a PEG-modified lipid, a non-cationic lipid and a helper lipid, such as cholesterol. For example, contemplated are pharmaceutical and liposomal compositions (e.g., lipid nanoparticles) that comprise one or more of the compounds disclosed herein (e.g., HGT4001, HGT4002, HGT4003, HGT4004 and/or HGT4005) and one or more cationic lipid, non-cationic lipid, a helper lipid/cholesterol, and PEG-modified lipid components. Also contemplated are pharmaceutical and liposomal compositions that comprise one or more of the compounds disclosed herein and that further comprise one or more additional cationic lipids. Similarly, also contemplated are liposomal compositions and pharmaceutical compositions (e.g., a lipid nanoparticle) that comprise one or more of the HGT4001, HGT4002, HGT4003, HGT4004 and/or HGT4005 compounds and one or more of C12-200, DLinDMA, DLinKC2-DMA, CHOL, DOPE, DMG-PEG-2000, ICE, DSPC, DODAP, DOTAP and C8-PEG-2000. In certain embodiments, such pharmaceutical compositions and liposomal compositions are loaded with or otherwise encapsulate materials, such as for example, one or more biologically-active polynucleotides.

In certain embodiments one or more of the pharmaceutical and liposomal compositions described herein (e.g., lipid nanoparticles) comprise one or more of the compounds disclosed herein and one or more additional lipids. For example, lipid nanoparticles that comprise or are otherwise enriched with one or more of the compounds disclosed herein may further comprise one or more of DOTAP (1,2-dioleyl-3-trimethylammonium propane), DODAP (1,2-dioleyl-3-dimethylammonium propane), DOTMA (1,2-di-O-octadecenyl-3-trimethylammonium propane), DLinDMA, DLin-KC2-DMA, C12-200 and ICE. In one embodiment the pharmaceutical composition comprises a lipid nanoparticle that comprises HGT4001, DOPE and DMG-PEG2000. In another embodiment the pharmaceutical composition comprises a lipid nanoparticle that comprises HGT4003, DOPE, cholesterol and DMG-PEG2000.

In certain embodiments one or more of the pharmaceutical compositions described herein may comprise one or more PEG-modified lipids. For example, lipid nanoparticles that comprise or are otherwise enriched with one or more of the compounds disclosed herein may further comprise one or more of PEG-modified lipids that comprise a poly(ethylene)glycol chain of up to 5 kDa in length covalently attached to a lipid comprising one or more $C_6$-$C_{20}$ alkyls.

Similarly, the pharmaceutical compositions disclosed herein (e.g., lipid nanoparticles) may comprise or may otherwise be enriched with one or more of the compounds disclosed herein and may further comprise one or more of helper lipids that are selected from the group consisting of DSPC (1,2-distearoyl-sn-glycero-3-phosphocholine), DPPC (1,2-dipalmitoyl-sn-glycero-3-phosphocholine), DOPE (1,2-dioleyl-sn-glycero-3-phosphoethanolamine), DPPE (1,2-dipalmitoyl-sn-glycero-3-phosphoethanolamine), DMPE (1,2-dimyristoyl-sn-glycero-3-phosphoethanolamine), DOPG (,2-dioleoyl-sn-glycero-3-phospho-(1'-rac-glycerol)), DOPE (1,2-dioleoyl-sn-glycero-3-phosphoethanolamine), DSPE (1,2-distearoyl-sn-glycero-3-phosphoethanolamine), DLPE (1,2-dilauroyl-sn-glycero-3-phosphoethanolamine), DPPS (1,2-dipalmitoyl-sn-glycero-3-phospho-L-serine), ceramides, sphingomyelins and cholesterol.

In certain embodiments, the compounds and the pharmaceutical and liposomal compositions comprising such compounds (e.g., lipid nanoparticles) comprise one or more polynucleotides (e.g., encapsulated DNA or RNA). In other embodiments, the one or more polynucleotides comprise at least one locked nucleic acid (e.g., two, three, four, five, six, seven, eight, nine, ten, twelve, fifteen, sixteen, eighteen, twenty, or more locked nucleic acid residues or monomers). Where the one or more encapsulated polynucleotides comprise RNA, such RNA may include, for example, mRNA, siRNA, snoRNA, microRNA, and combinations thereof.

In certain embodiments, the polynucleotides encapsulated in the pharmaceutical and liposomal compositions hereof comprise mRNA encoding, for example, a functional polypeptide, protein or enzyme, and upon being expressed (i.e., translated) by one or more target cells a functional polypeptide product (e.g., a protein or enzyme) is produced, and in some instances secreted by the target cell into the peripheral circulation of a subject. In certain embodiments, the one or more of the polynucleotides that comprise (or are otherwise loaded or encapsulated into) the compounds and pharmaceutical and liposomal compositions described herein encode a nucleic acid (e.g., a polypeptide) which is aberrantly expressed by the subject. In certain embodiments, the one or more of the encapsulated polynucleotides that comprise such compounds and liposomal or pharmaceutical compositions (e.g., a lipid nanoparticle) encode a functional enzyme such as a urea cycle enzyme (e.g., ornithine trans-carbamylase (OTC), carbamoyl-phosphate synthetase 1 (CPS1), argininosuccinate synthetase (ASS1), argininosuccinate lyase (ASL) or arginase 1 (ARG1)). In certain embodiments the one or more of the encapsulated polynucleotides comprises mRNA encoding an enzyme associated with a lysosomal storage disorder (e.g., the encapsulated polynucleotide is mRNA encoding one or more of the enzymes alpha galactosidase, iduronate-2-sulfatase, N-acetylglucosamine-1-phosphate transferase, beta-glucosidase, galactocerebrosidase, and glucosidase alpha acid). In other embodiments where the nucleic acids comprise mRNA, such mRNA may encode one or more proteins or enzymes, for example, proteins or enzymes that may be deficient in a subject (e.g., an enzyme or protein selected from the group of enzymes consisting of cystic fibrosis transmembrane conductance regulator (CFTR), alpha-L-iduronidase, N-acetylglucosaminidase, alpha-glucosaminide acetyltransferase, N-acetylglucosamine 6-sulfatase, N-acetylgalactosamine-4-sulfatase, galactose-6-sulfate sulfatase, beta-galactosidase, beta-glucuronidase, glucocerebrosidase, heparan sulfamidase, and hyaluronidase).

Also contemplated herein are pharmaceutical and liposomal compositions (e.g., lipid nanoparticles) that comprise one or more of the compounds disclosed herein and one or more polynucleotides (e.g., antisense oligonucleotides), and in particular polynucleotides that comprises one or more chemical modifications. For example, in certain embodiments where the polynucleotide is mRNA, such chemical modifications render the mRNA more stable and may comprise, for example an end blocking modification of a 5' or 3' untranslated region of the mRNA. In certain embodiments, the chemical modification comprises the inclusion of a partial sequence of a CMV immediate-early 1 (IE1) gene to the 5' untranslated region of the mRNA, such as, e.g., SEQ ID NO:1:

(SEQ ID NO: 1)
XCAGAUCGCCUGGAGACGCCAUCCACGCUGUUUUGACCUCCAUAGAAGA

CACCGGGACCGAUCCAGCCUCCGCGGCCGGGAACGGUGCAUUGGAACGC

GGAUUCCCCGUGCCAAGAGUGACUCACCGUCCUUGACACG,
wherein X, if present is GGA;

or a sequence that is at least 90% or at least 95% identical to SEQ ID NO:1.

In other embodiments the chemical modification comprises the inclusion of a poly A tail to the 3' untranslated region of the mRNA. Also contemplated are chemical modifications that comprise the inclusion of a Cap1 structure to the 5' untranslated region of the mRNA. In still other embodiments, the chemical modification comprises the inclusion of a sequence from the human growth hormone (hGH) gene to either the 3' untranslated region of the mRNA. The hGH sequence may comprise, e.g., SEQ ID NO:2

(SEQ ID NO: 2)
CGGGUGGCAUCCCUGUGACCCCUCCCCAGUGCCUCUCCUGGCCCUGGAA

GUUGCCACUCCAGUGCCCACCAGCCUUGUCCUAAUAAAAUUAAGUUGCA

UC or a sequence that is at least 90% or at least 95% identical to SEQ ID NO:2.

The compounds and pharmaceutical compositions described herein may be formulated to specifically target and/or transfect one or more target cells, tissues and organs. In certain embodiments, such compounds and pharmaceutical compositions facilitate the transfection of such target cells by one or more mechanisms (e.g., fusogenic-based release and/or proton-sponge mediated disruption of the lipid-bilayer membrane of the target cells). Contemplated target cells include, for example, one or more cells selected from the group consisting of hepatocytes, epithelial cells, hematopoietic cells, epithelial cells, endothelial cells, lung cells, bone cells, stem cells, mesenchymal cells, neural cells, cardiac cells, adipocytes, vascular smooth muscle cells, cardiomyocytes, skeletal muscle cells, beta cells, pituitary cells, synovial lining cells, ovarian cells, testicular cells, fibroblasts, B cells, T cells, reticulocytes, leukocytes, granulocytes and tumor cells.

The further invention provides pharmaceutical compositions that comprise lyophilized liposomal delivery vehicles and liposomal formulations (e.g., lipid nanoparticles) that are useful for effectuating the delivery of encapsulated contents (e.g., polynucleotides) to one or more target cells, tissues or organs. The invention further provides related methods and processes for preparing such pharmaceutical compositions, as well as methods of treating one or more diseases or conditions by administering such pharmaceutical compositions to a subject in need thereof. The lyophilized compositions (e.g., lipid nanoparticles) described herein are also expected to have improved long-term stability upon storage under either refrigeration or at ambient temperature (e.g., room temperature).

In certain embodiments, the pharmaceutical compositions comprising lyophilized nanoparticles or lyposomal delivery vehicles are characterized as being stable (e.g., as stable as pharmaceutical compositions comprising an equivalent unlyophilized vehicles). The stability of the lyophilized delivery vehicles may be determined, for example, with reference to the particle size of the lipid nanoparticles comprising such composition. In certain embodiments, lyophilization of the lipid nanoparticles does not appreciably change or alter the particle size of the lipid nanoparticles following lyophilization and/or reconstitution. For example, disclosed herein are pharmaceutical compositions comprising lyophilized lipid delivery vehicles, wherein upon reconstitution (e.g., with purified water) the lipid nanoparticles do not flocculate or aggregate, or alternatively demonstrated limited or negligible flocculation or aggregation (e.g., a determined by the particle size of the reconstituted lipid nanoparticles). Accordingly, in certain embodiments, upon reconstitution of a lyophilized lipid nanoparticle the lipid nanoparticles have a $Dv_{50}$ of less than about 500 nm (e.g., less than about 300 nm, 200 nm, 150 nm, 125 nm, 120 nm, 100 nm, 75 nm, 50 nm, 25 nm, or smaller). Similarly, in certain embodiments, upon reconstitution of a lyophilized lipid nanoparticle the lipid nanoparticles have a $Dv_{90}$ of less than about 750 nm (e.g., less than about 700 nm, 500 nm, 300 nm, 200 nm, 150 nm, 125 nm, 100 nm, 75 nm, 50 nm, 25 nm, or smaller).

In other embodiments, the pharmaceutical compositions comprising lyophilized lipid delivery vehicles are characterized as having a polydispersion index of less than about 1 (e.g., less than 0.95, 0.9, 0.8, 0.75, 0.7, 0.6, 0.5, 0.4, 0.3, 0.25, 0.2, 0.1, 0.05, or less). Still, in other embodiments, the pharmaceutical compositions comprising lyophilized lipid delivery vehicles demonstrate a reduced tendency to flocculate or otherwise aggregate (e.g., during lyophilization or upon reconstitution). For example, upon reconstitution the lipid delivery vehicles may have an average particle size ($Z_{ave}$) of less than 500 nm (e.g., less than about 400 nm, 300 nm, 200 nm, 175 nm, 150 nm, 125 nm, 100 nm, 75 nm, 50 nm, 25 nm, or smaller in a PBS solution).

The stable lyophilized lipid delivery vehicles (e.g., lipid nanoparticles) provided by the invention are also characterized by their improved storage properties. For example, in certain embodiments, the lyophilized lipid delivery vehicles may be stored under refrigeration and remain stable (e.g., as demonstrated by minimal or no losses in their intended pharmaceutical or biological activity) for extended periods of time (e.g., stable for at least about 1, 2, 3, 4, 5, 6, 9, 12, 18, 24, 36 months or longer upon storage at about 4° C.). In other embodiments, the lyophilized lipid delivery vehicles may be stored without refrigeration and remain stable for extended periods of time (e.g., stable for at least about 1, 2, 3, 4, 5, 6, 9, 12, 18, 24, 36 months or longer upon storage at about 25° C.). In certain embodiments, upon reconstitution with an appropriate rehydration media (e.g., purified water, deionized water, 5% dextrose and/or normal saline), the reconstituted composition demonstrates pharmacological or biological activity comparable with that observed prior to lyophilization. For example, in certain embodiments, the pharmacological or biological activity of an encapsulated polynucleotide is equivalent to that observed prior to lyophilization of the composition, or alternatively demonstrates a negligible reduction in pharmacological or biological activity (e.g., less than about a 1%, 2%, 2.5%, 4%, 5%, 7.5%, 10%, 12.5%, 15%, 18.5%, 20%, 25%, 30%, 35%, 40% or 50% reduction in the biological or pharmacological activity of an encapsulated polynucleotide).

Also disclosed herein are pharmaceutical compositions comprising lyophilized lipid delivery vehicles (e.g., lyophilized lipid nanoparticles) that further comprise or are alternatively prepared using one or more lyoprotectants (e.g., sugars and/or carbohydrates). In certain embodiments, the inclusion of one or more lyoprotectants in the lipid nanoparticle may improve or otherwise enhance the stability of the lyophilized lipid delivery vehicles (e.g., under normal storage conditions) and/or facilitate reconstitution of the lyophilized lipid delivery vehicles using a rehydration media, thereby preparing an aqueous formulation. For example, in certain embodiments the lipid nanoparticles are prepared and prior to lyophilization the buffer present in the liposomal formulation may be replaced (e.g., via centrifugation) with a lyoprotectant such as a sucrose solution or suspension (e.g., an aqueous solution comprising between about 1-50% or 10-25% sucrose). Other suitable lyoprotectants that may be used to prepare the lyophilized compositions described herein include, for example, trehalose, dextran (e.g., 1.5 kDa, 5 kDa and/or 40 kDa) and inulin (e.g., 1.8 kDa and/or 4 kDa).

In some embodiments, the lyophilized compositions disclosed herein are also capable of facilitating the extended release of the contents (e.g., polynucleotides) encapsulated in one or more lipid nanoparticles comprising such composition. For example, contemplated are pharmaceutical compositions comprising lyophilized lipid delivery vehicles, wherein the composition may be implanted into a subject without reconstitution (e.g., implanted subcutaneously, for example, as a membrane or a disk). Such implanted lyophilized compositions may erode or otherwise disintegrate at a predetermined rate, for example, upon exposure to one or more biological fluids (e.g., serum, blood, cerebrospinal fluid, mucous, sweat, gastric secretions, urine and/or saliva). In certain embodiments, such implanted pharmaceutical compositions comprising lyophilized lipid delivery vehicles release, for example, encapsulated polynucleotides over at least 1, 2, 7, 10, 14, 21, 30, 45, 60, 90, 120 days or longer. Alternatively, such implanted compositions comprising lyophilized lipid delivery vehicles release, for example, encapsulated polynucleotides over at least one, two, three, six, twelve, sixteen twenty-four, thirty-six months or longer.

In certain embodiments, the pharmaceutical compositions comprising lyophilized lipid delivery vehicles provided by the invention herein may be reconstituted prior to administration to a subject (e.g., a mammal). Upon reconstitution (e.g., using purified water or 5% dextrose as a rehydration media) the reconstituted aqueous composition may be administered to a subject by one or more of the following routes of administration: intravenously, orally, rectally, vaginally, transmucosally, sublingually, subdurally, nasally, intramuscularly, subcutaneously, intramedullary injection, intrathecally, intraventricularly, intraperitoneally, intranasally, opthalmically and/or intraocularly.

The invention also provides are methods of treating disease (e.g., a disease associated with the aberrant expression of a gene or nucleic acid) in a subject, wherein the method comprises administering one or more of the compounds and/or pharmaceutical compositions of the invention to the subject. Also contemplated are methods of transfecting one or more target cells with one or more polynucleotides, wherein the method comprises contacting the one or more target cells with the compounds or pharmaceutical composition described herein such that the one or more target cells are transfected with the one or more encapsulated polynucleotides.

In certain embodiments, the methods of treatment provided by the invention employ the compositions comprising lyophilized or reconstituted lipid delivery vehicles of the invention, which are capable of modulating the expression of aberrantly expressed nucleic acids and polynucleotides in one or more target cells and tissues. Accordingly, also provided herein are methods of treating disease in a subject by administering an effective amount of pharmaceutical compositions comprising lyophilized lipid delivery vehicles provided by the invention to a subject (e.g., upon reconstitution with a rehydrating media such as sterile water for injection). In certain embodiments, such methods may enhance (e.g., increase) the expression of a polynucleotide and/or increase the production and secretion of a functional polypeptide product in one or more target cells and tissues (e.g., hepatocytes). In some embodiments, the targeted cells or tissues aberrantly express the polynucleotide encapsulated by one or more of the lyophilized lipid delivery vehicles (e.g., lipid nanoparticles) of the invention.

The invention also provides methods of increasing the expression of one or more polynucleotides (e.g., mRNA) in one or more target cells, tissues and organs. Generally, such methods comprise contacting the target cells with one or more compounds and/or pharmaceutical or liposomal compositions that comprise or otherwise encapsulate one or more polynucleotides. In some embodiments, the present inventions also related to methods of transfecting one or more cells with a polynucleotide (e.g., comprising the steps of rehydrating a lyophilized composition and contacting such one or more cells with the rehydrated composition).

The above discussed and many other features and attendant advantages of the present invention will become better understood by reference to the following detailed description of the invention when taken in conjunction with the accompanying examples. The various embodiments described herein are complimentary and can be combined or used together in a manner understood by the skilled person in view of the teachings contained herein.

DESCRIPTION OF EXEMPLARY EMBODIMENTS

Figure 1:
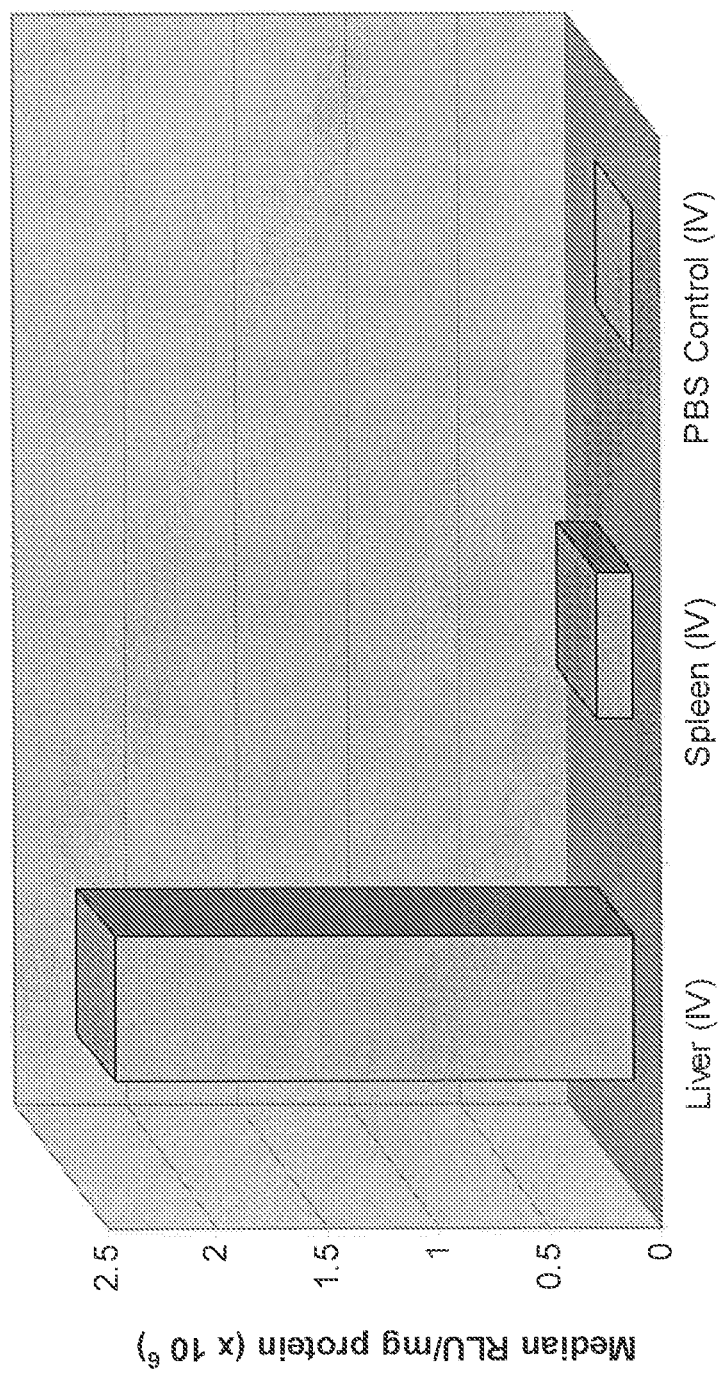
FIG. 1 illustrates the luminescence output of firefly luciferase protein in liver and spleen of mice following intravenous administration of an HGT4003-based, firefly luciferase (FFL) mRNA-loaded lipid nanoparticles. The administered HGT4003-based lipid nanoparticles afford an enrichment of encapsulated mRNA in the liver over the spleen. Values are depicted as median relative light units (RLU)/mg of total protein four hours post-administration.

The compounds of the invention are useful, for example, as liposomal delivery vehicles or as components of liposomal delivery vehicles. In certain embodiments, the compounds disclosed herein may be used as a liposomal composition or alternatively as component of a liposomal composition (e.g., as a lipid nanoparticle). The compounds of the invention may also be employed in pharmaceutical compositions (e.g., lipid nanoparticles) and methods of administering such pharmaceutical compositions to treat or prevent a disease, disorder, or condition or to deliver a therapeutic molecule. In certain embodiments, such compounds and compositions facilitate the delivery of, for example, encapsulated materials (e.g., polynucleotides) to one or more target cells, tissues and organs.

The compounds disclosed herein generally comprise one or more cleavable groups such as, for example, one or more disulfide (S—S) functional groups as depicted in formula I below. The terms "cleave" and "cleavable" are generally used herein to mean that one or more chemical bonds (e.g., one or more of covalent bonds, hydrogen-bonds, van der Waals' forces and/or ionic interactions) between atoms in or adjacent to the subject functional group are broken (e.g., hydrolyzed) or are capable of being broken upon exposure to selected conditions (e.g., upon exposure to enzymatic conditions). In certain embodiments, the cleavable group is a disulfide functional group, and in particular embodiments is a disulfide group that is capable of being cleaved upon exposure to selected biological conditions (e.g., intracellular conditions). In certain embodiments, the cleavable group is an ester functional group that is capable of being cleaved upon exposure to selected biological conditions. For example, the disulfide groups may be cleaved enzymatically or by a hydrolysis, oxidation or reduction reaction. Upon cleavage of such disulfide functional group, the one or more functional moieties or groups (e.g., one or more of a head-group and/or a tail-group) that are bound thereto may be liberated. Exemplary cleavable groups may include, but are not limited to, disulfide groups, ester groups, ether groups, and any derivatives thereof (e.g., alkyl and aryl esters). In certain embodiments, the cleavable group is not an ester group or an ether group.

The cleavable groups described herein are generally bound (e.g., bound by one or more of hydrogen-bonds, van der Waals' forces, ionic interactions and covalent bonds) to one or more functional moieties or groups (e.g., at least one head-group and at least one tail-group). In certain embodiments, at least one of the functional moieties or groups is hydrophilic (e.g., a hydrophilic head-group comprising one or more of imidazole, guanidinium, amino, imine, enamine, optionally-substituted alkyl amino and pyridyl). As used herein, the term "hydrophilic" is used to indicate in qualitative terms that a functional group is water-preferring, and typically such groups are water-soluble. For example, disclosed herein are compounds that comprise a cleavable disulfide (S—S) functional group bound to one or more hydrophilic groups (e.g., a hydrophilic head-group), wherein such hydrophilic groups comprise or are selected from the group consisting of imidazole, guanidinium, amino, imine, enamine, an optionally-substituted alkyl amino (e.g., an alkyl amino such as dimethylamino) and pyridyl.

In certain embodiments, the selected hydrophilic functional group or moiety may alter or otherwise impart properties to the compound or to the liposomal composition of which such compound is a component (e.g., by improving the transfection efficiencies of a lipid nanoparticle of which the compound is a component). For example, the incorporation of guanidinium as a hydrophilic head-group in the compounds disclosed herein may promote the fusogenicity of such compound (or of the liposomal composition of which such compound is a component) with the cell membrane of one or more target cells, thereby enhancing, for example, the transfection efficiencies of such compound. It has been hypothesized that the nitrogen from the hydrophilic guanidinium moiety forms a six-membered ring transition state which grants stability to the interaction and thus allows for cellular uptake of encapsulated materials. (Wender, et al., *Adv. Drug Del. Rev.* (2008) 60: 452-472.) Similarly, the incorporation of one or more amino groups or moieties into the disclosed compounds (e.g., as a head-group) may further promote disruption of the endosomal/lysosomal membrane of the target cell by exploiting the fusogenicity of such amino groups. This is based not only on the pKa of the amino group of the composition, but also on the ability of the amino group to undergo a hexagonal phase transition and fuse with the target cell surface, i.e., the vesicle membrane. (Koltover, et al. *Science* (1998) 281: 78-81.) The result is believed to promote the disruption of the vesicle membrane and release of the lipid nanoparticle contents into the target cell.

Similarly, in certain embodiments the incorporation of, for example, imidazole as a hydrophilic head-group in the compounds disclosed herein may serve to promote endosomal or lysosomal release of, for example, contents that are encapsulated in a liposomal composition (e.g., lipid nanoparticle) of the invention. Such enhanced release may be achieved by one or both of proton-sponge mediated disruption mechanism and/or an enhanced fusogenicity mechanism. The proton-sponge mechanism is based on the ability of a compound, and in particular a functional moiety or group of the compound, to buffer the acidification of the endosome. This may be manipulated or otherwise controlled by the pKa of the compound or of one or more of the functional groups comprising such compound (e.g., imidazole). Accordingly, in certain embodiments the fusogenicity of, for example, the imidazole-based compounds disclosed herein (e.g., HGT4001 and HGT4004) are related to the endosomal disruption properties, which are facilitated by such imidazole groups, which have a lower pKa relative to other traditional cationic lipids. Such endosomal disruption properties in turn promote osmotic swelling and the disruption of the liposomal membrane, followed by the transfection or intracellular release of the polynucleotide materials loaded or encapsultated therein into the target cell. This phenomenon can be applicable to a variety of compounds with desirable pKa profiles in addition to an imidazole moiety. Such embodiments also include multi-nitrogen based functionalities such as polyamines, poly-peptide (histidine), and nitrogen-based dendritic structures.

The compounds, and in particular the imidazole-based compounds described herein (e.g., HGT4001 and HGT4004), are also characterized by their reduced toxicity, in particular relative to traditional lipids and cationic lipids. In some embodiments, the pharmaceutical and liposomal compositions described herein comprise one or more imidazole-based cationic lipid compounds such that the relative concentration of other more toxic cationic lipids in such pharmaceutical or liposomal composition may be reduced or otherwise eliminated. The imidazole-based compounds or lipids (e.g., HGT4001 and/or HGT4004) may be used as the sole cationic lipid in one or more of the pharmaceutical and liposomal compositions described herein (e.g., lipid nanoparticles), or alternatively may be combined with traditional cationic lipids (e.g., LIPOFECTIN or LIPOFECTAMINE), non-cationic lipids, helper lipids/cholesterol, and/or PEG-modified lipids. In certain embodiments, the compounds described herein, or alternatively the total cationic lipid component of the pharmaceutical and liposomal compositions may comprise a molar ratio of about 1% to about 90%, about 2% to about 70%, about 5% to about 50%, about 10% to about 40% of the total lipid present in such pharmaceutical or liposomal composition (e.g., a lipid nanoparticle), or preferably about 20% to about 70% of the total lipid present in such pharmaceutical or liposomal composition (e.g., a lipid nanoparticle).

In certain embodiments, at least one of the functional groups of moieties that comprise the compounds disclosed herein is hydrophobic in nature (e.g., a hydrophobic tail-group comprising a naturally-occurring lipid such as cholesterol). As used herein, the term "hydrophobic" is used to indicate in qualitative terms that a functional group is water-avoiding, and typically such groups are not water soluble. For example, disclosed herein are compounds that comprise a cleavable functional group (e.g., a disulfide (S—S) group) bound to one or more hydrophobic groups, wherein such hydrophobic groups comprise one or more naturally occurring lipids such as cholesterol, and/or an optionally substituted, variably saturated or unsaturated $C_6$-$C_{20}$ alkyl and/or an optionally substituted, variably saturated or unsaturated $C_6$-$C_{20}$ acyl.

In certain embodiments, the compounds disclosed herein comprise, for example, at least one hydrophilic head-group and at least one hydrophobic tail-group, each bound to at least one cleavable group, thereby rendering such compounds amphiphilic. As used herein to describe a compound or composition, the term "amphiphilic" means the ability to dissolve in both polar (e.g., water) and non-polar (e.g., lipid) environments. For example, in certain embodiments, the compounds disclosed herein comprise at least one lipophilic tail-group (e.g., cholesterol or a $C_6$-$C_{20}$ alkyl) and at least one hydrophilic head-group (e.g., imidazole), each bound to a cleavable group (e.g., disulfide).

It should be noted that the terms "head-group" and "tail-group" as used describe the compounds of the present invention, and in particular functional groups that comprise such compounds, are used for ease of reference to describe the orientation of one or more functional groups relative to other functional groups. For example, in certain embodiments a hydrophilic head-group (e.g., guanidinium) is bound (e.g., by one or more of hydrogen-bonds, van der Waals' forces, ionic interactions and covalent bonds) to a cleavable functional group (e.g., a disulfide group), which in turn is bound to a hydrophobic tail-group (e.g., cholesterol).

Also disclosed herein are compounds having the structure of formula I,

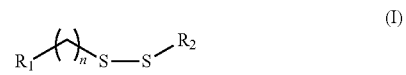

(I)

wherein $R_1$ is selected from the group consisting of imidazole, guanidinium, amino, imine, enamine, an optionally-substituted alkyl amino (e.g., an alkyl amino such as dimethylamino) and pyridyl; wherein $R_2$ is selected from the group consisting of formula II and formula III;

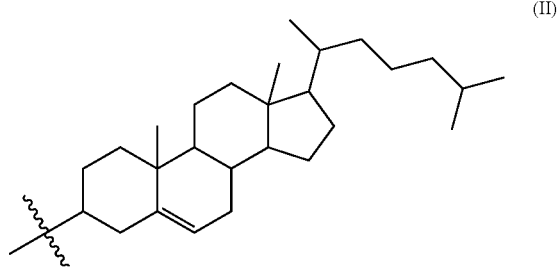

(II)

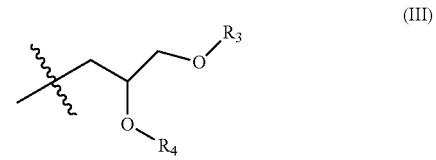

(III)

wherein $R_3$ and $R_4$ are each independently selected from the group consisting of an optionally substituted, variably saturated or unsaturated $C_6$-$C_{20}$ alkyl and an optionally substituted, variably saturated or unsaturated $C_6$-$C_{20}$ acyl; and wherein n is zero or any positive integer (e.g., one, two, three, four, five, six, seven, eight, nine, ten, eleven, twelve, thirteen, fourteen, fifteen, sixteen, seventeen, eighteen, nineteen, twenty or more). In certain embodiments, each of $R_3$ and $R_4$ comprise an optionally substituted, polyunsaturated $C_{18}$ alkyl, while in other embodiments $R_3$ and $R_4$ are each an unsubstituted, polyunsaturated $C_{18}$ alkyl. In certain embodiments, each of $R_3$ and $R_4$ are (9Z,12Z)-octadeca-9,12-dien. In certain embodiments, n is 1 (such that the alkyl is ethyl), 2 (such that the alkyl is methyl), 3 (such that the alkyl is, for example, propyl or iso-propyl), 4 (such that the alkyl is, for example, butyl, iso-butyl, sec-butyl or ter-butyl), 5 (such that the alkyl is, for example, pentane), 6 (such that the alkyl is, for example, hexane), 7 (such that the alkyl is, for example, heptane), 8 (such that the alkyl is, for example, octane), 9 (n such that the alkyl is, for example, nonane) or 10 (such that the alkyl is, for example, decane).

As used herein, the term "alkyl" refers to both straight and branched chain $C_1$-$C_{40}$ hydrocarbons (e.g., $C_6$-$C_{20}$ hydrocarbons), and include both saturated and unsaturated hydrocarbons. In certain embodiments, the alkyl may comprise one or more cyclic alkyls and/or one or more heteroatoms such as oxygen, nitrogen, or sulfur and may optionally be substituted with substituents (e.g., one or more of alkyl, halo, alkoxyl, hydroxy, amino, aryl, ether, ester or amide). In certain embodiments, a contemplated alkyl includes (9Z,12Z)-octadeca-9,12-dien. The use of designations such as, for example, "$C_6$-$C_{20}$" is intended to refer to an alkyl (e.g., straight or branched chain and inclusive of alkenes and alkyls) having the recited range carbon atoms.

As used herein, the term "aryl" refers to aromatic groups (e.g., monocyclic, bicyclic and tricyclic structures) containing six to ten carbons in the ring portion. The aryl groups may be optionally substituted through available carbon atoms and in certain embodiments may include one or more heteroatoms such as oxygen, nitrogen or sulfur.

Also disclosed herein are pharmaceutical compositions that comprise the compound of formula I, wherein $R_1$ is selected from the group consisting of imidazole, guanidinium, amino, imine, enamine, an optionally-substituted alkyl amino (e.g., dimethylamino) and pyridyl; wherein $R_2$ is formula II; and wherein n is zero or any positive integer (e.g., one, two, three, four, five, six, seven, eight, nine, ten or more). Further disclosed herein are pharmaceutical compositions comprising the compound of formula I, wherein $R_1$ is selected from the group consisting of imidazole, guanidinium, imine, enamine, amino, an optionally-substituted alkyl amino (e.g., dimethylamino) and pyridyl; wherein $R_2$ is formula III; wherein $R_3$ and $R_4$ are each independently selected from the group consisting of an optionally substituted, variably saturated or unsaturated $C_6$-$C_{20}$ alkyl and an optionally substituted, variably saturated or unsaturated $C_6$-$C_{20}$ acyl; and wherein n is zero or any positive integer. In certain embodiments, $R_3$ and $R_4$ are each an optionally substituted, polyunsaturated $C_{18}$ alkyl, while in other embodiments $R_3$ and $R_4$ are each an unsubstituted, polyunsaturated $C_{18}$ alkyl. In certain embodiments, a contemplated alkyl includes (9Z,12Z)-octadeca-9,12-dien.

In certain embodiments, the $R_1$ group or head-group is a polar or hydrophilic group (e.g., one or more of the imidazole, guanidinium and amino groups) and is bound to the $R_2$ lipid group by way of the disulfide (S—S) cleavable linker group, for example as depicted in formula I. The $R_1$ group or head-group may be covalently bound to the cleavable linker group by way of an alkyl group (e.g., a $C_1$-$C_{20}$ alkyl where n is one to twenty), or alternatively may be directly bound to the cleavable linker group (e.g., where n is zero). The compounds and pharmaceutical compositions disclosed herein may be prepared such that upon exposure to selected conditions (e.g., appropriate biological or enzymatic conditions) the cleavable linker group (e.g., a disulfide group) is cleaved and thereby causes the dissociation of one or more of the functional groups or moieties (e.g., a head- and/or tail-group) bound thereto. The dissociation of the functional groups or moieties (e.g., an $R_1$ hydrophilic group such as imidazole) may cause a phase transition in the liposomal composition of which one or more of the compounds disclosed herein is a component which thereby destabilizes the liposome and facilitates fusion with the membrane of one or more target cells. Other contemplated cleavable linker groups may include compositions that comprise one or more disulfide (S—S) linker group bound (e.g., covalently bound) to, for example an alkyl group (e.g., $C_1$ to $C_{10}$ alkyl).

In certain embodiments, the invention provides the compound 5-(((10,13-dimethyl-17-(6-methylheptan-2-yl)-2,3,4,7,8,9,10,11,12,13,14,15,16,17-tetradecahydro-1H-cyclopenta[a]phenanthren-3-yl)disulfanyl)methyl)-1H-imidazole, having the structure of formula IV (referred to herein as "HGT4001").

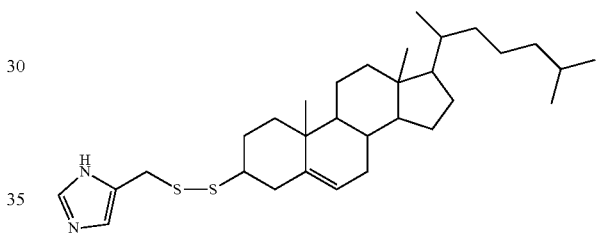

(IV)

In certain embodiments, the invention provides the compound 1-(2-(((3S,10R,13R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yl)disulfanyl)ethyl) guanidine, having the structure of formula V (referred to herein as "HGT4002").

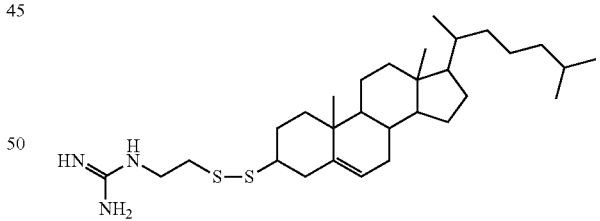

(V)

In certain embodiments, the invention provides the compound 2-((2,3-Bis((9Z,12Z)-octadeca-9,12-dien-1-yloxy)propyl)disulfanyl)-N,N-dimethylethanamine, having the structure of formula VI (referred to herein as "HGT4003").

(VI)

In other embodiments, the invention provides the compound 5-(((2,3-bis((9Z,12Z)-octadeca-9,12-dien-1-yloxy)propyl)disulfanyl)methyl)-1H-imidazole having the structure of formula VII (referred to herein as "HGT4004").

ments the compounds described herein (and the pharmaceutical and liposomal compositions comprising such compounds) are characterized as having one or more of receptor-mediated endocytosis, clathrin-mediated and caveolae-

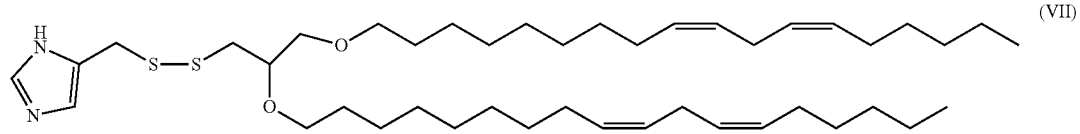 [SMILES: CCCCC/C=C\C/C=C\CCCCCCCCOCC(CSSCc1cnc[nH]1)OCCCCCCCC/C=C\C/C=C\CCCCC]

(VII)

In still other embodiments, the invention provides the compound 1-(((2,3-bis((9Z,12Z)-octadeca-9,12-dien-1-yloxy)propyl)disulfanyl)methyl)guanidine having the structure of formula VIII (referred to herein as "HGT4005").

mediated endocytosis, phagocytosis and macropinocytosis, fusogenicity, endosomal or lysosomal disruption and/or releasable properties that afford such compounds advantages relative other similarly classified lipids.

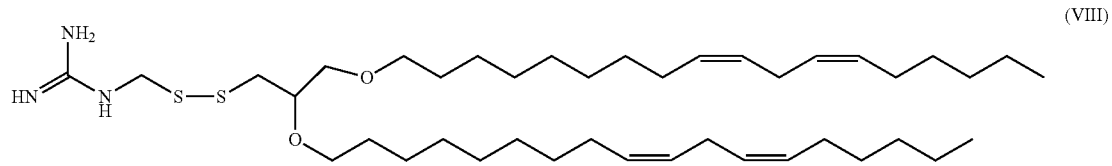 [SMILES: CCCCC/C=C\C/C=C\CCCCCCCCOCC(CSSCNC(=N)N)OCCCCCCCC/C=C\C/C=C\CCCCC]

(VIII)

The compounds described herein may be used to construct liposomal compositions that facilitate or enhance the delivery and release of encapsulated materials (e.g., one or more therapeutic polynucleotides) to one or more target cells (e.g., by permeating or fusing with the lipid membranes of such target cells). In certain embodiments, the one or more cleavable functional groups that comprise such compounds allow, for example, a hydrophilic functional head-group to be dissociated (e.g., upon exposure to reducing or acidic conditions) from a lipophilic functional tail-group of the compound, thereby facilitating a phase transitions in the lipid bilayer of one or more target cells. For example, when a liposomal composition (e.g., a lipid nanoparticle) comprises or is otherwise enriched with one or more of the compounds disclosed herein, the phase transition in the lipid bilayer of the one or more target cells facilitates the delivery of the encapsulated materials (e.g., one or more therapeutic polynucleotides encapsulated in a lipid nanoparticle) into the one or more target cells.

In certain embodiments the compounds described herein are characterized as having one or more properties that afford such compounds advantages relative to other similarly classified lipids. For example, in certain embodiments, the compounds disclosed herein allow for the control and tailoring of the properties of liposomal compositions (e.g., lipid nanoparticles) of which they are a component. In particular, the compounds disclosed herein may be characterized by enhanced transfection efficiencies and their ability to provoke specific biological outcomes. Such outcomes may include, for example enhanced cellular uptake, endosomal/lysosomal disruption capabilities and/or promoting the release of encapsulated materials (e.g., polynucleotides) intracellularly.

In certain embodiments the compounds described herein (and the pharmaceutical and liposomal compositions comprising such compounds) employ a multifunctional strategy to facilitate the delivery of encapsulated materials (e.g., one or more polynucleotides) to, and subsequent transfection of one or more target cells. For example, in certain embodi- In certain embodiments the compounds and the pharmaceutical and liposomal compositions of which such compounds are a component (e.g., lipid nanoparticles) exhibit an enhanced (e.g., increased) ability to transfect one or more target cells. Accordingly, also provided herein are methods of transfecting one or more target cells. Such methods generally comprise the step of contacting the one or more target cells with the compounds and/or pharmaceutical compositions disclosed herein (e.g., an HGT4003-based lipid nanoparticle encapsulating one or more polynucleotides) such that the one or more target cells are transfected with the materials encapsulated therein (e.g., one or more polynucleotides). As used herein, the terms "transfect" or "transfection" refer to the intracellular introduction of one or more encapsulated materials (e.g., nucleic acids and/or polynucleotides) into a cell, or preferably into a target cell. The introduced polynucleotide may be stably or transiently maintained in the target cell. The term "transfection efficiency" refers to the relative amount of such encapsulated material (e.g., polynucleotides) up-taken by, introduced into and/or expressed by the target cell which is subject to transfection. In practice, transfection efficiency is estimated by the amount of a reporter polynucleotide product produced by the target cells following transfection. In certain embodiments, the compounds and pharmaceutical compositions described herein demonstrate high transfection efficiencies thereby improving the likelihood that appropriate dosages of the encapsulated materials (e.g., one or more polynucleotides) will be delivered to the site of pathology and subsequently expressed, while at the same time minimizing potential systemic adverse effects.

A wide range of materials that can exert pharmaceutical or therapeutic effects can be delivered to target cells using the compounds, compositions and methods of the present invention. Accordingly, the compounds and pharmaceutical and liposomal compositions described herein may be used to encapsulate any materials suitable for intracellular delivery. In certain embodiments, such encapsulated materials are capable of conferring a therapeutic or diagnostic benefit upon the cells into which such materials are delivered, and may include any drugs, biologics and/or diagnostics. The materials can be organic or inorganic. Organic molecules can be peptides, proteins, carbohydrates, lipids, sterols, nucleic acids (including peptide nucleic acids), or any combination thereof. In certain embodiments, the pharmaceutical and liposomal compositions described herein can comprise or otherwise encapsulate more than one type of material, for example, two or more different polynucleotide sequences encoding a protein, an enzyme and/or a steroid. In certain embodiments, the encapsulated materials are one or more polynucleotides and nucleic acids.

As used herein, the terms "polynucleotide" and "nucleic acid" are used interchangeably to refer to genetic material (e.g., DNA or RNA), and when such terms are used with respect to the compounds and compositions described herein (e.g., lipid nanoparticles) generally refer to the genetic material encapsulated by such compounds and compositions (e.g., lipid nanoparticles). In some embodiments, the polynucleotide is RNA. Suitable RNA includes mRNA, siRNA, miRNA, snRNA and snoRNA. Contemplated polynucleotides also include large intergenic non-coding RNA (lincRNA), which generally does not encode proteins, but rather function, for example, in immune signaling, stem cell biology and the development of disease. (See, e.g., Guttman, et al., 458: 223-227 (2009); and Ng, et al., Nature Genetics 42: 1035-1036 (2010), the contents of which are incorporated herein by reference). In preferred embodiments, the polynucleotide is mRNA. In certain embodiments, the polynucleotides encapsulated by the compounds or pharmaceutical and liposomal compositions of the invention include RNA or stabilized RNA encoding a protein or enzyme (e.g., mRNA encoding alfa galactosidase). The present invention contemplates the use of such polynucleotides (and in particular RNA or stabilized RNA) as a therapeutic that is capable of being expressed by target cells to thereby facilitate the production (and in certain instances the excretion) of a functional enzyme or protein by such target cells as disclosed for example, in International Application No. PCT/US2010/058457 and in U.S. Provisional Application No. 61/494,881, filed Jun. 8, 2011, the teachings of which are both incorporated herein by reference in their entirety. For example, in certain embodiments, upon the expression of one or more polynucleotides by target cells the production of a functional enzyme or protein in which a subject is deficient (e.g., a urea cycle enzyme or an enzyme associated with a lysosomal storage disorder) may be observed. The term "functional", as used herein to qualify a protein or enzyme, means that the protein or enzyme has biological activity, or alternatively is able to perform the same, or a similar function as the native or normally-functioning protein or enzyme.

In the context of the present invention the term "expression" is used in its broadest sense to refer to either the transcription of a specific gene or polynucleotide into at least one mRNA transcript, or the translation of at least one mRNA or polynucleotide into a protein or enzyme. For example, in certain embodiments the compounds and the pharmaceutical or liposomal compositions described herein comprise a polynucleotide (e.g., mRNA) which encodes a functional protein or enzyme. In the context of such mRNA polynucleotides, the term expression refers to the translation of such mRNA (e.g., by the target cells) to produce the polypeptide or protein encoded thereby.

In certain embodiments, the compounds and pharmaceutical compositions provided herein are capable of modulating the expression of aberrantly expressed nucleic acids and polynucleotides in one or more target cells and tissues. Accordingly, also provided herein are methods of treating disease in a subject by administering an effective amount of the compounds and/or the pharmaceutical or liposomal compositions described herein to the subject. In certain embodiments, such methods may enhance (e.g., increase) the expression of a polynucleotide and/or increase the production and secretion of a functional polypeptide product in one or more target cells and tissues (e.g., hepatocytes). In some embodiments, the targeted cells or tissues aberrantly express the polynucleotide encapsulated by one or more of the compounds or pharmaceutical and liposomal compositions (e.g., lipid nanoparticles) described herein. Also provided herein are methods of increasing the expression of one or more polynucleotides (e.g., mRNA) in one or more target cells, tissues and organs. Generally, such methods comprise contacting the target cells with one or more compounds and/or pharmaceutical or liposomal compositions that comprise or otherwise encapsulate one or more polynucleotides.

In certain embodiments, the compounds disclosed herein may be used as a liposome or as a component of a liposome. Specifically, in certain embodiments the compounds disclosed herein may be used as a lipid (e.g., cationic lipid) component of a liposomal composition (e.g., a lipid nanoparticle). Such liposomes may be used to encapsulate materials and facilitate the delivery of such materials to one or more target cells, tissues and organs. As used herein, the term "liposome" generally refers to a vesicle composed of lipids (e.g., amphiphilic lipids) arranged in one or more spherical bilayer or bilayers. In certain embodiments, the liposome is a lipid nanoparticle (e.g., a lipid nanoparticle comprising one or more of the cationic lipid compounds disclosed herein). Such liposomes may be unilamellar or multilamellar vesicles which have a membrane formed from a lipophilic material and an aqueous interior that contains the encapsulated materials (e.g., polynucleotides) to be delivered to one or more target cells, tissues and organs. In certain embodiments, the pharmaceutical and liposomal compositions described herein comprise one or more lipid nanoparticles. Contemplated liposomes include lipid nanoparticles. Examples of suitable lipids (e.g., cationic lipids) that may be used to form the liposomes and lipid nanoparticles contemplated hereby include one or more of the compounds disclosed herein (e.g., HGT4001, HGT4002, HGT4003, HGT4004 and/or HGT4005). Such liposomes and lipid nanoparticles may also comprise additional cationic lipids such as C12-200, DLin-KC2-DMA, and/or HGT5001, non-cationic lipids, helper/cholesterol-based lipids, PEG-modified lipids, as well as the phosphatidyl compounds (e.g., phosphatidylglycerol, phosphatidylcholine, phosphatidylserine, phosphatidylethanolamine, sphingolipids, cerebrosides, and gangliosides) and combinations or mixtures of the forgoing.

Several cationic lipids have been described in the literature, many of which are commercially available. In certain embodiments, such cationic lipids are included in the pharmaceutical or liposomal compositions described herein in addition to one or more of the compounds or lipids disclosed herein (e.g., HGT4003). In some embodiments, the cationic lipid N-[1-(2,3-dioleyloxy)propyl]-N,N,N-trimethylammonium chloride or "DOTMA" is used. (Feigner et al. (Proc. Nat'l Acad. Sci. 84, 7413 (1987); U.S. Pat. No. 4,897,355). DOTMA can be formulated alone or can be combined with a neutral lipid, dioleoylphosphatidylethanolamine or "DOPE" or other cationic or non-cationic lipids into a lipid nanoparticle. Other suitable cationic lipids include, for example, ionizable cationic lipids as described in U.S.

provisional patent application 61/617,468, filed Mar. 29, 2012 (incorporated herein by reference), such as, e.g, (15Z,18Z)-N,N-dimethyl-6-(9Z,12Z)-octadeca-9,12-dien-1-yl) tetracosa-15,18-dien-1-amine (HGT5000), (15Z,18Z)-N,N-dimethyl-6-((9Z,12Z)-octadeca-9,12-dien-1-yl)tetracosa-4, 15,18-trien-1-amine (HGT5001), and (15Z,18Z)-N,N-dimethyl-6-((9Z,12Z)-octadeca-9,12-dien-1-yl)tetracosa-5, 15,18-trien-1-amine (HGT5002); C12-200 (WO 2010/053572), 2-(2,2-di((9Z,12Z)-octadeca-9,12-dien-1-yl)-1,3-dioxolan-4-yl)-N,N-dimethylethanamine (DLinKC2-DMA)) (See, WO 2010/042877; Semple et al., nature Biotech. 28:172-176 (2010)), 2-(2,2-di((9Z,12Z)-octadeca-9,12-dien-1-yl)-1,3-dioxolan-4-yl)-N,N-dimethylethanamine "DLin-KC2-DMA," (3S,10R,13R,17R)-10,13-dimethyl-17-((R)-6-methylheptan-2-yl)-2, 3, 4, 7, 8, 9, 10, 11, 12, 13, 14, 15, 16, 17-tetradecahydro-1H-cyclopenta[a]phenanthren-3-yl 3-(1H-imidazol-4-yl)propanoate "ICE," (15Z,18Z)-N,N-dimethyl-6-(9Z,12Z)-octadeca-9,12-dien-1-yl)tetracosa-15,18-dien-1-amine "HGT5000," (15Z,18Z)-N,N-dimethyl-6-((9Z,12Z)-octadeca-9,12-dien-1-yl)tetracosa-4,15,18-trien-1-amine "HGT5001," and (15Z,18Z)-N,N-dimethyl-6-((9Z,12Z)-octadeca-9,12-dien-1-yl)tetracosa-5, 15,18-trien-1-amine "HGT5002," 5-carboxyspermylglycine-dioctadecylamide or "DOGS," 2,3-dioleyloxy-N-[2(spermine-carboxamido)ethyl]-N,N-dimethyl-1-propanaminium or "DOSPA" (Behr et al. Proc. Nat.'l Acad. Sci. 86, 6982 (1989); U.S. Pat. Nos. 5,171,678; 5,334,761), 1,2-Dioleoyl-3-Dimethylammonium-Propane or "DODAP", 1,2-Dioleoyl-3-Trimethylammonium-Propane or "DOTAP". Contemplated cationic lipids also include 1,2-distearyloxy-N,N-dimethyl-3-aminopropane or "DSDMA", 1,2-dioleyloxy-N,N-dimethyl-3-aminopropane or "DODMA", 1,2-dilinoleyloxy-N,N-dimethyl-3-aminopropane or "DLinDMA", 1,2-dilinolenyloxy-N,N-dimethyl-3-aminopropane or "DLenDMA", N-dioleyl-N,N-dimethylammonium chloride or "DODAC", N,N-distearyl-N,N-dimethylammonium bromide or "DDAB", N-(1,2-dimyristyloxyprop-3-yl)-N,N-dimethyl-N-hydroxyethyl ammonium bromide or "DMRIE", 3-dimethylamino-2-(cholest-5-en-3-beta-oxybutan-4-oxy)-1-(cis,cis-9,12-octadecadienoxy)propane or "CLinDMA", 2-[5'-(cholest-5-en-3-beta-oxy)-3'-oxapentoxy)-3-dimethyl-1-(cis,cis-9',1-2'-octadecadienoxy)propane or "CpLinDMA", N,N-dimethyl-3,4-dioleyloxybenzylamine or "DMOBA", 1,2-N,N'-dioleylcarbamyl-3-dimethylaminopropane or "DOcarbDAP", 2,3-Dilinoleoyloxy-N,N-dimethylpropylamine or "DLinDAP", 1,2-N,N'-Dilinoleylcarbamyl-3-dimethylaminopropane or "DLincarbDAP", 1,2-Dilinoleoylcarbamyl-3-dimethylaminopropane or "DLinCDAP", 2,2-dilinoleyl-4-dimethylaminomethyl-[1,3]-dioxolane or "DLin-K-DMA", 2,2-dilinoleyl-4-dimethylaminoethyl-[1,3]-dioxolane or "DLin-K-XTC2-DMA", or mixtures thereof. (Heyes, J., et al., J Controlled Release 107: 276-287 (2005); Morrissey, D V., et al., Nat. Biotechnol. 23(8): 1003-1007 (2005); PCT Publication WO2005/121348A1). The use of cholesterol-based cationic lipids to formulate the compositions (e.g., lipid nanoparticles) is also contemplated by the present invention. Such cholesterol-based cationic lipids can be used, either alone or in combination with other cationic or non-cationic lipids. Suitable cholesterol-based cationic lipids include, for example, DC-Chol (N,N-dimethyl-N-ethylcarboxamidocholesterol), 1,4-bis(3-N-oleylamino-propyl)piperazine (Gao, et al. Biochem. Biophys. Res. Comm. 179, 280 (1991); Wolf et al. BioTechniques 23, 139 (1997); U.S. Pat. No. 5,744,335).

Also contemplated are cationic lipids such as the dialkylamino-based, imidazole-based, and guanidinium-based lipids. For example, also contemplated is the use of the cationic lipid (3S,10R,13R,17R)-10,13-dimethyl-17-((R)-6-methylheptan-2-yl)-2, 3, 4, 7, 8, 9, 10, 11, 12, 13, 14, 15, 16, 17-tetradecahydro-1H-cyclopenta[a]phenanthren-3-yl 3-(1H-imidazol-4-yl)propanoate or "ICE", as disclosed in International Application No. PCT/US2010/058457, incorporated herein by reference.

The use and inclusion of polyethylene glycol (PEG)-modified phospholipids and derivatized lipids such as derivatized ceramides (PEG-CER), including N-Octanoyl-Sphingosine-1-[Succinyl(Methoxy Polyethylene Glycol)-2000] (C8 PEG-2000 ceramide) in the liposomal and pharmaceutical compositions described herein is also contemplated, preferably in combination with one or more of the compounds and lipids disclosed herein. Contemplated PEG-modified lipids include, but are not limited to, a polyethylene glycol chain of up to 5 kDa in length covalently attached to a lipid with alkyl chain(s) of $C_6$-$C_{20}$ length. In some embodiments, the PEG-modified lipid employed in the compositions and methods of the invention is 1,2-dimyristoyl-sn-glycerol, methoxypolyethylene Glycol (2000 MW PEG) "DMG-PEG2000." The addition of PEG-modified lipids to the lipid delivery vehicle may prevent complex aggregation and may also provide a means for increasing circulation lifetime and increasing the delivery of the lipid-polynucleotide composition to the target tissues, (Klibanov et al. (1990) FEBS Letters, 268 (1): 235-237), or they may be selected to rapidly exchange out of the formulation in vivo (see U.S. Pat. No. 5,885,613). Particularly useful exchangeable lipids are PEG-ceramides having shorter acyl chains (e.g., C14 or C18). The PEG-modified phospholipid and derivitized lipids of the present invention may comprise a molar ratio from about 0% to about 20%, about 0.5% to about 20%, about 1% to about 15%, about 4% to about 10%, or about 2% of the total lipid present in a liposomal lipid nanoparticle.

The present invention also contemplates the use of non-cationic lipids in one or more of the pharmaceutical or liposomal compositions (e.g., lipid nanoparticles). Such non-cationic lipids are preferably used in combination with one or more of the compounds and lipids disclosed herein. As used herein, the phrase "non-cationic lipid" refers to any neutral, zwitterionic or anionic lipid. As used herein, the phrase "anionic lipid" refers to any of a number of lipid species that carry a net negative charge at a selected pH, such as physiological pH. Non-cationic lipids include, but are not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoyl-phosphatidylcholine (POPC), palmitoyloleoyl-phosphatidylethanolamine (POPE), dioleoylphosphatidylethanolamine 4-(N-maleimidomethyp-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), DLPE (1,2-dilauroyl-sn-glycero-3-phosphoethanolamine), DPPS (1,2-dipalmitoyl-sn-glycero-3-phospho-L-serine), 16-O-monomethyl PE, 16-O-dimethyl PE, 18-1-trans PE, 1-stearoyl-2-oleoyl-phosphatidyethanolamine (SOPE), ceramides, sphingomyelins, cholesterol, or a mixture thereof. Such non-cationic lipids may be used alone, but are preferably used in combination with other excipients, for example, one or more of the cationic lipid compounds disclosed herein (e.g., HGT4001, HGT4002, HGT4003, HGT4004 and/or HGT4005). When used in combination with a cationic lipid, the non-cationic lipid may comprise a molar ratio of 5% to about 90%, or preferably about 10% to about 70% of the total lipid present in the lipid nanoparticle.

Also contemplated is inclusion of polymers in the lipid nanoparticles that comprise the pharmaceutical or liposomal compositions described herein. Suitable polymers may include, for example, polyacrylates, polyalkycyanoacrylates, polylactide, polylactide-polyglycolide copolymers, polycaprolactones, dextran, albumin, gelatin, alginate, collagen, chitosan, cyclodextrins and polyethylenimine. Such polymers may be used alone, but are preferably used in combination with other excipients, for example, one or more of the cationic lipid compounds disclosed herein (e.g., HGT4001, HGT4002, HGT4003, HGT4004 and/or HGT4005).

In certain embodiments, the pharmaceutical and liposomal compositions (e.g., lipid nanoparticles) are formulated based in part upon their ability to facilitate the transfection (e.g., of a polynucleotide) of a target cell. In another embodiment, the pharmaceutical and liposomal compositions (e.g., lipid nanoparticles) may be selected and/or prepared to optimize delivery of polynucleotides to a target cell, tissue or organ. For example, if the target cell is a hepatocyte the properties of the pharmaceutical and/or liposomal compositions (e.g., size, charge and/or pH) may be optimized to effectively deliver such composition (e.g., lipid nanoparticles) to the target cell or organ, reduce immune clearance and/or promote retention in that target organ. Alternatively, if the target tissue is the central nervous system the selection and preparation of the pharmaceutical and liposomal compositions must consider penetration of, and retention within the blood brain barrier and/or the use of alternate means of directly delivering such compositions (e.g., lipid nanoparticles) to such target tissue (e.g., via intracerebrovascular administration). In certain embodiments, the pharmaceutical or liposomal compositions or their constituent lipid nanoparticles may be combined with agents that facilitate the transfer of encapsulated materials (e.g., agents which disrupt or improve the permeability of the blood brain barrier and thereby enhance the transfer of such encapsulated polynucleotides to the target cells). While the pharmaceutical and liposomal compositions described herein (e.g lipid nanoparticles) can facilitate introduction of encapsulated materials such as one or more polynucleotides into target cells, the addition of polycations (e.g., poly L-lysine and protamine) to, for example one or more of the lipid nanoparticles that comprise the pharmaceutical compositions as a copolymer can also facilitate, and in some instances markedly enhance the transfection efficiency of several types of cationic liposomes by 2-28 fold in a number of cell lines both in vitro and in vivo. (See, N. J. Caplen, et al., Gene Ther. 1995; 2: 603; S. Li, et al., Gene Ther. 1997; 4, 891.)

In certain embodiments of the present invention, the pharmaceutical and liposomal compositions (e.g., lipid nanoparticles) are prepared to encapsulate one or more materials or therapeutic agents (e.g., polynucleotides). The process of incorporating a desired therapeutic agent (e.g., mRNA) into a liposome or a lipid nanoparticle is referred to herein as or "loading" or "encapsulating" (Lasic, et al., FEBS Lett., 312: 255-258, 1992). The lipid nanoparticle-loaded or -encapsulated materials (e.g., polynucleotides) may be completely or partially located in the interior space of the lipid nanoparticle, within the bilayer membrane of the lipid nanoparticle, or associated with the exterior surface of the lipid nanoparticle.

Loading or encapsulating, for example, a polynucleotide into a lipid nanoparticle may serve to protect the polynucleotide from an environment which may contain enzymes or chemicals (e.g., serum) that degrade such polynucleotides and/or systems or receptors that cause the rapid excretion of such polynucleotides. Accordingly, in some embodiments, the compositions described herein are capable of enhancing the stability of the polynucleotide(s) encapsulated thereby, particularly with respect to the environments into which such polynucleotides will be exposed. Encapsulating materials, such as for example polynucleotides into one or more of the pharmaceutical and liposomal compositions described herein (e.g., lipid nanoparticles) also facilitates the delivery of such polynucleotides into the target cells and tissues. For example, lipid nanoparticles comprising one or more of the lipid compounds described herein can allow the encapsulated polynucleotide to reach the target cell or may preferentially allow the encapsulated polynucleotide to reach the target cells or organs on a discriminatory basis (e.g., the lipid nanoparticles may concentrate in the liver or spleens of a subject to which such lipid nanoparticles are administered). Alternatively, the lipid nanoparticles may limit the delivery of encapsulated polynucleotides to other non-targeted cells or organs where the presence of the encapsulated polynucleotides may be undesirable or of limited utility.

In certain embodiments, the pharmaceutical and liposomal compositions described herein (e.g., lipid nanoparticles) are prepared by combining multiple lipid components (e.g., one or more of the compounds disclosed herein) with one or more polymer components. For example, a lipid nanoparticle may be prepared using HGT4003, DOPE, CHOL and DMG-PEG2000. A lipid nanoparticle may be comprised of additional lipid combinations in various ratios, including for example, HGT4001, DOPE and DMG-PEG2000. The selection of cationic lipids, non-cationic lipids and/or PEG-modified lipids which comprise the lipid nanoparticles, as well as the relative molar ratio of such lipids to each other, is based upon the characteristics of the selected lipid(s), the nature of the intended target cells or tissues and the characteristics of the materials or polynucleotides to be delivered by the lipid nanoparticle. Additional considerations include, for example, the saturation of the alkyl chain, as well as the size, charge, pH, pKa, fusogenicity and toxicity of the selected lipid(s).

The pharmaceutical and liposomal composition (e.g., lipid nanoparticles) for use in the present invention can be prepared by various techniques which are presently known in the art. Multi-lamellar vesicles (MLV) may be prepared conventional techniques, for example, by depositing a selected lipid on the inside wall of a suitable container or vessel by dissolving the lipid in an appropriate solvent, and then evaporating the solvent to leave a thin film on the inside of the vessel or by spray drying. An aqueous phase may then added to the vessel with a vortexing motion which results in the formation of MLVs. Uni-lamellar vesicles (ULV) can then be formed by homogenization, sonication or extrusion of the multi-lamellar vesicles. In addition, unilamellar vesicles can be formed by detergent removal techniques.

In certain embodiments, the pharmaceutical and liposomal compositions of the present invention comprise a lipid nanoparticle wherein the encapsulated polynucleotide (e.g., mRNA) is associated on both the surface of the lipid nanoparticle and encapsulated within the same lipid nanoparticle. For example, during preparation of the compositions of the present invention, one or more of the cationic lipid compounds described herein and which comprise the lipid nanoparticles may associate with the polynucleotides (e.g., mRNA) through electrostatic interactions with such polynucleotides.

In certain embodiments, the pharmaceutical and liposomal compositions of the present invention may be loaded with diagnostic radionuclide, fluorescent materials or other materials that are detectable in both in vitro and in vivo applications. For example, suitable diagnostic materials for use in the present invention may include Rhodamine-dioleoylphosphatidylethanolamine (Rh-PE), Green Fluorescent Protein mRNA (GFP mRNA), *Renilla* Luciferase mRNA and Firefly Luciferase mRNA (SEQ ID NO: 1).

During the preparation of liposomal compositions described herein, water soluble carrier agents may be also encapsulated in the aqueous interior by including them in the hydrating solution, and lipophilic molecules may be incorporated into the lipid bilayer by inclusion in the lipid formulation. In the case of certain molecules (e.g., cationic or anionic lipophilic polynucleotides), loading of the polynucleotide into preformed lipid nanoparticles or liposomes may be accomplished, for example, by the methods described in U.S. Pat. No. 4,946,683, the disclosure of which is incorporated herein by reference. Following encapsulation of the polynucleotide, the lipid nanoparticles may be processed to remove un-encapsulated mRNA through processes such as gel chromatography, diafiltration or ultrafiltration. For example, if it is desirous to remove externally bound polynucleotide from the surface of the liposomal compositions (e.g., lipid nanoparticles) described herein, such lipid nanoparticles may be subject to a Diethylaminoethyl SEPHACEL column.

In addition to the encapsulated materials (e.g., polynucleotides or one or more therapeutic or diagnostic agents) may be included or encapsulated in the lipid nanoparticle. For example, such additional therapeutic agents may be associated with the surface of the lipid nanoparticle, can be incorporated into the lipid bilayer of the lipid nanoparticle by inclusion in the lipid formulation or loading into preformed lipid nanoparticles (See, U.S. Pat. Nos. 5,194,654 and 5,223,263, which are incorporated by reference herein).

There are several methods for reducing the the size, or "sizing", of the liposomal compositions (e.g., lipid nanoparticles) disclosed herein, and any of these methods may generally be employed when sizing is used as part of the invention. The extrusion method is a one method of liposome sizing. (Hope, M J et al. Reduction of Liposome Size and Preparation of Unilamellar Vesicles by Extrusion Techniques. In: *Liposome Technology* (G. Gregoriadis, Ed.) Vol. 1. p 123 (1993)). The method consists of extruding liposomes through a small-pore polycarbonate membrane or an asymmetric ceramic membrane to reduce liposome sizes to a relatively well-defined size distribution. Typically, the suspension is cycled through the membrane one or more times until the desired liposome size distribution is achieved. The liposomes may be extruded through successively smaller pore membranes to achieve gradual reduction in liposome size.

A variety of alternative methods known in the art are available for sizing of a population of lipid nanoparticles. One such sizing method is described in U.S. Pat. No. 4,737,323, incorporated herein by reference. Sonicating a liposome or lipid nanoparticle suspension either by bath or probe sonication produces a progressive size reduction down to small ULV less than about 0.05 microns in diameter. Homogenization is another method that relies on shearing energy to fragment large liposomes into smaller ones. In a typical homogenization procedure, MLV are recirculated through a standard emulsion homogenizer until selected liposome sizes, typically between about 0.1 and 0.5 microns, are observed. The size of the lipid nanoparticles may be determined by quasi-electric light scattering (QELS) as described in Bloomfield, Ann. Rev. Biophys. Bioeng., 10:421-450 (1981), incorporated herein by reference. Average lipid nanoparticle diameter may be reduced by sonication of formed lipid nanoparticles. Intermittent sonication cycles may be alternated with QELS assessment to guide efficient liposome synthesis.

Selection of the appropriate size of the liposomal compositions described herein (e.g., lipid nanoparticles) must take into consideration the site of the target cell or tissue and to some extent the application for which the lipid nanoparticle is being made. As used herein, the phrase "target cell" refers to cells to which one or more of the pharmaceutical and liposomal compositions described herein are to be directed or targeted. In some embodiments, the target cells comprise a particular tissue or organ. In some embodiments, the target cells are deficient in a protein or enzyme of interest. For example, where it is desired to deliver a polynucleotide to a hepatocyte, the hepatocyte represents the target cell. In some embodiments, the pharmaceutical or liposomal compositions (and for example the polynucleotide materials encapsulated therein) of the present invention transfect the target cells on a discriminatory basis (i.e., do not transfect non-target cells). The compositions and methods of the present invention may be prepared to preferentially target a variety of target cells, which include, but are not limited to, hepatocytes, epithelial cells, hematopoietic cells, epithelial cells, endothelial cells, lung cells, bone cells, stem cells, mesenchymal cells, neural cells (e.g., meninges, astrocytes, motor neurons, cells of the dorsal root ganglia and anterior horn motor neurons), photoreceptor cells (e.g., rods and cones), retinal pigmented epithelial cells, secretory cells, cardiac cells, adipocytes, vascular smooth muscle cells, cardiomyocytes, skeletal muscle cells, beta cells, pituitary cells, synovial lining cells, ovarian cells, testicular cells, fibroblasts, B cells, T cells, reticulocytes, leukocytes, granulocytes and tumor cells.

Following transfection of one or more target cells by, for example, the polynucleotides encapsulated in the one or more lipid nanoparticles comprising the pharmaceutical or liposomal compositions disclosed herein, the production of the product (e.g., a polypeptide or protein) encoded by such polynucleotide may be preferably stimulated and the capability of such target cells to express the polynucleotide and produce, for example, a polypeptide or protein of interest is enhanced. For example, transfection of a target cell by one or more compounds or pharmaceutical compositions encapsulating mRNA will enhance (i.e., increase) the production of the protein or enzyme encoded by such mRNA.

In some embodiments, it may be desirable to limit transfection of the polynucleotides to certain cells or tissues. For example, the liver represents an important target organ for the compositions of the present invention in part due to its central role in metabolism and production of proteins and accordingly diseases which are caused by defects in liver-specific gene products (e.g., the urea cycle disorders) may benefit from specific targeting of cells (e.g., hepatocytes). Accordingly, in certain embodiments of the present invention, the structural characteristics of the target tissue may be exploited to direct the distribution of the pharmaceutical and liposomal compositions of the present invention (e.g., an HGT4001-based lipid nanoparticle) to such target tissues. For example, to target hepatocytes one or more of the lipid nanoparticles that comprise the pharmaceutical or liposomal compositions described herein may be sized such that their dimensions are smaller than the fenestrations of the endothelial layer lining hepatic sinusoids in the liver; accordingly the one or more of such lipid nanoparticles can readily penetrate such endothelial fenestrations to reach the target hepatocytes. Alternatively, a lipid nanoparticle may be sized such that the dimensions of the liposome are of a sufficient diameter to limit or expressly avoid distribution into certain cells or tissues. For example, lipid nanoparticles that comprise the pharmaceutical and liposomal compositions described herein may be sized such that their dimensions are larger than the fenestrations of the endothelial layer lining hepatic sinusoids to thereby limit distribution of the liposomal lipid nanoparticle to hepatocytes. In such an embodiment, large liposomal compositions (e.g., lipid nanoparticles) will not easily penetrate the endothelial fenestrations, and would instead be cleared by the macrophage Kupffer cells that line the liver sinusoids. Sizing of, for example, the lipid nanoparticles comprising the pharmaceutical composition may therefore provide an opportunity to further manipulate and precisely control the degree to which expression of the encapsulated polynucleotides may be enhanced in one or more target cells. Generally, the size of at least one of the lipid nanoparticles that comprise the pharmaceutical and liposomal compositions of the present invention is within the range of about 25 to 250 nm, preferably less than about 250 nm, 175 nm, 150 nm, 125 nm, 100 nm, 75 nm, 50 nm, 25 nm or 10 nm.

Similarly, the compositions of the present invention may be prepared to preferentially distribute to other target tissues, cells or organs, such as the heart, lungs, kidneys, spleen. For example, the lipid nanoparticles of the present invention may be prepared to achieve enhanced delivery to the target cells and tissues. Accordingly, the compositions of the present invention may be enriched with additional cationic, non-cationic and PEG-modified lipids to further target tissues or cells.

In some embodiments, the compounds and the pharmaceutical and liposomal compositions described herein (e.g., HGT4002-based lipid nanoparticles) distribute to the cells and tissues of the liver to enhance the delivery, transfection and the subsequent expression of the polynucleotides (e.g., mRNA) encapsulated therein by the cells and tissues of the liver (e.g., hepatocytes) and the corresponding production of the polypeptide or protein encoded by such polynucleotide. While such compositions may preferentially distribute into the cells and tissues of the liver, the therapeutic effects of the expressed polynucleotides and the subsequent production of a protein encoded thereby need not be limited to the target cells and tissues. For example, the targeted hepatocytes may function as a "reservoir" or "depot" capable of expressing or producing, and systemically or peripherally excreting a functional protein or enzyme, as disclosed for example, in International Application No. PCT/US2010/058457 and in U.S. Provisional Application No. 61/494,881, the teachings of which are both incorporated by reference in their entirety. Accordingly, in certain embodiments of the present invention the one or more of the lipid nanoparticles that comprise the pharmaceutical and liposomal compositions described herein (e.g., HGT4005-based lipid nanoparticles) may target hepatocytes and/or preferentially distribute to the cells and tissues of the liver upon delivery. Following the transfection of the target hepatocytes by the polynucleotide encapsulated in one or more of such lipid nanoparticles, such polynucleotides are expressed (e.g., translated) and a functional product (e.g., a polypeptide or protein) is excreted and systemically distributed, where such functional product may exert a desired therapeutic effect.

The polynucleotides encapsulated in one or more of the compounds or pharmaceutical and liposomal compositions described herein can be delivered to and/or transfect targeted cells or tissues. In some embodiments, the encapsulated polynucleotides are capable of being expressed and functional polypeptide products produced (and in some instances excreted) by the target cell, thereby conferring a beneficial property to, for example the target cells or tissues. Such encapsulated polynucleotides may encode, for example, a hormone, enzyme, receptor, polypeptide, peptide or other protein of interest. In certain embodiments, such encapsulated polynucleotides may also encode a small interfering RNA (siRNA) or antisense RNA for the purpose of modulating or otherwise decreasing or eliminating the expression of an endogenous nucleic acid or gene. In certain embodiments such encapsulated polynucleotides may be natural or recombinant in nature and may exert their therapeutic activity using either sense or antisense mechanisms of action (e.g., by modulating the expression of a target gene or nucleic acid).

In some embodiments, the encapsulated polynucleotides (e.g., mRNA encoding a deficient protein) may optionally include chemical or biological modifications which, for example, improves the stability and/or half-life of such polynucleotide or which improves or otherwise facilitates translation of such polynucleotide.

Also contemplated by the present invention is the co-delivery of one or more unique polynucleotides to target cells by the compounds or pharmaceutical and liposomal compositions described herein, for example, by combining two unique therapeutic agents or polynucleotides into a single lipid nanoparticle. Also contemplated is the delivery of one or more encapsulated polynucleotides to one or more target cells to treat a single disorder or deficiency, wherein each such polynucleotide functions by a different mechanism of action. For example, the pharmaceutical or liposomal compositions of the present invention may comprise a first polynucleotide which, for example, is encapsulated in a lipid nanoparticle and intended to correct an endogenous protein or enzyme deficiency, and a second polynucleotide intended to deactivate or "knock-down" a malfunctioning endogenous polynucleotide and its protein or enzyme product. Such encapsulated polynucleotides may encode, for example mRNA and siRNA.

While in vitro transcribed polynucleotides (e.g., mRNA) may be transfected into target cells, such polynucleotides may be readily and efficiently degraded by the cell in vivo, thus rendering such polynucleotides ineffective. Moreover, some polynucleotides are unstable in bodily fluids (particularly human serum) and can be degraded or digested even before reaching a target cell. In addition, within a cell, a natural mRNA can decay with a half-life of between 30 minutes and several days. Accordingly, in certain embodiments, the encapsulated polynucleotides provided herein, and in particular the mRNA polynucleotides provided herein, preferably retain at least some ability to be expressed or translated, to thereby produce a functional protein or enzyme within one or more target cells.

In certain embodiments, the pharmaceutical and liposomal compositions comprise one or more of the lipid compounds disclosed herein and one or more lipid nanoparticles that include or encapsulate one or more stabilized polynucleotides (e.g., mRNA which has been stabilized against in vivo nuclease digestion or degradation) that modulate the expression of a gene or that may be expressed or translated to produce a functional polypeptide or protein within one or more target cells. In certain embodiments, the activity of such encapsulated polynucleotides (e.g., mRNA encoding a functional protein or enzyme) is prolonged over an extended period of time. For example, the activity of the polynucleotides may be prolonged such that the pharmaceutical compositions may be administered to a subject on a semi-weekly or bi-weekly basis, or more preferably on a monthly, bi-monthly, quarterly or an annual basis. The extended or prolonged activity of the pharmaceutical compositions of the present invention, and in particular of the encapsulated mRNA, is directly related to the quantity of functional protein or enzyme translated from such mRNA. Similarly, the activity of the compositions of the present invention may be further extended or prolonged by chemical modifications made to further improve or enhance translation of the mRNA polynucleotides. For example, the Kozac consensus sequence plays a role in the initiation of protein translation, and the inclusion of such a Kozac consensus sequence in the encapsulated mRNA polynucleotides may further extend or prolong the activity of the mRNA polynucleotides. Furthermore, the quantity of functional protein or enzyme produced by the target cell is a function of the quantity of polynucleotide (e.g., mRNA) delivered to the target cells and the stability of such polynucleotide. To the extent that the stability of the polynucleotides encapsulated by the compounds or compositions of the present invention may be improved or enhanced, the half-life, the activity of the translated protein or enzyme and the dosing frequency of the composition may be further extended.

In certain embodiments the polynucleotides can be chemically modified for example, to confer stability (e.g., stability relative to the wild-type or naturally-occurring version of the mRNA and/or the version of the mRNA naturally endogenous to target cells). Accordingly, in some embodiments, the encapsulated polynucleotides provided herein comprise at least one chemical modification which confers increased or enhanced stability to the polynucleotide, including, for example, improved resistance to nuclease digestion in vivo. As used herein, the phrases "chemical modifications" and "chemically modified" as such terms relate to the polynucleotides provided herein, include at least one alteration which preferably enhances stability and renders the polynucleotide more stable (e.g., resistant to nuclease digestion) than the wild-type or naturally occurring version of that polynucleotide. The terms "stable" and "stability" as such terms relate to the polynucleotides encapsulated by the compounds or pharmaceutical and liposomal compositions of the present invention, and particularly with respect to the mRNA, refer to increased or enhanced resistance to degradation by, for example nucleases (i.e., endonucleases or exonucleases) which are normally capable of degrading such RNA. Increased stability can include, for example, less sensitivity to hydrolysis or other destruction by endogenous enzymes (e.g., endonucleases or exonucleases) or conditions within the target cell or tissue, thereby increasing or enhancing the residence of such polynucleotides in the target cell, tissue, subject and/or cytoplasm. The stabilized polynucleotide molecules provided herein demonstrate longer half-lives relative to their naturally occurring, unmodified counterparts (e.g. the wild-type version of the polynucleotide).

Also contemplated by the phrases "chemical modification" and "chemically modified" as such terms related to the polynucleotides encapsulated by the compounds or pharmaceutical and liposomal compositions of the present invention are alterations which improve or enhance translation of mRNA polynucleotides, including for example, the inclusion of sequences which function in the initiation of protein translation (e.g., the Kozac consensus sequence). (Kozak, M., Nucleic Acids Res 15 (20): 8125-48 (1987)). The phrase "chemical modifications" as used herein, also include modifications which introduce chemistries which differ from those seen in naturally occurring polynucleotides, for example, covalent modifications such as the introduction of modified nucleotides, (e.g., nucleotide analogs, or the inclusion of pendant groups which are not naturally found in such polynucleotide molecules). In some embodiments, the polynucleotides have undergone a chemical or biological modification to render them more stable prior to encapsulation in one or more lipid nanoparticles. Exemplary chemical modifications to a polynucleotide include the depletion of a base (e.g., by deletion or by the substitution of one nucleotide for another) or chemical modification of a base.

In addition, suitable modifications include alterations in one or more nucleotides of a codon such that the codon encodes the same amino acid but is more stable than the codon found in the wild-type version of the polynucleotide. For example, an inverse relationship between the stability of RNA and a higher number cytidines (C's) and/or uridines (U's) residues has been demonstrated, and RNA devoid of C and U residues have been found to be stable to most RNases (Heidenreich, et al. J Biol Chem 269, 2131-8 (1994)). In some embodiments, the number of C and/or U residues in an mRNA sequence is reduced. In a another embodiment, the number of C and/or U residues is reduced by substitution of one codon encoding a particular amino acid for another codon encoding the same or a related amino acid. Contemplated modifications to the mRNA polynucleotides encapsulated by the compounds or pharmaceutical and liposomal compositions of the present invention also include the incorporation of pseudouridines. The incorporation of pseudouridines into the mRNA polynucleotides encapsulated by the compounds or pharmaceutical and liposomal compositions of the present invention may enhance stability and translational capacity, as well as diminishing immunogenicity in vivo. (See, e.g., Karikó, K., et al., Molecular Therapy 16 (11): 1833-1840 (2008)). Substitutions and modifications to the polynucleotides encapsulated by the compounds or pharmaceutical and liposomal compositions of the present invention may be performed by methods readily known to one or ordinary skill in the art.

The constraints on reducing the number of C and U residues in a sequence will likely be greater within the coding region of an mRNA, compared to an untranslated region, (i.e., it will likely not be possible to eliminate all of the C and U residues present in the message while still retaining the ability of the message to encode the desired amino acid sequence). The degeneracy of the genetic code, however presents an opportunity to allow the number of C and/or U residues that are present in the sequence to be reduced, while maintaining the same coding capacity (i.e., depending on which amino acid is encoded by a codon, several different possibilities for modification of RNA sequences may be possible). For example, the codons for Gly can be altered to GGA or GGG instead of GGU or GGC.

The term chemical modification also includes, for example, the incorporation of non-nucleotide linkages or modified nucleotides into the polynucleotide sequences of the present invention (e.g., end-blocking modifications to one or both the 3' and 5' ends of an mRNA molecule encoding a functional protein or enzyme). Such modifications may include the addition of bases to a polynucleotide sequence (e.g., the inclusion of a poly A tail or a longer poly A tail), the alteration of the 3' UTR or the 5' UTR, complexing the polynucleotide with an agent (e.g., a protein or a complementary polynucleotide molecule), and inclusion of elements which change the structure of a polynucleotide molecule (e.g., which form secondary structures).

The poly A tail is thought to stabilize natural messengers and synthetic sense RNA. Therefore, in certain embodiments a long poly A tail can be added to an mRNA molecule thus rendering the RNA more stable. Poly A tails can be added using a variety of art-recognized techniques. For example, long poly A tails can be added to synthetic or in vitro transcribed RNA using poly A polymerase (Yokoe, et al. Nature Biotechnology. 1996; 14: 1252-1256). A transcription vector can also encode long poly A tails. In addition, poly A tails can be added by transcription directly from PCR products. Poly A may also be ligated to the 3' end of a sense RNA with RNA ligase (see, e.g., Molecular Cloning A Laboratory Manual, 2nd Ed., ed. by Sambrook, Fritsch and Maniatis (Cold Spring Harbor Laboratory Press: 1991 edition)). In certain embodiments, the length of the poly A tail is at least about 90, 200, 300, 400 at least 500 nucleotides. In certain embodiments, the length of the poly A tail is adjusted to control the stability of a modified sense mRNA molecule of the invention and, thus, the transcription of protein. For example, since the length of the poly A tail can influence the half-life of a sense mRNA molecule, the length of the poly A tail can be adjusted to modify the level of resistance of the mRNA to nucleases and thereby control the time course of polynucleotide expression and protein production in a target cell. In certain embodiments, the stabilized polynucleotide molecules are sufficiently resistant to in vivo degradation (e.g., by nucleases), such that they may be delivered to the target cell without a lipid nanoparticle.

In certain embodiments, the chemical modifications are end-blocking modification of the one or more polynucleotides which comprise the pharmaceutical compositions of the invention. For example, such polynucleotides can be modified by the incorporation 3' and/or 5' untranslated (UTR) sequences which are not naturally found in the wild-type polynucleotide. In certain embodiments, 3' and/or 5' flanking sequence which naturally flanks an mRNA and encodes a second, unrelated protein can be incorporated into the nucleotide sequence of an mRNA molecule encoding a or functional protein in order to modify it. For example, 3' or 5' sequences from mRNA molecules which are stable (e.g., globin, actin, GAPDH, tubulin, histone, or citric acid cycle enzymes) can be incorporated into the 3' and/or 5' region of a sense mRNA polynucleotide molecule to increase the stability of the sense mRNA molecule.

Also contemplated by the present invention are modifications to the polynucleotide sequences made to one or both of the 3' and 5' ends of the polynucleotide. For example, the present invention contemplates modifications to the 3' and/or 5' end of the polynucleotides (e.g., mRNA) to include a partial sequence of a CMV immediate-early 1 (IE1) gene, or a fragment thereof to improve the nuclease resistance and/or improve the half-life of the polynucleotide (such as, e.g., SEQ ID NO:1). In addition to increasing the stability of the mRNA polynucleotide sequence, it has been surprisingly discovered the inclusion of a partial sequence of a CMV immediate-early 1 (IE1) gene (e.g., to one or more of the 5' untranslated region and 3' untranslated region of the mRNA) further enhances the translation of the mRNA. Also contemplated is the inclusion of a sequence from the human growth hormone (hGH) gene, or a fragment thereof to one or both of the 3' and 5' ends of the polynucleotide (e.g., mRNA) to further stabilize the polynucleotide (such as, e.g., SEQ ID NO:2). Generally, the contemplated chemical modifications improve the stability and/or pharmacokinetic properties (e.g., half-life) of the polynucleotide relative to their unmodified counterparts, and include, for example modifications made to improve such polynucleotides' resistance to in vivo nuclease digestion.

In some embodiments, the pharmaceutical composition, the two or more lipid nanoparticles comprised therein or the polynucleotides encapsulated by such lipid nanoparticles can comprise a stabilizing reagent. The compositions can include one or more formulation reagents that bind directly or indirectly to, and stabilize the polynucleotide, thereby enhancing residence time in the cytoplasm of a target cell. Such reagents preferably lead to an improved half-life of a polynucleotide in the target cells. For example, the stability of an mRNA and efficiency of translation may be increased by the incorporation of "stabilizing reagents" that form complexes with the polynucleotides (e.g., mRNA) that naturally occur within a cell (see e.g., U.S. Pat. No. 5,677,124). Incorporation of a stabilizing reagent can be accomplished for example, by combining the poly A and a protein with the mRNA to be stabilized in vitro before loading or encapsulating the mRNA within the one or more lipid nanoparticles that comprise the pharmaceutical composition. Exemplary stabilizing reagents include one or more proteins, peptides, aptamers, translational accessory protein, mRNA binding proteins, and/or translation initiation factors.

Stabilization of the pharmaceutical and liposomal compositions described herein (e.g., lipid nanoparticles) may also be improved by the use of opsonization-inhibiting moieties, which are typically large hydrophilic polymers that are chemically or physically bound or otherwise incorporated into the lipid nanoparticle (e.g., by the intercalation of a lipid-soluble anchor into the membrane itself, or by binding directly to active groups of membrane lipids). These opsonization-inhibiting hydrophilic polymers form a protective surface layer which significantly decreases the uptake of the liposomes by the macrophage-monocyte system and reticulo-endothelial system (e.g., as described in U.S. Pat. No. 4,920,016, the entire disclosure of which is herein incorporated by reference). For example, delays in the uptake of lipid nanoparticles by the reticuloendothelial system may be facilitated by the addition of a hydrophilic polymer surface coating onto or into lipid nanoparticles to mask the recognition and uptake of the liposomal-based lipid nanoparticle by the reticuloendothelial system. For example, in certain embodiments, one or more of the lipid nanoparticles that comprise the pharmaceutical compositions disclosed herein comprise a polyethyleneglycol (PEG) polymer or a PEG-modified lipid to further enhance delivery of such lipid nanoparticles to the target cell and tissues.

When RNA is hybridized to a complementary polynucleotide molecule (e.g., DNA or RNA) it may be protected from nucleases. (Krieg, et al. Melton. Methods in Enzymology. 1987; 155, 397-415). The stability of hybridized mRNA is likely due to the inherent single strand specificity of most RNases. In some embodiments, the stabilizing reagent selected to complex a polynucleotide is a eukaryotic protein, (e.g., a mammalian protein). In yet another embodiment, the polynucleotide (e.g., mRNA) for use in sense therapy can be modified by hybridization to a second polynucleotide molecule. If an entire mRNA molecule were hybridized to a complementary polynucleotide molecule translation initiation may be reduced. In some embodiments the 5' untranslated region and the AUG start region of the mRNA molecule may optionally be left unhybridized. Following translation initiation, the unwinding activity of the ribosome complex can function even on high affinity duplexes so that translation can proceed. (Liebhaber. J. Mol. Biol. 1992; 226: 2-13; Monia, et al. J Biol Chem. 1993; 268: 14514-22.) It will be understood that any of the above described methods for enhancing the stability of polynucleotides may be used either alone or in combination with one or more of any of the other above-described methods and/or compositions.

In certain embodiments, the pharmaceutical compositions of the present invention enhance the delivery of lipid nanoparticle-encapsulated polynucleotides to one or more target cells, tissues or organs. In some embodiments, enhanced delivery to one or more target cells comprises increasing the amount of polynucleotide that comes in contact or is otherwise delivered to the target cells. In some embodiments, enhancing delivery to target cells comprises reducing the amount of polynucleotide that comes into contact with non-target cells. In some embodiments, enhancing delivery to target cells comprises allowing the transfection of at least some target cells with the encapsulated polynucleotide. In some embodiments, the level of expression of the polynucleotide encapsulated by the lipid nanoparticles which comprise the subject pharmaceutical compositions and the corresponding production of the functional protein or enzyme encoded thereby is increased in the target cells.

The polynucleotides encapsulated by the compounds or pharmaceutical and liposomal compositions of the present invention may be optionally combined with a reporter gene (e.g., upstream or downstream of the coding region of the polynucleotide) which, for example, facilitates the determination of polynucleotide delivery to the target cells or tissues. Suitable reporter genes may include, for example, Green Fluorescent Protein mRNA (GFP mRNA), *Renilla* Luciferase mRNA (Luciferase mRNA), Firefly Luciferase mRNA (SEQ ID NO: 1), or any combinations thereof. For example, GFP mRNA may be fused with a polynucleotide encoding OTC mRNA to facilitate confirmation of mRNA localization in the target cells, tissues or organs.

In some embodiments, the pharmaceutical compositions of the present invention comprise one or more additional molecules (e.g., proteins, peptides, aptamers or oliogonucleotides) which facilitate the transfer of the polynucleotides (e.g., mRNA, miRNA, snRNA and snoRNA) from the lipid nanoparticle into an intracellular compartment of the target cell. In some embodiments, the additional molecule facilitates the delivery of the polynucleotides into, for example, the cytosol, the lysosome, the mitochondrion, the nucleus, the nucleolae or the proteasome of a target cell. Also included are agents that facilitate the transport of the translated protein of interest from the cytoplasm to its normal intercellular location (e.g., in the mitochondrion) to treat deficiencies in that organelle. In some embodiments, the agent is selected from the group consisting of a protein, a peptide, an aptamer, and an oligonucleotide.

In some embodiments, the compositions of the present invention facilitate a subject's endogenous production of one or more functional proteins and/or enzymes, and in particular the production of proteins and/or enzymes which demonstrate less immunogenicity relative to their recombinantly-prepared counterparts. In a certain embodiments of the present invention, the lipid nanoparticles comprise polynucleotides which encode mRNA of a deficient protein or enzyme. Upon distribution of such compositions to the target tissues and the subsequent transfection of such target cells, the exogenous mRNA loaded or encapsulated into the lipid nanoparticles that comprise the compositions may be translated in vivo to produce a functional protein or enzyme encoded by such encapsulated mRNA (e.g., a protein or enzyme in which the subject is deficient). Accordingly, in certain embodiments the compositions of the present invention exploit a subject's ability to translate exogenously- or recombinantly-prepared mRNA to produce an endogenously-translated protein or enzyme, and thereby produce (and where applicable excrete) a functional protein or enzyme. The translated proteins or enzymes may also be characterized by the in vivo inclusion of native post-translational modifications which may often be absent in recombinantly-prepared proteins or enzymes, thereby further reducing the immunogenicity of the translated protein or enzyme.

The encapsulation of mRNA in the lipid nanoparticles and the administration of the pharmaceutical compositions comprising such lipid nanoparticles avoids the need to deliver the mRNA to specific organelles within a target cell (e.g., mitochondria). Rather, upon transfection of a target cell and delivery of the encapsulated mRNA to the cytoplasm of the target cell, the mRNA contents of the lipid nanoparticles may be translated and a functional protein or enzyme produced.

The present invention also contemplates the discriminatory targeting of one or more target cells and tissues by both passive and active targeting means. The phenomenon of passive targeting exploits the natural distributions patterns of lipid nanoparticles in vivo without relying upon the use of additional excipients or means to enhance recognition of the lipid nanoparticle by one or more target cells. For example, lipid nanoparticles which are subject to phagocytosis by the cells of the reticulo-endothelial system are likely to accumulate in the liver or spleen, and accordingly may provide means to passively direct the delivery of the compositions to such target cells.

Alternatively, the present invention contemplates active targeting, which involves the use of additional excipients, referred to herein as "targeting ligands" that may be bound (either covalently or non-covalently) to the lipid nanoparticle to encourage localization of such lipid nanoparticle at certain target cells or target tissues. For example, targeting may be mediated by the inclusion of one or more endogenous targeting ligands (e.g., apolipoprotein E) in or on the lipid nanoparticle to encourage distribution to the target cells or tissues. Recognition of the targeting ligand by the target tissues actively facilitates tissue distribution to, and cellular uptake of the lipid nanoparticles and/or their contents by the target cells and tissues. For example, in certain embodiments, one or more of the lipid nanoparticles that comprise the pharmaceutical formulation may comprise an apolipoprotein-E targeting ligand in or on such lipid nanoparticles to facilitate or encourage recognition and binding of such lipid nanoparticle to endogenous low density lipoprotein receptors expressed, for example by hepatocytes. As provided herein, the composition can comprise a ligand capable of enhancing affinity of the compositions to one or more target cells. Targeting ligands may be linked to the outer bilayer of the lipid nanoparticle during formulation or post-formulation. These methods are well known in the art. In addition, some lipid nanoparticles may comprise fusogenic polymers such as PEAA, hemagluttinin, other lipopeptides (see U.S. patent application Ser. Nos. 08/835,281, and 60/083,294, which are incorporated herein by reference) and other features useful for in vivo and/or intracellular delivery. In other embodiments, the compositions of the present invention demonstrate improved transfection efficacies, and/or demonstrate enhanced selectivity towards target cells or tissues of interest. Contemplated therefore are compositions or lipid nanoparticles that comprise one or more ligands (e.g., peptides, aptamers, oligonucleotides, a vitamin or other molecules) that are capable of enhancing the affinity of the compositions or their constituent lipid nanoparticles and their polynucleotide contents to one or more target cells or tissues. Suitable ligands may optionally be bound or linked to the surface of the lipid nanoparticle. In some embodiments, the targeting ligand may span the surface of a lipid nanoparticle or be encapsulated within the lipid nanoparticle. Suitable ligands are selected based upon their physical, chemical or biological properties (e.g., selective affinity and/or recognition of target cell surface markers or features.) Cell-specific target sites and their corresponding targeting ligand can vary widely. Suitable targeting ligands are selected such that the unique characteristics of a target cell are exploited, thus allowing the composition to discriminate between target and non-target cells. For example, compositions of the present invention may bear surface markers (e.g., apolipoprotein-B or apolipoprotein-E) that selectively enhance recognition of, or affinity to hepatocytes (e.g., by receptor-mediated recognition of and binding to such surface markers). Additionally, the use of galactose as a targeting ligand would be expected to direct the compositions of the present invention to parenchymal hepatocytes, or alternatively the use of mannose containing sugar residues as a targeting ligand would be expected to direct the compositions of the present invention to liver endothelial cells (e.g., mannose containing sugar residues that may bind preferentially to the asialoglycoprotein receptor present in hepatocytes). (See Hillery A M, et al. "Drug Delivery and Targeting: For Pharmacists and Pharmaceutical Scientists" (2002) Taylor & Francis, Inc.) The presentation of such targeting ligands that have been conjugated to moieties present in the lipid nanoparticle therefore facilitate recognition and uptake of the liposomal compositions of the present invention by one or more target cells and tissues. Examples of suitable targeting ligands include one or more peptides, proteins, aptamers, vitamins and oligonucleotides.

As used herein, the term "subject" refers to any animal (e.g., a mammal), including, but not limited to, humans, non-human primates, rodents, and the like, to which the compounds, pharmaceutical or liposomal compositions and methods of the present invention may be administered. Typically, the terms "subject" and "patient" are used interchangeably herein in reference to a human subject.

The ability of the compounds and pharmaceutical or liposomal compositions described herein (e.g., lipid nanoparticles) to modulate or enhance the expression of encapsulated polynucleotides and the production of a polypeptide or protein provides novel and more efficient means of effectuating the in vivo production of polypeptides and proteins for the treatment of a host of diseases or pathological conditions. Such lipid nanoparticle compositions are particularly suitable for the treatment of diseases or pathological conditions associated with the aberrant expression of nucleic acids encoding a protein or enzyme. For example, the successful delivery of polynucleotides such as mRNA to target organs such as the liver and in particular, to hepatocytes, can be used for the treatment and the correction of in-born errors of metabolism that are localized to the liver. Accordingly, the compounds, pharmaceutical compositions and related methods described herein may be employed to treat a wide range of diseases and pathological conditions, in particular those diseases which are due to protein or enzyme deficiencies. The polynucleotides encapsulated by the compounds or pharmaceutical and liposomal compositions described herein (e.g., HGT4004-based lipid nanoparticles) may encode a functional product (e.g., a protein, enzyme, polypeptide, peptide, functional RNA, and/or antisense molecule), and preferably encodes a product whose in vivo production is desired.

The compounds, pharmaceutical compositions and related methods of the present invention are broadly applicable to the delivery of therapeutic agents such as polynucleotides, and in particular mRNA, to treat a number of disorders. In particular, such compounds, compositions and related methods of the present invention are suitable for the treatment of diseases or disorders relating to the deficiency of proteins and/or enzymes. In certain embodiments, the lipid nanoparticle-encapsulated polynucleotides encode functional proteins or enzymes that are excreted or secreted by one or more target cells into the surrounding extracellular fluid (e.g., mRNA encoding hormones and neurotransmitters). Alternatively, in another embodiment, the polynucleotides encapsulated by the compounds or pharmaceutical and liposomal compositions of the present invention encode functional proteins or enzymes that remain in the cytosol of one or more target cells (e.g., mRNA encoding an enzyme associated with urea cycle or lysosomal storage metabolic disorders). Other disorders for which the compounds, pharmaceutical compositions and related methods of the present invention are useful include, but are not limited to, disorders such as SMN1-related spinal muscular atrophy (SMA); amyotrophic lateral sclerosis (ALS); GALT-related galactosemia; Cystic Fibrosis (CF); SLC3A1-related disorders including cystinuria; COL4A5-related disorders including Alport syndrome; galactocerebrosidase deficiencies; X-linked adrenoleukodystrophy and adrenomyeloneuropathy; Huntington's Disease; Parkinson's Disease; muscular dystrophies (such as, e.g., Duchenne and Becker); hemophelia diseases, such as, e.g., hemophilia B (FIX) and Hemophilia A (FVIII); Friedreich's ataxia; Pelizaeus-Merzbacher disease; TSC1 and TSC2-related tuberous sclerosis; Sanfilippo B syndrome (MPS IIIB); CTNS-related cystinosis; the FMR1-related disorders which include Fragile X syndrome, Fragile X-Associated Tremor/Ataxia Syndrome and Fragile X Premature Ovarian Failure Syndrome; Prader-Willi syndrome; Fabry disease; hereditary hemorrhagic telangiectasia (AT); Niemann-Pick disease Type C1; the neuronal ceroid lipofuscinoses-related diseases including Juvenile Neuronal Ceroid Lipofuscinosis (JNCL), Juvenile Batten disease, Santavuori-Haltia disease, Jansky-Bielschowsky disease, and PTT-1 and TPP1 deficiencies; EIF2B1, EIF2B2, EIF2B3, EIF2B4 and EIF2B5-related childhood ataxia with central nervous system hypomyelination/vanishing white matter; CACNA1A and CACNB4-related Episodic Ataxia Type 2; the MECP2-related disorders including Classic Rett Syndrome, MECP2-related Severe Neonatal Encephalopathy and PPM-X Syndrome; CDKLS-related Atypical Rett Syndrome; Kennedy's disease (SBMA); Notch-3 related cerebral autosomal dominant arteriopathy with subcortical infarcts and leukoencephalopathy (CADASIL); SCN1A and SCN1B-related seizure disorders; the Polymerase G-related disorders which include Alpers-Huttenlocher syndrome, POLG-related sensory ataxic neuropathy, dysarthria, and ophthalmoparesis, and autosomal dominant and recessive progressive external ophthalmoplegia with mitochondrial DNA deletions; X-Linked adrenal hypoplasia; X-linked agammaglobulinemia; Wilson's disease; and Fabry Disease. In certain embodiments, the polynucleotides, and in particular mRNA, of the present invention may encode functional proteins or enzymes. For example, the compositions of the present invention may include mRNA encoding agalsidase alfa, erythropoietin, α1-antitrypsin, carboxypeptidase N, alpha-L-iduronidase, iduronate-2-sulfatase, N-acetylglucosamine-1-phosphate transferase, N-acetylglucosaminidase, alpha-glucosaminide acetyltransferase, N-acetylglucosamine 6-sulfatase, N-acetylgalactosamine-4-sulfatase, beta-glucosidase, galactose-6-sulfate sulfatase, beta-galactosidase, beta-glucuronidase, glucocerebrosidase, heparan sulfamidase, hyaluronidase, galactocerebrosidase or human growth hormone.

The compounds and pharmaceutical compositions described herein may be administered to a subject. In some embodiments, the compositions are formulated in combination with one or more additional polynucleotides, carriers, targeting ligands or stabilizing reagents or other suitable excipients. Techniques for formulation and administration of drugs may be found in "Remington's Pharmaceutical Sciences," Mack Publishing Co., Easton, Pa., latest edition.

The compounds and the pharmaceutical and liposomal compositions (e.g., lipid nanoparticles) of the present invention may be administered and dosed in accordance with current medical practice, taking into account the clinical condition of the subject, the nature of the encapsulated materials, the site and method of administration, the scheduling of administration, the subject's age, sex, body weight and other factors relevant to clinicians of ordinary skill in the art. The "effective amount" for the purposes herein may be determined by such relevant considerations as are known to those of ordinary skill in experimental clinical research, pharmacological, clinical and medical arts. In some embodiments, the amount administered is effective to achieve at least some stabilization, improvement or elimination of symptoms and other indicators as are selected as appropriate measures of disease progress, regression or improvement by those of skill in the art. For example, a suitable amount and dosing regimen is one that causes at least transient expression of the one or more polynucleotides in the target cells.

Suitable routes of administration of the compounds and pharmaceutical compositions disclosed herein include, for example, oral, rectal, vaginal, transmucosal, or intestinal administration; parenteral delivery, including intramuscular, subcutaneous, intramedullary injections, as well as intrathecal, intracerebroventricular, direct intraventricular, intravenous, intraperitoneal, intranasal, or intraocular injections or infusions. In certain embodiments, the administration of the compounds or compositions (e.g., lipid nanoparticle) described herein to a subject facilitates the contacting of such compounds or compositions to one or more target cells, tissues or organs.

Alternately, the compounds and compositions of the present invention may be administered in a local rather than systemic manner, for example, via injection or infusion of the pharmaceutical compositions directly into a targeted tissue, preferably in a depot or sustained release formulation, such that the contacting of the targeted cells with the constituent lipid nanoparticles may further facilitated. Local delivery can be affected in various ways, depending on the tissue to be targeted. For example, aerosols containing compositions of the present invention can be inhaled (for nasal, tracheal, or bronchial delivery); compositions of the present invention can be injected into the site of injury, disease manifestation, or pain, for example; compositions can be provided in lozenges for oral, tracheal, or esophageal application; can be supplied in liquid, tablet or capsule form for administration to the stomach or intestines, can be supplied in suppository form for rectal or vaginal application; or can even be delivered to the eye by use of creams, drops, or even injection. Formulations containing the compounds of the present invention complexed with therapeutic molecules or ligands can even be surgically administered, for example in association with a polymer or other structure or substance that can allow the compositions to diffuse from the site of implantation to surrounding cells. Alternatively, such compositions can be applied surgically without the use of polymers or supports.

In certain embodiments, the compositions of the present invention are formulated such that they are suitable for extended-release of the, for example, polynucleotides or nucleic acids encapsulated therein. Such extended-release compositions may be conveniently administered to a subject at extended dosing intervals. For example, in certain embodiments, the compositions of the present invention are administered to a subject twice day, daily or every other day. In a certain embodiments, the compositions of the present invention are administered to a subject twice a week, once a week, every ten days, every two weeks, every three weeks, or more preferably every four weeks, once a month, every six weeks, every eight weeks, every other month, every three months, every four months, every six months, every eight months, every nine months or annually. Also contemplated are compositions and lipid nanoparticles which are formulated for depot administration (e.g., intramuscularly, subcutaneously, intravitreally) to either deliver or release a polynucleotide (e.g., mRNA) over extended periods of time. Preferably, the extended-release means employed are combined with modifications (e.g., chemical modifications) introduced into the polynucleotides to enhance stability.

While certain compounds, compositions and methods of the present invention have been described with specificity in accordance with certain embodiments, the following examples serve only to illustrate the compounds of the invention and are not intended to limit the same. Each of the publications, reference materials and the like referenced herein to describe the background of the invention and to provide additional detail regarding its practice are hereby incorporated by reference in their entirety.

Lyophilized Lipid Delivery Vehicles

The invention provides pharmaceutical compositions that comprise lyophilized liposomal delivery vehicles and liposomal formulations that are capable of effectuating the delivery of encapsulated contents (e.g., polynucleotides) to one or more target cells, tissues or organs. Upon delivery of, for example, encapsulated polynucleotides to the one or more target cells, such polynucleotides are capable of modulating the expression (e.g., increasing the expression) of the polynucleotide or of a nucleic acid in the target cell. Also disclosed herein are related methods and processes for preparing such pharmaceutical compositions, as well as methods of treating one or more diseases or conditions by administering such pharmaceutical compositions to a subject in need thereof. The lyophilized compositions (e.g., lipid nanoparticles) described herein are also expected to have improved long-term stability upon storage under either refrigeration or at ambient temperature (e.g., room temperature) (e.g., at least one, two, three, six, nine, twelve, eighteen, twenty-four, thirty months, or longer).

As used herein to refer to the liposomal compositions (e.g., lipid nanoparticles), the terms "lyophilization" and "lyophilized" refer to a process whereby such liposomal compositions are prepared in dry from by rapid freezing and in certain instances one or more drying steps (e.g., upon exposure to vacuum conditions), thereby reducing the concentration of water in such liposomal compositions to preclude or alternatively limit further biological or chemical reactions.

Lyophilization of liposomal compositions (e.g., lipid nanoparticles) may be performed by any appropriate method, for example, as in accordance with the lyophilization cycles provided in the examples. Following the rapid freezing of the liposomal compositions (e.g., lipid nanoparticles) the liposomal compositions may be dried by one or more suitable methods, such as exposure to primary and secondary vacuum drying conditions. In some embodiments, the liposomal compositions (e.g., lipid nanoparticles) are dried in at the temperatures and vacuum conditions provided in the examples. Following exposure to the lyophilization conditions described herein, the lyophilized lipid nanoparticle compositions may be rehydrated using, for example, a suitable aqueous rehydration media (e.g., sterile water, normal saline and/or 5% dextrose) and administered to a subject.

In certain embodiments, the lyophilized pharmaceutical compositions described herein are characterized as being stable (e.g., relative to unlyophilized pharmaceutical compositions). As used to describe the lyophilized liposomal compositions described herein, the term "stable" refers to a preclusion of such liposomal compositions (e.g., lipid nanoparticles) from aggregating or flocculating (e.g., following reconstitution). The stability of such lyophilized pharmaceutical compositions may be determined with reference to a number of physical characteristics. For example, stability may be determined with reference to the particle size of the lipid nanoparticles comprising such composition. Preferably, following rehydration of the lyophilized compositions disclosed herein, the size distribution and physical characteristics of the reconstituted composition are identical or alternatively comparable to the compositions prior to lyophilization. Accordingly, in certain embodiments, lyophilization of the lipid nanoparticles does not appreciably change or alter the particle size of the lipid nanoparticles following lyophilization and/or reconstitution. For example, upon reconstitution (e.g., with purified water) the lipid nanoparticles comprising a lyophilized pharmaceutical composition do not flocculate or aggregate, or alternatively demonstrated limited or negligible flocculation or aggregation (e.g., a determined by the particle size of the reconstituted lipid nanoparticles).

In certain embodiments the reconstituted liposomal compositions (e.g., lipid nanoparticles) of the invention exhibit an enhanced (e.g., increased) ability to transfect one or more target cells. Accordingly, also provided herein are methods of transfecting one or more target cells. Such methods generally comprise the step of contacting the one or more target cells with, for example, the reconstituted lyophilized pharmaceutical compositions of the invention (e.g., a lyophilized HGT4003-based lipid nanoparticle encapsulating one or more polynucleotides) such that the one or more target cells are transfected with the materials encapsulated therein (e.g., one or more polynucleotides).

In certain embodiments, one or more lipids (e.g., cationic lipids) may be used as a liposome or alternatively as a component of a lipid delivery vehicles (e.g., lipid nanoparticle) used in the compositions of the invention. As described above, a suitable lipid delivery vehicle is a lipid nanoparticle comprising a nucleic acid, a cationic lipid, such as, e.g., the cleavable cationic lipids such as, e.g., HGT4001, HGT4002, HGT4003, HGT4004, and HGT4005 described above, or selected from the group consisting of C12-200, ICE, DOTMA, DOGS, DOSPA, DODAP, DOTAP, DSDMA, DODMA DLinDMA DLenDMA DDAB DMRIE CLinDMA CpLinDMA DMOBA DOcarbDAP DLinDAP DLincarbDAP DLinCDAP DLin-K-DMA DLin-K-XTC2-DMA, DLinKC2-DMA, HGT5000, HGT5001, HGT5002, or mixtures thereof.

Other suitable components of lipid delivery vehicles include non-cationic lipind, helper lipids, such as, e.g., cholesterol, and PEG-modified lipids as described above. For example, a lipid nanoparticle may be prepared using HGT4003, DOPE, CHOL and DMG-PEG2000. A lipid nanoparticle may be comprised of additional lipid combinations in various ratios, including for example, HGT4001, DOPE and DMG-PEG2000. The selection of cationic lipids, non-cationic lipids and/or PEG-modified lipids which comprise the lipid nanoparticles, as well as the relative molar ratio of such lipids to each other, is based upon the characteristics of the selected lipid(s), the nature of the intended target cells or tissues and the characteristics of the materials or polynucleotides to be delivered by the lipid nanoparticle. Additional considerations include, for example, the saturation of the alkyl chain, as well as the size, charge, pH, pKa, fusogenicity and toxicity of the selected lipid(s).

In one embodiment, the lyophilized lipid delivery vehicles further comprise at at least one lyoprotectant. The term "lyoprotectant" is used herein to refer to one or more compounds that, when combined with or included in the preparation of one or more of the liposomal compounds described herein, enhances (e.g., increases) the chemical and/or physical stability of the liposomal compound (e.g., a lipid nanoparticle) during the lyophilization, storage or reconstitution of such liposomal compound. For example, in certain embodiments the inclusion of one or more lyoprotectants in the lipid nanoparticle may improve or otherwise enhance the stability of the lyophilized composition (e.g., under normal storage conditions) and/or facilitate reconstitution of the lyophilized composition using a rehydration media, thereby preparing an aqueous formulation. In some embodiments the lipid nanoparticles are prepared and prior to lyophilization the buffer present in the liposomal formulation may be replaced (e.g., via centrifugation) with a suitable lyoprotectant (e.g., an aqueous sucrose solution comprising between about 1-50% or 10-25% sucrose). In some embodiments, the lyoprotectant is included as part of the buffer or media in which the liposomal formulations are prepared or lyophilized (e.g., during hydration, diafiltration, and/or dilution). Examples of suitable lyoprotectants that may be used to prepare the lyophilized compositions described herein include, for example, trehalose, dextran (e.g., 1.5 kDa, 5 kDa and/or 40 kDa), inulin (e.g., 1.8 kDa and/or 4 kDa), and any combinations thereof.

It is believed that the inclusion of a sugar lyoprotectant during lyophilization may serve to stabilize the lyophilized composition. (See, Anchordoquy, et al., *J. Pharm. Sci.* (2000) 89: 289-296.) One possible explanation for the observed stabilization may include the particle isolation hypothesis, which refers to the formation of a sugar matrix which acts as a physical barrier between the liposomal particles.

The lyophilized pharmaceutical and the component liposomes (e.g., lipid nanoparticles) for use in the present invention can be prepared by various techniques which are presently known in the art. Multi-lamellar vesicles (MLV) may be prepared by conventional techniques, for example, by depositing a selected lipid on the inside wall of a suitable container or vessel by dissolving the lipid in an appropriate solvent, and then evaporating the solvent to leave a thin film on the inside of the vessel or by spray drying. An aqueous phase may then added to the vessel with a vortexing motion which results in the formation of MLVs. Uni-lamellar vesicles (ULV) can then be formed by homogenization, sonication or extrusion of the multi-lamellar vesicles. In addition, unilamellar vesicles can be formed by detergent removal techniques.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or the entire group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, (e.g., in Markush group or similar format) it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. The publications and other reference materials referenced herein to describe the background of the invention and to provide additional detail regarding its practice are hereby incorporated by reference.

EXAMPLES

Example 1—Preparation of HGT4001

The compound 5-(((10,13-dimethyl-17-(6-methylheptan-2-yl)-2,3,4,7,8,9,10,11,12,13,14,15,16,17-tetradecahydro-1H-cyclopenta[a]phenanthren-3-yl)disulfanyl)methyl)-1H-imidazole (Imidazole-Cholesterol Disulfide) (referred to herein as "HGT4001") was prepared in accordance with the general synthetic scheme shown below is shown in Reaction 1.

Reaction 1

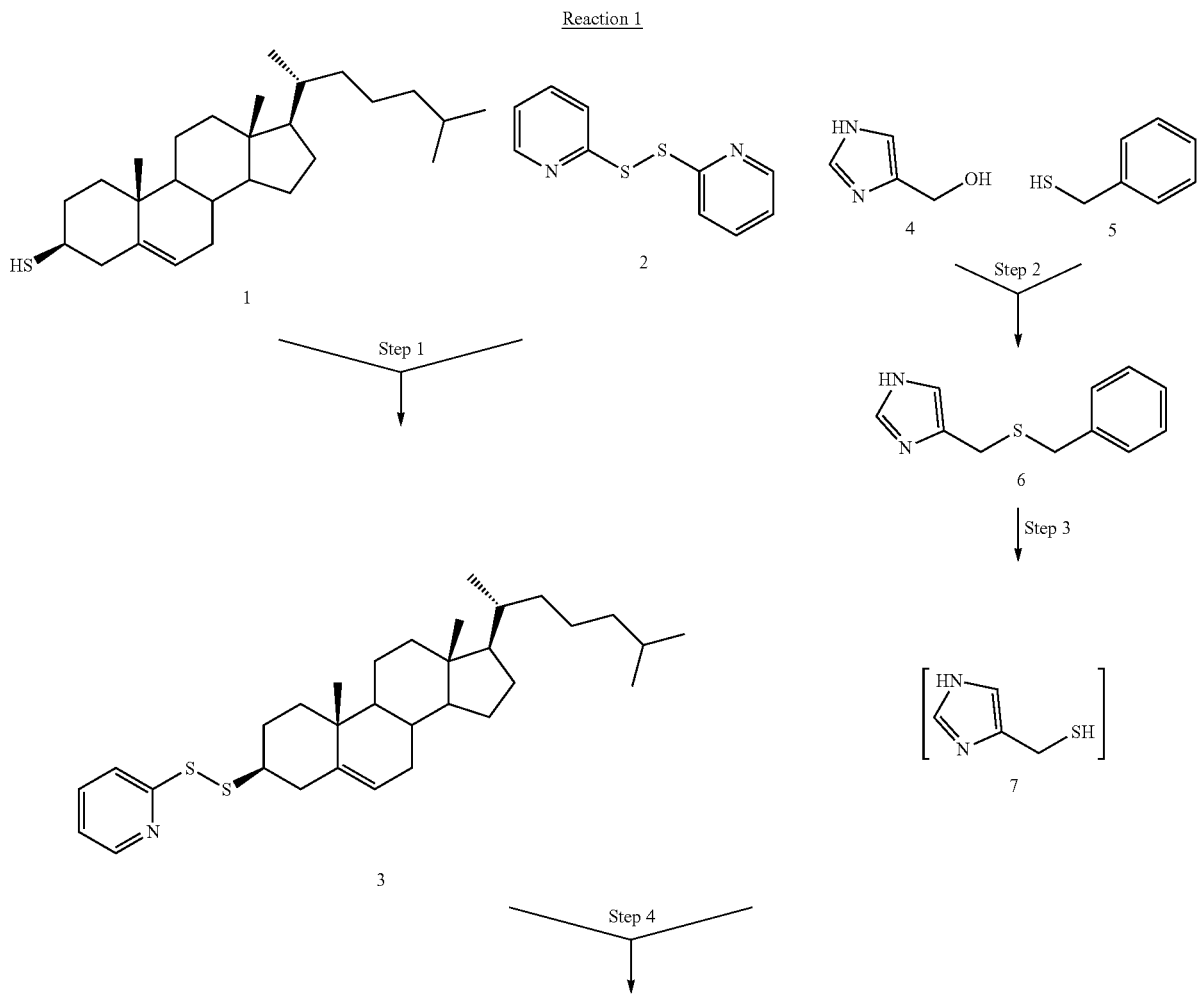

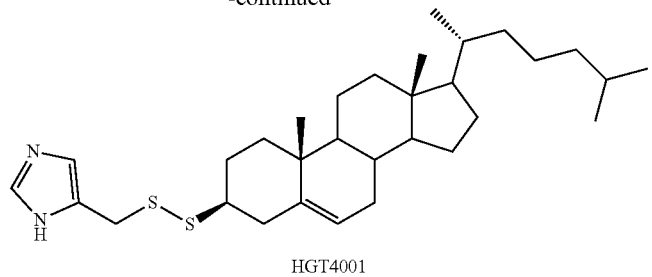

HGT4001

The intermediate compound 2-(((3S,10R,13R,17R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yl)disulfanyl)pyridine (pyridyl cholesterol disulfide) identified as compound (3) was prepared as follows. A solution was prepared comprising 3.0 g (7.45 mmols) of compound (1) and 1.8 g (8.17 mmols) of compound (2) in chloroform (35 ml) and stirred at room temperature for four days. The solvent was evaporated, methanol (50 ml) was added to the residue, and was evaporated. The resulting solid was suspended in methanol (50 ml) and was stirred at room temperature overnight. The pyridyl cholesterol disulfide product (3) was collected by filtration, was washed with methanol, and dried under high vacuum. Yield: 3.6 g (95%). $^1$H NMR (300 MHz, CDCl$_3$) δ 8.43 (m, 1H), 7.76 (m, 1H), 7.62 (m, 1H), 7.05 (m, 1H), 5.32 (bd, J=4 Hz, 1H), 2.75 (m, 1H), 2.35 (d, J=8 Hz, 2H), 2.05-1.7 (m, 5H), 1.7-1.2 (m, 8H), 1.2-0.8 (m, 25H), 0.65 (s, 3H). MS (APCI, Pos): 512 (M+1).

The intermediate compound 4-((benzylthio)methyl)-1H-imidazole identified as compound (6) in Reaction 1 was prepared as follows. A solution was prepared comprising 12.15 g (123.9 mmols) of compound (4) and 15.5 ml (132 mmols) of (5) in glacial acetic acid (200 ml) and was heated to reflux temperature for 24 hours. The reaction mixture was allowed to cool overnight. The solvent was evaporated and the residue was dissolved in chloroform (800 ml). The resulting solution was washed with diluted ammonia (4:1 water:conc. ammonia, 200 ml) and brine (200 ml). The organic phase was dried (Na$_2$SO$_4$), filtered, and the solvent was evaporated. Flash chromatography (silica gel, 500 g; 5-7% methanol in chloroform) provided 23 g of the desired product 4-((benzylthio)methyl)-1H-imidazole (Compound (6)), representing a 91% yield. NMR showed the presence of a small impurity (4% by weight) which was identified as an acetate and is identified as compound (8) below. The compound 6 material was used to produce HGT4001 without further purification. $^1$H NMR (300 MHz, CDCl$_3$) δ 7.60 (d, J=1 Hz, 1H), 7.35-7.2 (m, 5H), 6.90 (d, J=1 Hz, 1H), 3.67 (s, 2H), 3.62 (s, 2H). MS (APCI, Pos): 205 (M+1).

The intermediate compound (1H-imidazol-4-yl)methanethiol identified as compound (7) in Scheme 1 was prepared as follows. A solution of liquid ammonia (200 ml) was condensed over a suspension comprising 15 g of compound (6) (70.5 mmols) in ether (30 ml). To this resulting yellow solution was added 5 g of sodium (217 mmols) in small portions until the mixture remained dark blue. It was then stirred for 40 minutes. Approximately 10-15 g of solid NH$_4$Cl was added until the color disappeared and the solvent was evaporated using a current of nitrogen to provide crude compound (7), which was used without purification.

HGT4001 was prepared by adding 3.6 g of compound (3) (7 mmols) and 10 ml of triethylamine (71.8 mmols) to chloroform (200 ml), and the resulting solution was degassed using vacuum and nitrogen and quickly added to compound (7) and the resulting mixture was stirred at room temperature under nitrogen. After 3 days 200 ml of water was added and the mixture was extracted with chloroform (2×500 ml). The organic extracts were washed with brine (200 ml), dried (Na$_2$SO$_4$), filtered, and solvent was evaporated. Flash chromatography (silica gel, 200 g, neutralized using 1% triethylamine in chloroform; 2-5% ethanol in chloroform) provided 1.25 g of HGT4001 (35% yield for two steps). $^1$H NMR (300 MHz, CDCl$_3$) δ 7.61 (s, 1H), 7.00 (s, 1H), 5.33 (d, 1H), 3.93 (s, 2H), 2.58-2.46 (m, 1H), 2.29 (d, 2H), 1.91 (m, 5H), 1.61-0.84 (m, 33H), 0.66 (s, 3H). $^{13}$C NMR (300 MHz, CDCl$_3$) δ 141.6, 135.3, 134.3, 121.4, 118.1, 56.8, 56.2, 50.3, 50.2, 42.4, 39.8, 39.6, 39.1, 36.8, 36.2, 35.8, 31.9, 29.1, 28.3, 28.1, 24.4, 23.9, 22.9, 22.6, 21.0, 19.4, 18.8, 11.9. MS (APCI, Pos) 515 (M+1). Elem. Anal. C$_{31}$H$_{50}$N$_2$S$_2$, C (72.32 calcd.), found 72.04; H (9.79 calcd.), found 9.84; N (5.44, calcd.), found 5.41.

Example 2—Preparation of HGT4002

The compound 1-(2-(((3S,10R,13R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yl)disulfanyl)ethyl)guanidine (referred to herein as "HGT4002") was prepared in accordance with the general synthetic scheme shown below is shown in Reaction 2.

Reaction 2

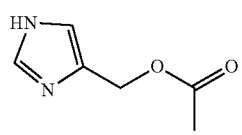

8

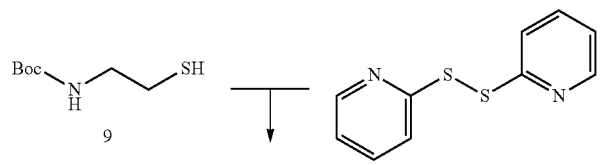

2

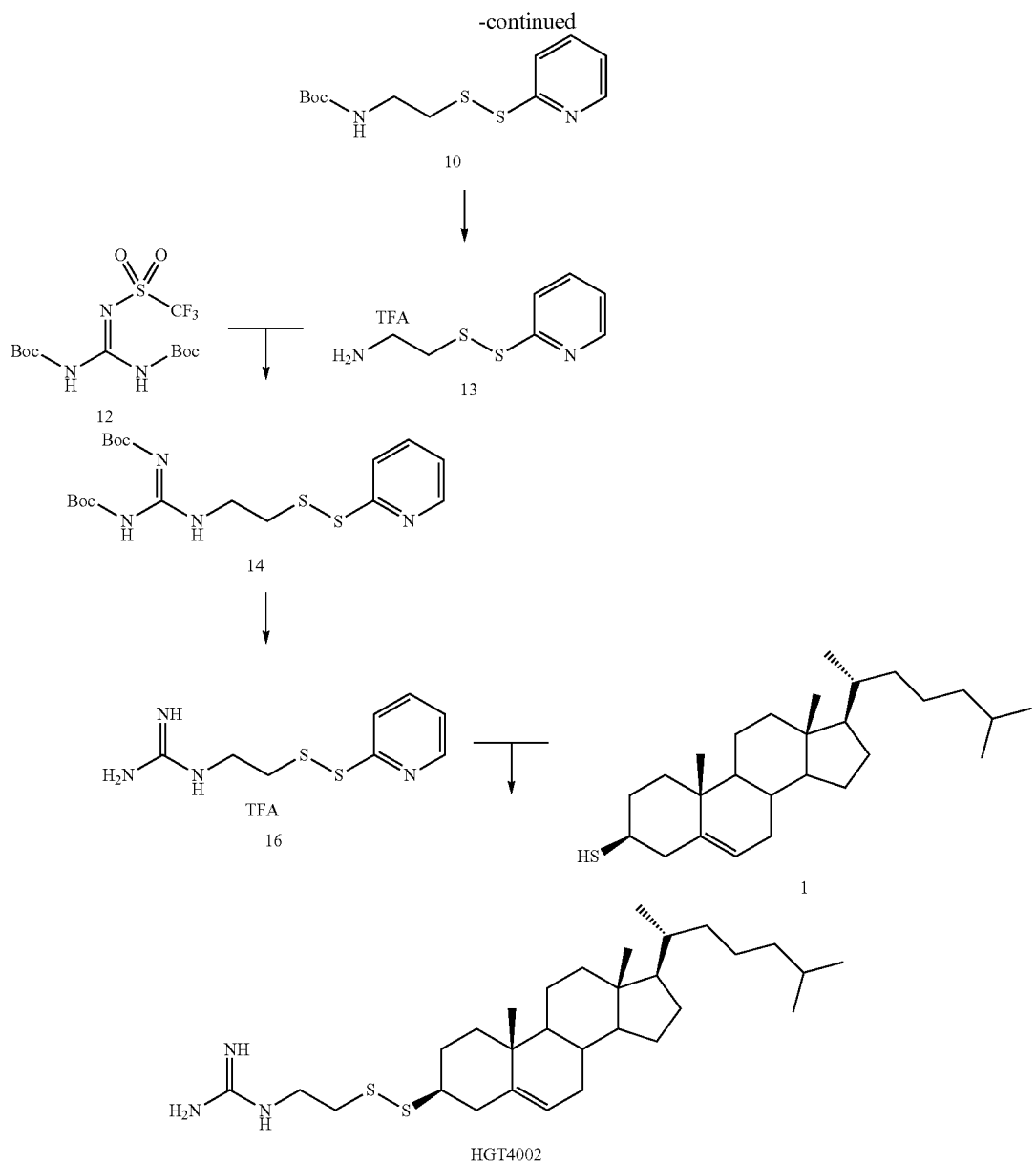

The intermediate compound tert-Butyl (2-(pyridin-2-yldisulfanyl)ethyl)carbamate identified as compound (10) in Reaction 2 above was prepared by adding 5.0 g of compound (9) (28.2 mmols) and 6.82 g of compound (2) (31 mmols) to 100 ml chloroform (100 ml) and stirring at room temperature for four days to form a solution. The solvent was evaporated and the resulting yellow solid was purified by flash chromatography (SiO$_2$, 50-100% ethyl acetate in hexanes) to provide 9.0 g of impure compound (10). NMR showed the presence of the desired material (56% by weight), together with starting material compound (2) (24%) and a disulfide compound (11) (20%) identified below. The mixture obtained was used on the following step without further purification. $^1$H NMR (300 MHz, DMSO-d$_6$) δ 8.55-8.45 (m, 1H), 7.9-7.8 (m, 2H), 7.3-7.2 (m, 1H), 7.07 (bt, J=5 Hz, 1H), 3.25-3.15 (m, 2H), 2.87 (t, J=7 Hz, 2H), 1.37 (s, 9H). MS (APCI, Pos) 287 (M+1), 231 (M+1-C$_4$H$_8$).

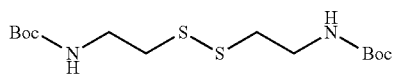

The intermediate compound Bis N,N'-tert butyl-1-(2-(pyridin-2-yldisulfanyl)ethyl)guanidine carbamate (14) was prepared by adding 2.0 g of compound (10) (56% pure, 3.9 mmols) to anhydrous dichloromethane (12 ml) to which was then added TFA (6 ml), and the resulting solution stirred at room temperature for 5 hours. The solvent was evaporated and the residue was dried under high vacuum to provide crude compound (13) (TFA salt). The compound (13) salt was dissolved in 25 ml of anhydrous dichloromethane, excess triethylamine (7 ml) was added followed by the addition of 2.7 g of compound (12) (7.0 mmol) and the reaction mixture was stirred at room temperature overnight, followed by dilution with chloroform (175 ml) and washing with water (2×50 ml) and brine (50 ml). The organic solution was dried (Na₂SO₄), filtered, and the solvent was evaporated. The residue was purified by flash chromatography (SiO₂, 0-10% methanol in chloroform) to provide 1.9 g of impure compound (14). NMR showed the presence of the desired compound (14) (73% by weight), together with disulfide compound (15) (27% by weight) identified below. The mixture was used for the following step without further purification. ¹H NMR (300 MHz, CDCl₃) δ 11.48 (bs, 1H), 8.86 (bt, 1H), 8.55-8.5 (m, 1H), 7.65-7.6 (m, 2H), 7.25-7.15 (m, 1H), 3.8-3.65 (m, 2H), 2.99 (t, J=6 Hz, 2H), 1.51 (s, 9H), 1.49 (s, 9H). MS (APCI, Pos): complex, no (M+1) detected.

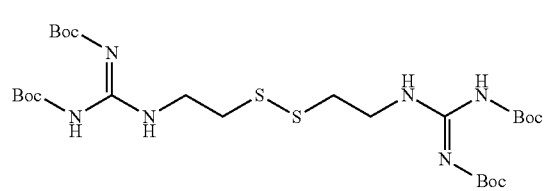

15

The intermediate compound 1-(2-(pyridin-2-yldisulfanyl) ethyl)guanidine trifluoroacetic acid salt, identified as compound (16) in Reaction 2 above was prepared by adding 1.6 g of compound (14) (73% pure, 2.8 mmols) to anhydrous dichloromethane (33 ml), to which was added TFA (11 ml) and the resulting solution stirred at room temperature overnight. The solvent was evaporated and the residue was dried under high vacuum to provide crude compound (16) (TFA salt), which was subsequently used in the following step without purification.

HGT4002 was prepared by dissolving the TFA salt of compound (16) in anhydrous dichloromethane (50 ml), followed by the addition of excess triethylamine (5 ml). 1.13 g of thiocholesterol (1) (2.8 mmol) was added and the reaction mixture was stirred at room temperature overnight, followed by dilution with chloroform (200 ml) and washing with water (2×50 ml) and brine (100 ml). The resulting organic solution was dried (Na₂SO₄), filtered, and the solvent was evaporated. The residue was purified by flash chromatography (SiO₂, 0-30% ethanol in chloroform) and trituration in acetone to provide 80 mg of HGT4002. ¹H NMR (300 MHz, DMSO-d₆) δ 7.60-6.90 (broad s, 4H), 5.35 (d, 1H), 3.39 (t, 2H), 2.84 (t, 2H), 2.72 (m, 1H), 2.28 (m, 2H), 1.91 (m, 5H), 1.58-1.28 (m, 10H), 1.20-0.82 (m, 23H), 0.65 (s, 3H). ¹³C NMR (300 MHz, DMSO-d₆) δ 157.5, 141.5, 121.5, 56.7, 56.1, 50.1, 49.6, 42.4, 38.3, 36.7, 36.2, 35.7, 31.9, 29.0, 28.3, 27.9, 24.4, 23.7, 23.2, 22.9, 21.0, 19.5, 19.1, 12.2. MS (APCI, Pos): 520 (M+1). Elem. Anal. C₃₀H₅₃N₃S₂—SiO₂, C (62.13 calcd.), found 62.33; H (9.21 calcd.), found 9.08; N (7.25, calcd.), found 7.07; S (11.06, calcd.), found 10.83.

Example 3—Preparation of HGT4003

The compound 2-((2,3-Bis((9Z,12Z)-octadeca-9,12-dien-1-yloxy)propyl)disulfanyl)-N,N-dimethylethanamine (referred to herein as "HGT4003") was prepared in accordance with the general synthetic scheme shown below is shown in Reaction 3.

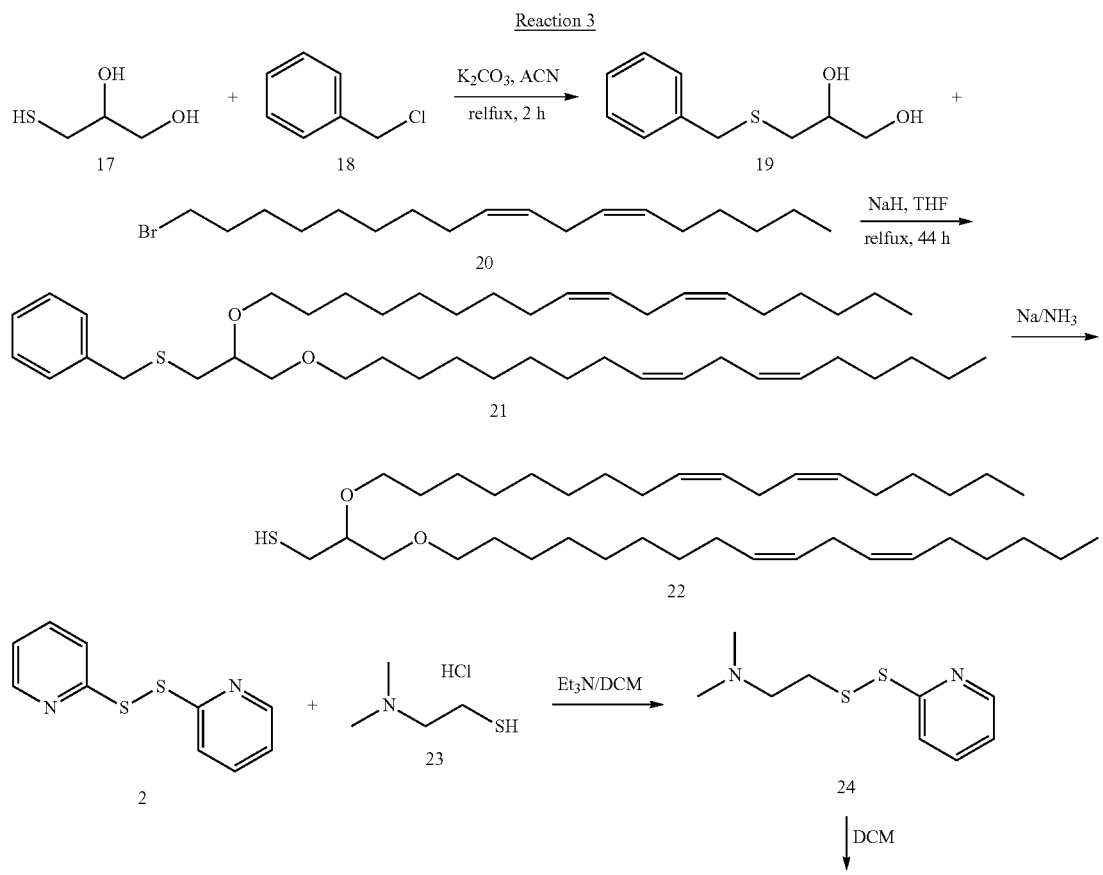

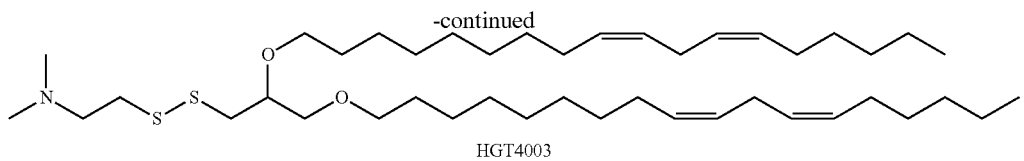

HGT4003

Intermediate compound 3-(Benzylthio)propane-1,2-diol, identified as compound (19) in Reaction 3 above was prepared by adding dropwise 11.37 g of compound (18) (90.3 mmol) to a stirred mixture of 9.73 g of compound (17) (90.3 mmol) and 18.64 g of $K_2CO_3$ (135.1 mmol) in 60 mL of ACN. The resulting mixture was heated at reflux for 2 hours and after cooling the reaction mixture to room temperature the reaction mixture was filtered and the solid rinsed with 20 mL ACN. The filtrate was evaporated and the pale liquid residue was purified by column chromatography (eluent: 10-100% EtOAc in hexanes) to give 17.03 g of compound (19) as a clear liquid (95%).

Intermediate compound Benzyl(2,3-bis((9Z,12Z)-octadeca-9,12-dien-1-yloxy)propyl)sulfane, identified as compound (21) in Reaction 3 above was prepared by adding NaH (60% in mineral oil, 0.82 g, 20.5 mmol) to a stirred mixture of 1.56 g of compound (19) (7.88 mmol) and 6.91 g of compound (20) (21.00 mmol) in THF (200 mL) under $N_2$. The resulting mixture was heated at reflux for 44 hours. After cooling to room temperature the reaction mixture was diluted with $Et_2O$ (400 mL) and washed with water (300 mL) and brine (300 mL). The organic layer was dried over anhydrous $Na_2SO_4$ and evaporated, and the yellow liquid residue was purified by column chromatography (eluent: 0-20% EtOAc in hexanes) to give compound (21) as a light yellow liquid (2.04 g, 37.3%).

Intermediate compound 2,3-Bis((9Z,12Z)-octadeca-9,12-dien-1-yloxy)propane-1-thiol, identified as compound (22) in Reaction 3 above was prepared by adding an $Et_2O$ (30 mL) solution of compound (21) (0.7 g, 1.01 mmol) to liquid $NH_3$ (30 mL) and condensed in a 2-neck RBF at −78° C. under $N_2$, followed by the addition of small pieces of Na (90 mg, 3.91 mmol). The resulting mixture was stirred at −78° C. for 30 min when TLC indicated complete disappearance of compound (21) and 340 mg of $NH_4Cl$ (6.34 mmol) was added. The deep blue color of the reaction mixture faded into a light yellow color within 10 min and the dry-ice acetone bath was removed. The reaction mixture was purged with $N_2$ while gradually warming up to room temperature. After most of $NH_3$ had been blown away by $N_2$ (the volume of the reaction mixture was reduced to about 20 mL) aqueous HCl (3N, 30 mL) was added. This mixture was extracted with DCM (60 mL). The DCM extract was dried over anhydrous $Na_2SO_4$ and evaporated. The yellow liquid residue was purified by column chromatography (eluent: 0-20% EtOAc in hexanes) to give 490 mg of compound (22) as a light yellow liquid (80%).

Intermediate compound N,N-dimethyl-2-(pyridin-2-yldisulfanyl)ethanamine, identified as compound (24) in Reaction 3 above, 2.8 g of compound (2) (12.7 mmol) and 1.41 g of compound (23) (10 mmol) were mixed in DCM (30 mL). The mixture was stirred while it was purged by $N_2$ for 10 minutes and 1.5 mL of $Et_3N$ (11.2 mmol) was added. The resulting solution was stirred at room temperature for 16 hours and applied onto a 230 g silica gel column. The column was eluted with 40-100% EtOAc/hexanes, followed by 8-10% MeOH/DCM to give 0.72 g of compound (24) as a yellow liquid (34%).

The HGT4003 was prepared by combining 487 mg of compound (22) (0.81 mmol) and 180 mg of compound (24) (0.84 mmol) in 2 mL DCM, followed by stirring at room temperature under $N_2$ for 16 hours. The reaction solution was purified by column chromatography three times (eluent: 20-100% EtOAc in hexanes) to give 252 mg of HGT4003 as a light yellow liquid (44%). Also obtained from column chromatography purifications was 213 mg of compound (25) (37%), identified in Reaction 4 below. $^1$H NMR (300 MHz, $CDCl_3$) δ 5.36-5.33 (m, 8H), 3.65 (m, 1H), 3.56-3.50 (m, 4H), 3.43 (td, 2H), 2.96-2.74 (m, 8H), 2.60 (t, 2H), 2.25 (s, 6H), 2.04 (m, 8H), 1.62-1.50 (m, 5H), 1.39-1.22 (m, 32H), 0.88 (t, 6H). $^{13}$C NMR (300 MHz, $CDCl_3$) δ 130.3, 128.0, 71.8, 71.6, 70.6, 58.8, 45.5, 41.4, 36.9, 31.6, 30.1, 29.7, 29.5, 29.4, 27.3, 26.2, 25.7, 22.6, 14.2. MS (APCI, Pos): 709 (M+1). Elem. Anal. $C_{43}H_{81}NO_2S_2$, C (72.92 calcd.), found 72.75; H (11.53 calcd.), found 11.50; N (1.98, calcd.), found 2.08; S (9.05, calcd.), found 8.95.

Reaction 4

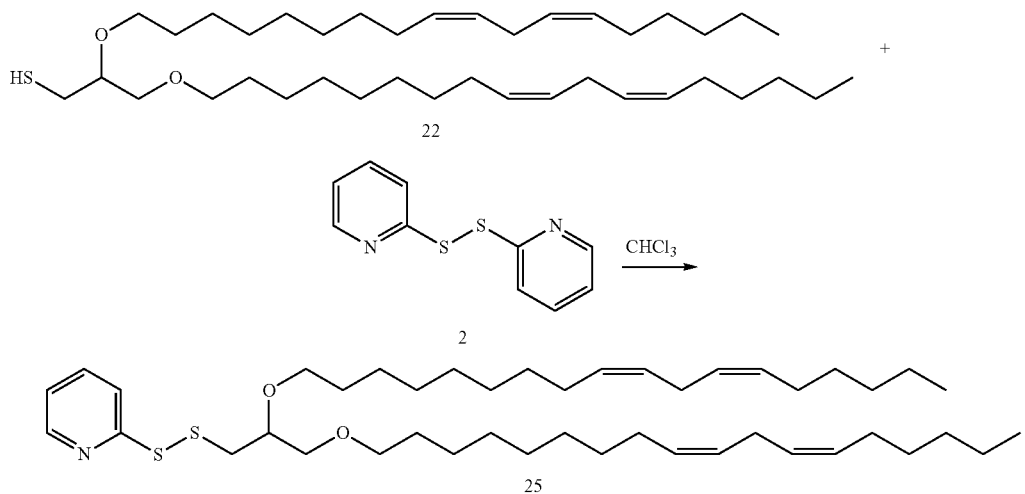

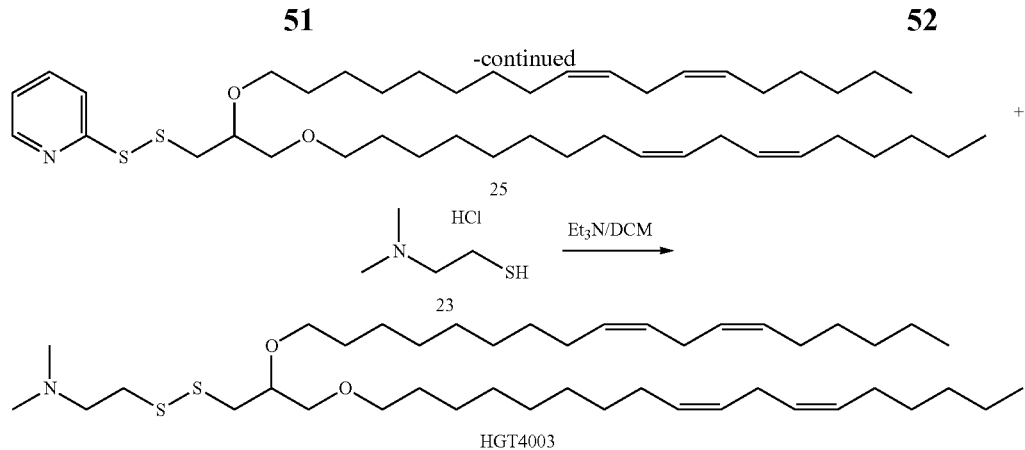

HGT4003

An alternate route to the synthesis of HGT4003 is depicted in Reaction 4 above, employing a pyridyl disulfide bis(alkyl) intermediate. The intermediate compound 2-((2,3-bis((9Z,12Z)-octadeca-9,12-dien-1-yloxy)propyl)disulfanyl)pyridine, identified as compound (25) in Reaction 4 above was prepared by combining 1.35 g of compound (22) (2.24 mmol) and 0.54 g of compound (2) (2.45 mmol) in 10 mL CHCl$_3$ and stirred at room temperature under N$_2$ for 16 hours. The reaction solution was purified by column chromatography three times (eluent: 0-20% EtOAc in hexanes) to give 1.1 g of compound (25) as a light yellow liquid (67%). 1.09 g of compound (23) (7.71 mmol) was then added to the CHCl$_3$ (20 mL) solution of compound (25) (1.1 g, 1.54 mmol) and Et$_3$N (2.6 mL, 18.5 mmol) and stirred under N$_2$. TLC after 16 hours indicated complete disappearance of compound (25). The reaction solution was washed with aqueous NaOH (1N, 20 mL), dried over anhydrous Na$_2$SO$_4$ and evaporated. The yellow liquid residue was purified by column chromatography (eluent: 5-100% EtOAc in hexanes) to give 0.37 g of HGT4003 as a light yellow liquid (34%).

Example 4

Lipid nanoparticles comprising HGT4001, DOPE and DMG-PEG2000 and encapsulating codon-optimized firefly luciferase (FFL) mRNA (SEQ ID NO: 1) were formed via standard ethanol injection methods. (Ponsa, et al., *Int. J. Pharm.* (1993) 95: 51-56.) Ethanolic stock solutions of the lipids were prepared ahead of time at a concentration of 50 mg/mL and stored at −20° C.

Codon-optimized firefly luciferase (FFL) mRNA was synthesized by in vitro transcription from a plasmid DNA template encoding the gene, which was followed by the addition of a 5' cap structure (Cap1) (Fechter, P. et al., *J. Gen. Virology* (2005) 86: 1239-1249) and a 3' poly(A) tail of approximately 200 nucleotides in length as determined by gel electrophoresis. The 5' and 3' untranslated regions present in each FFL mRNA product are represented as X and Y, respectively in SEQ ID NO: 4, as indicated below.

```
Codon optimized firefly luciferase mRNA
(SEQ ID NO: 3):
XAUGGAAGAUGCCAAAAACAUUAAGAAGGGCCCAGCGCCAUUCUACCCAC

UCGAAGACGGGACCGCCGGCGAGCAGCUGCACAAAGCCAUGAAGCGCUAC

GCCCUGGUGCCCGGCACCAUCGCCUUUACCGACGCACAUAUCGAGGUGGA

CAUUACCUACGCCGAGUACUUCGAGAUGAGCGUUCGGCUGGCAGAAGCUA

UGAAGCGCUAUGGGCUGAAUACAAACCAUCGGAUCGUGGUGUGCAGCGAG

AAUAGCUUGCAGUUCUUCAUGCCCGUGUUGGGUGCCCUGUUCAUCGGUGU

GGCUGUGGCCCCAGCUAACGACAUCUACAACGAGCGCGAGCUGCUGAACA

GCAUGGGCAUCAGCCAGCCCACCGUCGUAUUCGUGAGCAAGAAAGGGCUG

CAAAAGAUCCUCAACGUGCAAAAGAAGCUACCGAUCAUACAAAAGAUCAU

CAUCAUGGAUAGCAAGACCGACUACCAGGGCUUCCAAAGCAUGUACACCU

UCGUGACUUCCCAUUUGCCACCCGGCUUCAACGAGUACGACUUCGUGCCC

GAGAGCUUCGACCGGGACAAAACCAUCGCCCUGAUCAUGAACAGUAGUGG

CAGUACCGGAUUGCCCAAGGGCGUAGCCCUACCGCACCGCACCGCUUGUG

UCCGAUUCAGUCAUGCCCGCGACCCCAUCUUCGGCAACCAGAUCAUCCCC

GACACCGCUAUCCUCAGCGUGGUGCCAUUUCACCACGGCUUCGGCAUGUU

CACCACGCUGGGCUACUUGAUCUGCGGCUUUCGGGUCGUGCUCAUGUACC

GCUUCGAGGAGGAGCUAUUCUUGCGCAGCUUGCAAGACUAUAAGAUUCAA

UCUGCCCUGCUGGUGCCCACACUAUUUAGCUUCUUCGCUAAGAGCACUCU

CAUCGACAAGUACGACCUAAGCAACCUGCACGAGAUCGCCAGCGGCGGGG

CGCCGCUCAGCAAGGAGGUAGGUGAGGCCGUGGCCAAACGCUUCCACCUA

CCAGGCAUCCGCCAGGGCUACGGCCUGACAGAAACAACCAGCGCCAUUCU

GAUCACCCCCGAAGGGGACGACAAGCCUGGCGCAGUAGGCAAGGUGGUGC

CCUUCUUCGAGGCUAAGGUGGUGGACUUGGACACCGGUAAGACACUGGGU

GUGAACCAGCGCGGCGAGCUGUGCGUCCGUGGCCCCAUGAUCAUGAGCGG

CUACGUUAACAACCCCGAGGCUACAAACGCUCUCAUCGACAAGGACGGCU

GGCUGCACAGCGGCGACAUCGCCUACUGGGACGAGGACGAGCACUUCUUC

AUCGUGGACCGGCUGAAGAGCCUGAUCAAAUACAAGGGCUACCAGGUAGC

CCCAGCCGAACUGGAGAGCAUCCUGCUGCAACACCCCAACAUCUUCGACG

CCGGGGUCGCCGGCCUGCCCGACGACGAUGCCGGCGAGCUGCCCGCCGCA

GUCGUCGUGCUGGAACACGGUAAAACCAUGACCGAGAAGGAGAUCGUGGA

CUAUGUGGCCAGCCAGGUUACAACCGCCAAGAAGCUGCGCGGUGGUGUUG

UGUUCGUGGACGAGGUGCCUAAAGGACUGACCGGCAAGUUGGACGCCCGC
```

-continued

AAGAUCCGCGAGAUUCUCAUUAAGGCCAAGAAGGGCGGCAAGAUCGCCGU

GUAAY

X =

(SEQ ID NO: 5)

GGGAUCCUACC

Y =

(SEQ ID NO: 6)

UUUGAAUU

The FFL mRNA was stored in water at a final concentration of 1 mg/mL at −80° C. until the time of use. All mRNA concentrations were determined via the Ribogreen assay (Invitrogen). Encapsulation of mRNA was calculated by performing the Ribogreen assay with and without the presence of 0.1% Triton-X 100. Particle sizes (dynamic light scattering (DLS)) and zeta potentials were determined using a Malvern Zetasizer instrument in 1×PBS and 1 mM KCl solutions, respectively.

Aliquots of 50 mg/mL ethanolic solutions of the imidazole-based cationic lipid HGT4001, DOPE and DMG-PEG2000 were mixed and diluted with ethanol to 3 mL final volume. Separately, an aqueous buffered solution (10 mM citrate/150 mM NaCl, pH 4.5) of FFL mRNA was prepared from a 1 mg/mL stock. The lipid solution was injected rapidly into the aqueous mRNA solution and shaken to yield a final suspension in 20% ethanol. The resulting nanoparticle suspension was filtered, diafiltrated with 1×PBS (pH 7.4), concentrated and stored at 2-8° C. Final concentration=0.69 mg/mL CO-FF mRNA (encapsulated). $Z_{ave}$=70.3 nm ($Dv_{(50)}$=43.2 nm; $Dv_{(90)}$=80.3 nm).

Example 5

The present example illustrates that HGT4003-based lipid nanoparticles provide highly efficacious means of delivering polynucleotide constructs to one or more target cells, tissues and organs. The HGT4003-based lipid nanoparticles were formed via standard ethanol injection methods. (Ponsa, et al., *Int. J. Pharm.* (1993) 95: 51-56.) Ethanolic stock solutions of the lipids were prepared ahead of time at a concentration of 50 mg/mL and stored at −20° C.

Codon-optimized firefly luciferase (FFL) mRNA was synthesized by in vitro transcription from a plasmid DNA template encoding the gene, which was followed by the addition of a 5' cap structure (Cap1) (Fechter, P. et al., *J. Gen. Virology* (2005) 86: 1239-1249) and a 3' poly(A) tail of approximately 200 nucleotides in length as determined by gel electrophoresis. The 5' and 3' untranslated regions present in each mRNA product are represented as X and Y, respectively in SEQ ID NO: 4. The FFL mRNA was stored in water at a final concentration of 1 mg/mL at −80° C. until the time of use. All mRNA concentrations were determined via the Ribogreen assay (Invitrogen). Encapsulation of mRNA was calculated by performing the Ribogreen assay with and without the presence of 0.1% Triton-X 100. Particle sizes (dynamic light scattering (DLS)) and zeta potentials were determined using a Malvern Zetasizer instrument in 1×PBS and 1 mM KCl solutions, respectively.

Aliquots of 50 mg/mL ethanolic solutions of HGT4003, DOPE, cholesterol and DMG-PEG2000 were mixed and diluted with ethanol to 3 mL final volume. Separately, an aqueous buffered solution (10 mM citrate/150 mM NaCl, pH 4.5) of FFL mRNA was prepared from a 1 mg/mL stock. The lipid solution was injected rapidly into the aqueous mRNA solution and shaken to yield a final suspension in 20% ethanol. The resulting nanoparticle suspension was filtered, diafiltrated with 1×PBS (pH 7.4), concentrated and stored at 2-8° C. Final concentration=1.27 mg/mL CO-FF mRNA (encapsulated). $Z_{ave}$=60.9 nm ($Dv_{(50)}$=47.9 nm; $Dv_{(90)}$=75.3 nm).

To determine whether the HGT4003-based lipid nanoparticles were capable of delivering encapsulated polynucleotide constructs to one or more target cells, CD-1 mice were injected with a single dose of the HGT4003-based, FFL mRNA-encapsulating lipid nanoparticle and sacrificed after four hours. As discussed below, single doses of the HGT4003-based, FFL mRNA-encapsulating lipid nanoparticle were administered to the animals via one of the intravenous (IV), intracerebroventricular (ICV) or intrathecal (IT) routes of administration. The activity of firefly luciferase protein produced in the livers, spleens, brains and spinal cords of the animals following expression of the FFL mRNA were determined in a bioluminescence assay.

Briefly, the bioluminescence assay was conducted using a Promega Luciferase Assay System (Item #E1500/E4500 Promega). Tissue preparation was performed as follows: Portions of the desired tissue sample (snap-frozen) were thawed, washed with RO/DI water and placed in a ceramic bead homogenization tube. The tissue was treated with lysis buffer and homogenized. Upon subjection to five freeze/thaw cycles followed by centrifugation at 4° C., the supernatant was transferred to new microcentrifuge tubes. Repeat and store tissue extracts at −80° C.

The Luciferase Assay Reagent was prepared by adding 10 mL of Luciferase Assay Buffer to Luciferase Assay Substrate and mix via vortex. 20 μL of homogenate samples was loaded onto a 96-well plate followed by 20 μL of plate control to each sample. Separately, 120 μL of Luciferase Assay Reagent was loaded onto each well of a 96-well flat bottomed plate and each plate inserted into the appropriate chambers using a Biotek Synergy 2 instrument and luminescence measured in relative light units (RLU).

The HGT4003-based, FFL mRNA-encapsulating lipid nanoparticle formulations described herein were evaluated by administering a single bolus intravenous (IV) injection to the animals studied. After four hours, the animals were sacrificed and the liver and spleen were harvested from each animal. Luminescence via FFL protein produced from the delivered exogenous FFL message was detected and analyzed. FIG. 1 illustrates an example using an HGT4003-based lipid nanoparticle system administered intravenously, and demonstrates an enrichment of over an order of magnitude of FFL protein produced in the liver when compared to the spleen (2.34×10⁶ RLU/mg protein versus 1.71×10⁵ RLU/mg protein, respectively), illustrating that the use of the HGT4003-based nanoparticles affords an enrichment of encapsulated materials in the liver over the spleen.

Figure 2:
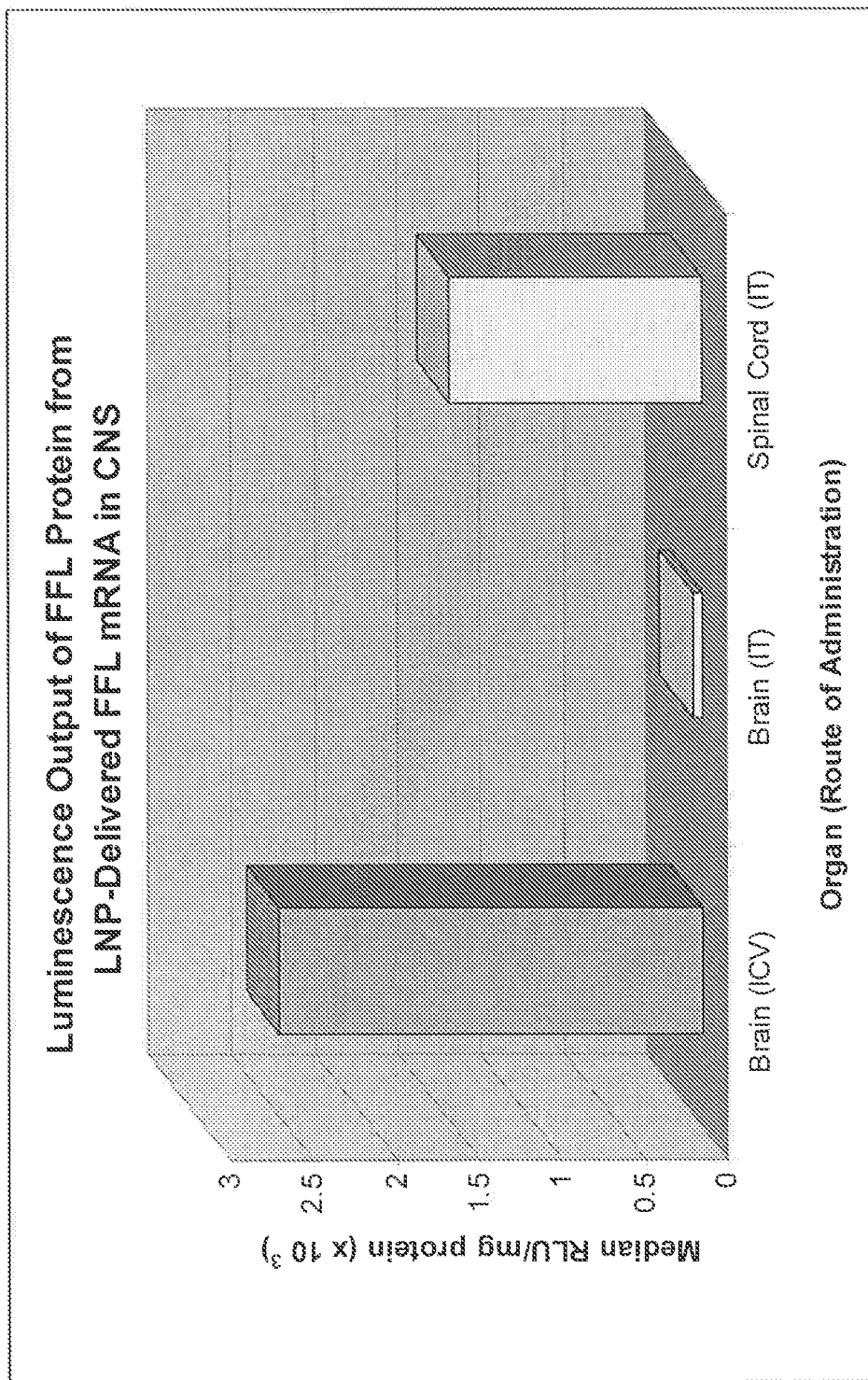
FIG. 2 illustrates the luminescence output of firefly luciferase protein in the brain and spinal cord tissues of mice following intracerebrovascular (ICV) and intrathecal (IT) administration of an HGT4003-based, firefly luciferase (FFL) mRNA-loaded lipid nanoparticles. The administered HGT4003-based lipid nanoparticles afford an enrichment of encapsulated mRNA in the brain using the ICV route of administration as compared to the IT route of administration. Values are depicted as median relative light units (RLU)/mg of total protein four hours post-administration

In addition, HGT4003-based, FFL mRNA-encapsulating lipid nanoparticle formulations were evaluated by administering a single bolus injection to the central nervous system, either by the intracereboventricular (ICV) or intrathecal (IT) route of administration to the animals studies. After four hours, the animals were sacrificed and the brain and spinal cord were harvested from each animal. Luminescence via FFL protein produced from the delivered exogenous FFL message was detected and analyzed. As illustrated in FIG. 2, following administration of the HGT4003-based lipid nanoparticles FFL, protein production was enriched in the brain following the ICV route of administration as compared to the IT route of administration.

A detectable luminescent signal over baseline was observed in every animal administered the HGT4003-based, FFL-mRNA encapsulated lipid nanoparticle formulations, irrespective of the selected route of administration. The presence of a luminescent signal over background infers the expression of the exogenously-administered FFL mRNA and the production of the firefly luciferase protein from such FFL mRNA. The luminescence observed in the liver of the animals was enhanced over similar signals observed in the spleen, suggesting an enrichment of the lipid nanoparticles in the cells and tissues of the liver. Similarly, when the HGT4003-based, FFL mRNA-encapsulated nanoparticles were administered via the ICV route of administration, FFL protein production was enriched in the brain following relative to the IT route of administration. Accordingly, the present example illustrates that HGT4003-based lipid nanoparticles provide highly efficacious means of delivering polynucleotide constructs to one or more target cells, tissues and organs.

Example 6—Lyophilized Liposomal Formulations

Lipid nanoparticles were formed via standard ethanol injection methods (Ponsa, et al., Int. J. Pharm. (1993) 95: 51-56.) Ethanolic stock solutions of the lipids were prepared ahead of time at a concentration of 50 mg/mL and stored at −20° C. Codon-optimized firefly luciferase (FFL) mRNA (SEQ ID NO: 3) was stored in water at a final concentration of 1 mg/mL at −80° C. until the time of use.

All FFL mRNA concentrations were determined via the Ribogreen assay (Invitrogen). Encapsulation of mRNA was calculated by performing the Ribogreen assay with and without the presence of 0.1% Triton-X 100. Particle sizes (dynamic light scattering (DLS)) and particle sizes were determined using a Malvern Zetasizer instrument in 1×PBS and 1 mM KCl solutions, respectively. The in vitro activity of encapsulated mRNA formulations was assessed using 293T cells, and 10 µg of mRNA equivalent of the selected formulation was incubated with the 293T cells for 8 hours at 37° C. The luciferase production was measured using the Perkin Elmer BriteLite Plus kit.

Generally, the lyophilization of the lipid nanoparticles were carried out by freezing the prepared liposomes in a solution comprising a lyoprotectant (sucrose) and subsequently removing any water or moisture by sublimation under vacuum. In particular, prior to lyophilization the buffer present in the liposomal formulation was replaced with 10% sucrose via centrifugation. The resulting lipid nanoparticle solutions were then subjected to a lyophilization process characterized by specific parameters for the freezing, primary drying and secondary drying steps, as identified in Table 1 below. The lyophilized cake was reconstituted with appropriate amount of purified water prior to being subjected to the physical characterization and biochemical analyses described below.

TABLE 1

| Phase | Temperature (° C.) | Vacuum (mTorr) | Time | Ramp/Hold |
|---|---|---|---|---|
| Freezing | 5 | 500 | 6 hours | H |
|  | −45 | 500 |  | R |
|  | −45 | 500 |  | H |
| Primary Drying | −45 | 100 | 60 hours | H |
|  | −35 | 100 |  | R |
|  | −35 | 100 |  | H |
|  | −30 | 100 |  | R |

TABLE 1-continued

| Phase | Temperature (° C.) | Vacuum (mTorr) | Time | Ramp/Hold |
|---|---|---|---|---|
|  | −30 | 100 |  | H |
|  | −20 | 100 |  | R |
|  | −20 | 100 |  | H |
|  | 0 | 100 |  | R |
|  | 0 | 100 |  | H |
| Secondary Drying | 25 | 100 | 6 hours | R |
|  | 25 | 100 |  | H |

Example 7

A formulation of a lipid nanoparticle was prepared comprising firefly luciferase mRNA (FFL) encapsulated in a C12-200:DOPE:CHOL:DMG-PEG2000 (40:30:20:10, N/P 2) lipid nanoparticle. A portion of the batch of the prepared lipid nanoparticle formulation was then lyophilized in accordance with the protocol set forth in Table 1.

The observed physical properties of the fresh (unlyophilized) and lyophilized lipid nanoparticle formulations were compared in accordance with the protocols described above and were found to be consistent. As illustrated in Table 2 below, the average particle size ($Z_{ave}$) for the fresh and lyophilized lipid nanoparticles were 103.8 nm and 117.0 nm, respectively. The polydipersity index (PDI) for the fresh lipid nanoparticles was 0.236 compared to 0.247 for the lyophilized lipid nanoparticles. The $Dv_{50}$ and $Dv_{90}$ for the fresh lipid nanoparticles were 60.2 nm and 156 nm, respectively compared to a $Dv_{50}$ and $Dv_{90}$ of 49.0 nm and 176 nm for the lyophilized lipid nanoparticles, respectively. Accordingly, the observed physical characteristics also suggest that both the fresh and lyophilized lipid nanoparticles were stable and furthermore that the particle sizes remained relatively comparable.

TABLE 2

| Batch 5926-48 | $Z_{ave}$ (nm) | PDI | $Dv_{50}$ (nm) | $Dv_{90}$ (nm) |
|---|---|---|---|---|
| Prior to Lyophilization | 103.8 | 0.236 | 60.2 | 156 |
| Post Lyophilization | 117.0 | 0.247 | 49.0 | 176 |

Example 8

A formulation of a lipid nanoparticle was prepared comprising firefly luciferase mRNA (FFL) encapsulated in a DLinKC2-DMA:DOPE:CHOL:DMG-PEG2000 (50:25:20:5, N/P 5) lipid nanoparticle. One batch of the prepared lipid nanoparticle formulation was lyophilized in accordance with the protocol set forth in Table 5 below.

The lyophilization processes was carried out by freezing the prepared liposomes in a solution comprising a lyoprotectant (sucrose) and subsequently removing any water or moisture by sublimation under vacuum. In particular, prior to lyophilization, the buffer in the liposomal formulations was replaced with 10% sucrose via centrifugation. The resulting liposomal solutions were then subjected to a lyophilization process characterized by specific parameters for the freezing, primary drying and secondary drying steps identified in Table 3 below. The lyophilized cake was reconstituted with an appropriate amount of purified water prior to the physical characterizations and biochemical analyses described below.

TABLE 3

| Phase | Temperature (° C.) | Vacuum (mTorr) | Time | Ramp/Hold |
|---|---|---|---|---|
| Freezing | 5 | 500 | 11 hours | H |
|  | −45 | 500 |  | R |
|  | −45 | 500 |  | H |
| Primary Drying | −45 | 100 | 61 hours | H |
|  | −35 | 100 |  | R |
|  | −35 | 100 |  | H |
|  | −30 | 100 |  | R |
|  | −30 | 100 |  | H |
|  | −20 | 100 |  | R |
|  | −20 | 100 |  | H |
|  | 0 | 100 |  | R |
|  | 0 | 100 |  | H |
| Secondary Drying | 25 | 100 | 8 hours | R |
|  | 25 | 100 |  | H |

The prepared fresh (unlyophilized) and lyophilized formulations were used to deliver the encapsulated FFL mRNA to 293T cells, and luminescence was determined in accordance with the protocol described above. As illustrated in Table 4 below, the luminescence value of $4.21 \times 10^6$ was observed for the fresh lipid nanoparticles before lyophilization compared to $2.65 \times 10^6$ observed following reconstitution of the lyophilized formulation.

The average particle size ($Z_{ave}$) for the fresh and lyophilized lipid nanoparticles were 89.11 nm and 96.41 nm, respectively. The polydipersity index (PDI) for the fresh lipid nanoparticles was 0.205 compared to 0.204 for the lyophilized lipid nanoparticles. The $Dv_{50}$ and $Dv_{90}$ for the fresh lipid nanoparticles were 63.8 nm and 117 nm, respectively, compared to a $Dv_{50}$ and $Dv_{90}$ of 65.1 nm and 135 nm for the lyophilized lipid nanoparticles, respectively. As demonstrated in Table 6, both particle size and encapsulation efficiency were well maintained during lyophilization. The encapsulation efficiency of FFL mRNA was 93% and 87% for the fresh and lyophilized lipid nanoparticles, respectively. Additionally, the observed physical characteristics suggest that both the fresh and lyophilized lipid nanoparticles were stable and furthermore that the particle sizes remained relatively comparable.

TABLE 4

| Batch 6087-100-2 | $Z_{ave}$ (nm) | PDI | $Dv_{50}$ (nm) | $Dv_{90}$ (nm) | Encapsulation (%) | Luminesence in 293T cells |
|---|---|---|---|---|---|---|
| FF Luciferase nanoparticles before Lyophilization | 89.11 | 0.205 | 63.8 | 117 | 93 | $4.21 \times 10^6$ |
| Resuspension post-Lyophilization | 96.41 | 0.204 | 65.1 | 135 | 87 | $2.65 \times 10^6$ |

Example 9

A formulation of a lipid nanoparticle was prepared comprising erythropoietin (EPO) mRNA (SEQ ID NO:4), flanked by SEQ ID NO:1 and SEQ ID NO:2 at the 5' and 3' ends respectively and encapsulated in a DLinKC2-DMA:DOPE:CHOL:DMG-PEG2000 (50:25:20:5, N/P 5) lipid nanoparticle. One batch of the prepared lipid nanoparticle formulation was lyophilized in accordance with the protocol set forth in Table 3.

Human Erythropoietin (EPO) mRNA
(SEQ ID NO: 4)
AUGGGGGUGCACGAAUGUCCUGCCUGGCUGUGGCUUCUCCUGUCCCUGC

UGUCGCUCCCUCUGGGCCUCCCAGUCCUGGGCGCCCCACCACGCCUCAU

CUGUGACAGCCGAGUCCUGGAGAGGUACCUCUUGGAGGCCAAGGAGGCC

GAGAAUAUCACGACGGGCUGUGCUGAACACUGCAGCUUGAAUGAGAAUA

UCACUGUCCCAGACACCARAGUUAAUUUCUAUGCCUGGAAGAGGAUGGA

GGUCGGGCAGCAGGCCGUAGAAGUCUGGCAGGGCCUGGCCCUGCUGUCG

GAAGCUGUCCUGCGGGGCCAGGCCCUGUUGGUCAACUCUUCCCAGCCGU

GGGAGCCCCUGCAGCUGCAUGUGGAUAAAGCCGUCAGUGGCCUUCGCAG

CCUCACCACUCUGCUUCGGGCUCUGGGGAGCCCAGAAGGAAGCCAUCUCC

CCUCCAGAUGCGGCCUCAGCUGCUCCACUCCGAACAAUCACUGCUGACA

CUUUCCGCAAACUCUUCCGAGUCUACUCCAAUUUCCUCCGGGGAAAGCU

GAAGCUGUACACAGGGGAGGCCUGCAGGACAGGGGACAGAUGA

The observed physical properties of the lipid nanoparticle formulation both before and after lyophilization were compared in accordance with the protocols described above and were found to be consistent. As illustrated in Table 5 below, the average particle size ($Z_{ave}$) for the fresh (unlyophilized) and lyophilized lipid nanoparticles were 85.9 nm and 95.4 nm, respectively, suggesting that both the fresh and lyophilized lipid nanoparticles were stable. The polydipersity index (PDI) for the fresh lipid nanoparticles was 0.188 compared to 0.231 for the lyophilized lipid 112 nm, respectively compared to a $Dv_{50}$ and $Dv_{90}$ of 67.2 nm and 134 nm for the lyophilized lipid nanoparticles, respectively. The encapsulation efficiency of EPO mRNA was 94% and 86% for the fresh and lyophilized lipid nanoparticles, respectively. As also demonstrated in Table 7, both particle size and encapsulation efficiency were well maintained during lyophilization.

Finally, erythropoietin protein produced by the 293T cells was measured using R&D Systems Human EPO Quantikine IVD ELISA Kit. As depicted in Table 5 the erythropoietin protein produced following delivery of the EPO mRNA to the 293T cells for both the pre- and post-lyophilization formulations was comparable, and there was no significant difference in erythropoietin protein production when comparing the lipid nanoparticle formulations both before and after lyophilization.

TABLE 5

| Batch 6087-100-4 | $Z_{ave}$ (nm) | PDI | $Dv_{50}$ (nm) | $Dv_{90}$ (nm) | Encapsulation (%) | EPO (mIU/mL) |
|---|---|---|---|---|---|---|
| EPO nanoparticles before Lyophilization | 85.9 | 0.188 | 61.0 | 112 | 94 | 373.1 |
| Resuspension post-Lyophilization | 95.4 | 0.231 | 67.2 | 134 | 86 | 387.9 |

Example 10

A six-month stability study was conducted on lypholized EPO mRNA encapsulated lipid nanoparticles. The particle size distribution, mRNA encapsulation efficiency as well as expression of EPO in CD-1 mice were determined.

The lipid formulation comprised EPO mRNA encapsulated in KC2:DOPE:CHOL:DMGPEG2K (50:25:20:5) as described in Example 9. The N/P ratio (defined as the ratio of the number of nitrogen in cationic lipid to the number of phosphate in nucleic acid) was 5.

One vial was stored at 2-8 degree C. One vial was stored at room temperature. The humidity was not controlled for both storage conditions.

The lyophilized cake was reconstituted with appropriate amount of water for injection prior to physical characterization and animal studies.

The particle size was obtained with Malvern Zetasizer Nano-ZS. The encapsulation efficiency of mRNA in lipid particles was determined using Invitrogen RiboGreen assay kit. The unencapsulated mRNA was detected directly. The total mRNA was measured after lysis of lipid nanoparticles in the presence 0.45% w/v of Triton X-100. The encapsulation efficiency was calculated as (Total mRNA−unencapsulated mRNA)/Total mRNA×100%.

Wild type CD-1 mice were used to evaluate the relative expression of EPO following a single IV administration of two formulations of hEPO mRNA encapsulated lipid nanoparticles. Levels of EPO in serum were measured at 6 hours post-dose administration. Four CD-1 mice (2 male, 2 female), 7 weeks of age, were used for this study. Upon arrival, animals were randomized into 2 treatment groups containing 2 animals per group (1 male, 1 female per group). On Day 1, animals were weighed and body weights were recorded. Each mouse received a single IV dose of 99 µg mRNA/animal in a dose volume of 300 µL/animal. At 6 hours post-dose administration, the mice were euthanized by $CO_2$ asphyxiation followed by thoracotomy and maximum obtainable volumes of blood were collected and processed for serum. All treatments administered were well tolerated in the CD-1 mouse following a single IV administration. Serum levels of hEPO were measured by ELISA. EPO was observed in serum from all of the study animals that received either of the formulation.

Test results are summarized in Table 6. No significant change in particle size distribution was observed after storage of lyophilized lipid nanoparticles for 6 months at both refrigeration and room temperatures. In addition, the encapsulation efficiency of mRNA in lipid nanoparticles essentially remained unchanged during storage. These results suggest that the integrality of lipid particle was well maintained during storage at lyophilized configuration. The 6-month stability under accelerated condition of room temperature supports a potential 2-year shelf life under refrigeration condition. Furthermore, the serum hEPO was detected in wild type CD-1 mice at 6 h following intravenous injection of reconstituted suspension of lyophilized lipid nanoparticles after storage at either refrigeration or room temperature. These results demonstrate that the integrality of lipid particle was effectively protected during storage at lyophilized configuration.

TABLE 6

| Batch 6087-100-4 | Zave (nm) | PDI | Dv50 (nm) | Dv90 (nm) | Encap-sulation (%) | Serum hEPO at 6 h (mIU/mL) |
|---|---|---|---|---|---|---|
| EPO nanoparticles before lyophilization | 85.9 | 0.188 | 61.0 | 112 | 94 | Not determined |
| Resuspension of lyophilized nanoparticles which were stored at 2-8° C. for 6 months | 90.04 | 0.165 | 61.1 | 119 | 95 | Male 5,077 Female 95,937 |
| Resuspension of lyophilized nanoparticles which were stored at RT for 6 months | 92.06 | 0.156 | 67.0 | 124 | 94 | Male 25,015 Female 61,855 |

Abbreviations:
1) Zave (Zaverage) is the mean value from intensity distribution;
2) PDI (polydispersity index) describes the distribution width;
3) Dv50 is the median for a volume distribution;
4) Dv90 means 90 percent of the volume distribution lies below this value.

Example 11

Lyophilization studies on mRNA encapsulated lipid nanoparticles using 2-hydroxypropyl-beta-cyclodextrin as lyoprotectant were conducted. For comparison, sucrose lyoprotectant, was also evaluated.

The mRNA was encapsulated into C12-200:DOPE:CHOL:DMGPEG2K (40:30:25:5) lipid particles by ethanol dilution method. The N/P ratio was 20. The buffer in formulations was replaced with aqueous solution containing appropriate amount of sucrose or 2-hydroxypropyl-beta-cyclodextrin via centrifugation prior to lyophilization. The resulting solutions were subjected to a lyophilization process characterized by specific parameters for the freezing, primary drying and secondary drying steps. Table 7 describes a lyophilization cycle for sucrose containing formulations. Table 8 describes a lyophilization cycle for 2-hydroxypropyl-beta-cyclodextrin containing formulations. The lyophilized cake was reconstituted with appropriate amount of purified water prior to physical characterization and biochemical analysis. The particle size was obtained with Malvern Zetasizer Nano-ZS. The encapsulation efficiency of mRNA in lipid particles was determined using The total mRNA was measured after lysis of lipid nanoparticles in the presence 0.45% w/v of Triton X-100. The encapsulation efficiency was calculated as (Total mRNA−unencapsulated mRNA)/Total mRNA×100%.

Wild type CD-1 mice were used to evaluate the relative expression of EPO in mice following a single IV administration of two formulations of EPO mRNA encapsulated lipid nanoparticles. Levels of EPO in serum were measured at 6 h post-dose administration. Three male CD-1 mice, 7 weeks of age, were used in each group. Upon arrival, animals were randomized into treatment groups containing 3 animals per group. On Day 1, animals were weighed and body weights were recorded. Each mouse received a single IV dose of 15 µg mRNA/animal in a dose volume of 50 µL/animal. At 6 h post-dose administration, the mice were euthanized by CO2 asphyxiation followed by thoracotomy and maximum obtainable volumes of blood were collected and processed for serum. All treatments administered were well tolerated in the CD-1 mouse following a single IV administration. Serum levels of EPO were measured by ELISA. EPO was observed in serum from all of the study animals that received either of the formulation.

TABLE 7

| Phase | Temperature (° C.) | Vacuum (mTorr) | Time | Ramp/Hold |
|---|---|---|---|---|
| Freezing | 5 | 500 | 8 hours | H |
|  | −45 | 500 |  | R |
|  | −45 | 500 |  | H |
| Primary Drying | −45 | 100 | 69 hours | H |
|  | −35 | 100 |  | R |
|  | −35 | 100 |  | H |
|  | −30 | 100 |  | R |
|  | −30 | 100 |  | H |
|  | −20 | 100 |  | R |
|  | −20 | 100 |  | H |
|  | 0 | 100 |  | R |
|  | 0 | 100 |  | H |
|  | 25 | 100 |  | R |
|  | 25 | 100 |  | H |
| Secondary Drying | 0 | 100 | 4 hours |  |

TABLE 8

| Phase | Temperature (° C.) | Vacuum (mTorr) | Time | Ramp/Hold |
|---|---|---|---|---|
| Freezing | 5 | 500 | 7 hours | H |
|  | −45 | 500 |  | R |
|  | −45 | 500 |  | H |
| Primary Drying | −45 | 100 | 69 hours | H |
|  | −20 | 100 |  | R |
|  | −20 | 100 |  | H |
|  | −10 | 100 |  | R |
|  | −10 | 100 |  | H |
|  | 0 | 100 |  | R |
|  | 0 | 100 |  | H |
|  | 10 | 100 |  | R |
|  | 10 | 100 |  | H |
|  | 20 | 100 |  | R |
|  | 20 | 100 |  | H |
| Secondary Drying | 0 | 100 | 4 hours |  |

All testing results are summarized in Table 9. Particle size growth was observed during lyophilization when sucrose was used as lyoprotect at 6:1 weight ratio to total lipids. However, particle size was well maintained when 2-hydroxypropyl-beta-cyclodextrin was used instead even at relatively low weight ratio of 5:1. N/P was 20. In addition, the encapsulation efficiency of mRNA in lipid nanoparticles was well maintained during lyophilization. These results suggest that the integrality of lipid particle was effectively protected during lyophilization. Furthermore, the serum hEPO levels in wild type CD-1 mice at 6 hours post-dose administration are comparable before and after lyophilization. In summary, 2-hydroxypropyl-beta-cyclodextrin is an effective lyoprotectant for mRNA encapsulated lipid nanoparticles formulated with C12-200 lipid.

TABLE 9

| Batch ID | 5926-101 nanoparticles before lyophilization | 5926-101 resuspension post-lyophilization | 5926-154 nanoparticles before lyophilization | 5926-154 resuspension post-lyophilization |
|---|---|---|---|---|
| mRNA (mg/mL) | 0.3 | 0.3 | 0.3 | 0.3 |
| Lyoprotectant | N/A | sucrose | N/A | 2-hydroxy-propyl-beta-cyclodextrin |
| Lyoprotectant/Total Lipids | N/A | 6:1 | N/A | 5:1 |
| Zave (nm) | 74.90 | 112.4 | 99.94 | 104.9 |
| PDI | 0.112 | 0.199 | 0.205 | 0.203 |
| Dv50 (nm) | 58.2 | 80.3 | 71.8 | 73.3 |
| Dv90 (nm) | 96.6 | 181 | 142 | 159 |
| Encapsulation % | 83 | 76 | 83 | 91 |
| Mean Serum EPO at 6 h (mIU/mL) | not determined | not determined | 142,279 ± 55,823 | 218,945 ± 72,294 |

Abbreviations: 1) Zave (Zaverage) is the mean value from intensity distribution; 2) PDI (polydispersity index) describes the distribution width; 3) Dv50 is the median for a volume distribution; 4) Dv90 means 90 percent of the volume distribution lies below this value.

The foregoing examples illustrate that the lyophilized lipid nanoparticle formulations demonstrated comparable or equivalent physical characteristics relative to the unlyophilized lipid nanoparticles that were prepared, including comparable stability, lipid nanoparticle particle sizes and encapsulation efficiencies. With respect to the encapsulated mRNA polynucleotides, the lyophilized lipid nanoparticles also demonstrated a comparable production of protein. For example, several of the lyophilized lipid nanoparticle compositions evaluated demonstrated a comparable production of firefly luciferase protein as determined by the presence of a luminescent signal, and thereby inferring the expression and/or production of the exogenously-administered encapsulated mRNA. The foregoing results suggest that the lyophilized lipid nanoparticle compositions and formulations described herein are stable and capable of minimizing degradation of encapsulated compounds (e.g., polynucleotides). Such lyophilized lipid nanoparticle compositions are expected to have increased shelf-life upon storage under both under refrigerated and ambient temperature storage conditions, thereby presenting attractive means of improving the availability and potential costs associated with such pharmaceutical compositions.

---

What is claimed is:

1. A lyophilized pharmaceutical composition comprising a lipid nanoparticle and a lyoprotectant that is trehalose, wherein the lipid nanoparticle comprises
   ornithine transcarbamylase mRNA,
   a cationic lipid,
   a PEG-modified lipid that is DMG-PEG2000,
   a non-cationic lipid that is 1,2-dioleyl-sn-glycero-3-phosphoethanolamine (DOPE), and
   a helper lipid that is cholesterol.

2. The lyophilized pharmaceutical composition of claim 1, wherein the composition is in a form selected from intravenous, oral, rectal, vaginal, transmucosal, sublingual, subdural, nasal, intramuscular, subcutaneous, intramedullar injection, intrathecal, intraventricular, intraperitoneal, intranasal, ophthalmic, and intraocular.

3. The lyophilized pharmaceutical composition of claim 1, wherein the composition has an encapsulation efficiency greater than about 80%.

* * * * *

SEQUENCE LISTING

```
<160> NUMBER OF SEQ ID NOS: 11

<210> SEQ ID NO 1
<211> LENGTH: 140
<212> TYPE: RNA
<213> ORGANISM: Human cytomegalovirus
<220> FEATURE:
<221> NAME/KEY: misc_feature
<222> LOCATION: (1)..(3)
<223> OTHER INFORMATION: /note="this region may or may not be present"
```

```
<400> SEQUENCE: 1
ggacagaucg ccuggagacg ccauccacgc uguuuugacc uccauagaag acaccgggac      60
cgauccagcc uccgcggccg ggaacggugc auuggaacgc ggauuccccg ugccaagagu     120
gacucaccgu ccuugacacg                                                 140

<210> SEQ ID NO 2
<211> LENGTH: 100
<212> TYPE: RNA
<213> ORGANISM: Homo sapiens

<400> SEQUENCE: 2
cggguggcau cccugugacc ccucccagu gccucuccug gcccuggaag uugccacucc       60
agugcccacc agccuugucc uaauaaaauu aaguugcauc                          100

<210> SEQ ID NO 3
<211> LENGTH: 1672
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: misc_feature
<222> LOCATION: (1)..(11)
<223> OTHER INFORMATION: /note="5' untranslated region"
<220> FEATURE:
<221> NAME/KEY: misc_feature
<222> LOCATION: (1665)..(1672)
<223> OTHER INFORMATION: /note="3' untranslated region"

<400> SEQUENCE: 3
gggauccuac cauggaagau gccaaaaaca uuaagaaggg cccagcgcca uucuacccac      60
ucgaagacgg gaccgccggc gagcagcugc acaaagccau gaagcgcuac gcccugguge    120 ccggcaccau cgccuuuacc gacgcacaua ucgaggugga cauuaccuac gccgaguacu    180
ucgagaugag cguucggcug gcagaagcua ugaagcgcua ugggcugaau acaaaccauc    240
ggaucguggu gugcagcgag aauagcuugc aguucuucau gcccguguug ggugcccugu    300
ucaucggugu ggcuguggcc ccagcuaacg acaucuacaa cgagcgcgag cugcugaaca    360
gcaugggcau cagccagccc accgucuauu ucgugagcaa gaaagggcug caaaagaucc    420
ucaacgugca aaagaagcua ccgaucauac aaaagaucau caucauggau agcaagaccg    480
acuaccaggg cuuccaaagc auguacaccu ucgugacuuc ccauuugcca cccggcuuca    540
acgaguacga cuucgugccc gagagcuucg accgggacaa aaccaucgcc cugaucauga    600
acaguagugg caguaccgga uugcccaagg gcguagcccu accgcaccgc accgcuugug    660
uccgauucag ucaugcccgc gaccccaucu ucggcaacca gaucauccc gacaccgcua    720 uccucagcgu ggugccauuu caccacggcu ucggcauguu caccacgcug gcuacuuga    780 ucugcggcuu ucgggucgug cucauguacc gcuucgagga ggagcuauuc uugcgcagcu    840
ugcaagacua uaagauucaa ucugcccugc uggugcccac acauuuagc uucuucgcua    900 agagcacucu caucgacaag uacgaccuaa gcaacuugca cgagaucgcc agcggcgggg    960
cgccgcucag caaggaggua ggugaggccg uggccaaacg cuuccaccua ccaggcaucc   1020
gccagggcua cggccugaca gaaacaacca cgcgccauucu gaucaccccc gaaggggacg   1080
acaagccugg cgcaguaggc aaggugugc ccucuucga ggcuaaggug guggacuugg    1140
acaccgguaa gacacuggu gugaaccagc gcggcgagcu gugcguccgu ggccccauga    1200
```

| | |
|---|---|
| ucaugagcgg cuacguuaac aaccccgagg cuacaaacgc ucucaucgac aaggacggcu | 1260 |
| ggcugcacag cggcgacauc gccuacuggg acgaggacga gcacuucuuc aucguggacc | 1320 |
| ggcugaagag ccugaucaaa uacaagggcu accagguagc cccagccgaa cuggagagca | 1380 |
| uccugcugca acaccccaac aucuucgacg ccggggucgc cggccugccc gacgacgaug | 1440 |
| ccggcgagcu gcccgccgca gucgucgugc uggaacacgg uaaaaccaug accgagaagg | 1500 |
| agaucgugga cuauguggcc agccagguua caaccgccaa gaagcugcgc gguggcuguug | 1560 |
| uguucgugga cgaggugccu aaaggacuga ccggcaaguu ggacgcccgc aagauccgcg | 1620 |
| agauucucau uaaggccaag aagggcggca agaucgccgu guaauuugaa uu | 1672 |

```
<210> SEQ ID NO 4
<211> LENGTH: 582
<212> TYPE: RNA
<213> ORGANISM: Homo sapiens

<400> SEQUENCE: 4
```

| | |
|---|---|
| auggggugc acgaaugucc ugccuggcug uggcuucucc uguccugcu gucgcucccu | 60 |
| cugggccucc caguccuggg cgccccacca cgccucaucu gugacagccg aguccuggag | 120 |
| agguaccucu uggaggccaa ggaggccgag aauaucacga cgggcugugc ugaacacugc | 180 |
| agcuugaaug agaauaucac ugcccagac accaaaguua auuucuaugc cuggaagagg | 240 |
| auggaggucg gcagcaggc cguagaaguc uggcagggcc uggcccugcu gucggaagcu | 300 |
| guccugcggg gccaggcccu guuggucaac ucuucccagc cgugggagcc ccugcagcug | 360 |
| cauguggaua aagccgucag uggccuucgc agccucacca cucugcuucg ggcucuggga | 420 |
| gcccagaagg aagccaucuc cccuccagau gcggccucag cugcuccacu ccgaacaauc | 480 |
| acugcugaca cuuuccgcaa acucuuccga gucuacucca auuccuccg gggaaagcug | 540 |
| aagcuguaca caggggaggc cugcaggaca ggggacagau ga | 582 |

```
<210> SEQ ID NO 5
<211> LENGTH: 11
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 5
```

| | |
|---|---|
| gggauccuac c | 11 |

```
<210> SEQ ID NO 6
<211> LENGTH: 8
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 6
```

| | |
|---|---|
| uuugaauu | 8 |

```
<210> SEQ ID NO 7
<211> LENGTH: 90
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 7
aaaaaaaaaa aaaaaaaaaa aaaaaaaaaa aaaaaaaaaa aaaaaaaaaa aaaaaaaaaa    60
aaaaaaaaaa aaaaaaaaaa aaaaaaaaaa                                     90

<210> SEQ ID NO 8
<211> LENGTH: 200
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 8
aaaaaaaaaa aaaaaaaaaa aaaaaaaaaa aaaaaaaaaa aaaaaaaaaa aaaaaaaaaa    60
aaaaaaaaaa aaaaaaaaaa aaaaaaaaaa aaaaaaaaaa aaaaaaaaaa aaaaaaaaaa   120
aaaaaaaaaa aaaaaaaaaa aaaaaaaaaa aaaaaaaaaa aaaaaaaaaa aaaaaaaaaa   180
aaaaaaaaaa aaaaaaaaaa                                               200

<210> SEQ ID NO 9
<211> LENGTH: 300
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 9
aaaaaaaaaa aaaaaaaaaa aaaaaaaaaa aaaaaaaaaa aaaaaaaaaa aaaaaaaaaa    60
aaaaaaaaaa aaaaaaaaaa aaaaaaaaaa aaaaaaaaaa aaaaaaaaaa aaaaaaaaaa   120
aaaaaaaaaa aaaaaaaaaa aaaaaaaaaa aaaaaaaaaa aaaaaaaaaa aaaaaaaaaa   180
aaaaaaaaaa aaaaaaaaaa aaaaaaaaaa aaaaaaaaaa aaaaaaaaaa aaaaaaaaaa   240
aaaaaaaaaa aaaaaaaaaa aaaaaaaaaa aaaaaaaaaa aaaaaaaaaa aaaaaaaaaa   300

<210> SEQ ID NO 10
<211> LENGTH: 400
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 10
aaaaaaaaaa aaaaaaaaaa aaaaaaaaaa aaaaaaaaaa aaaaaaaaaa aaaaaaaaaa    60
aaaaaaaaaa aaaaaaaaaa aaaaaaaaaa aaaaaaaaaa aaaaaaaaaa aaaaaaaaaa   120
aaaaaaaaaa aaaaaaaaaa aaaaaaaaaa aaaaaaaaaa aaaaaaaaaa aaaaaaaaaa   180
aaaaaaaaaa aaaaaaaaaa aaaaaaaaaa aaaaaaaaaa aaaaaaaaaa aaaaaaaaaa   240
aaaaaaaaaa aaaaaaaaaa aaaaaaaaaa aaaaaaaaaa aaaaaaaaaa aaaaaaaaaa   300
aaaaaaaaaa aaaaaaaaaa aaaaaaaaaa aaaaaaaaaa aaaaaaaaaa aaaaaaaaaa   360
aaaaaaaaaa aaaaaaaaaa aaaaaaaaaa aaaaaaaaaa                         400
```

```
<210> SEQ ID NO 11
<211> LENGTH: 500
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 11
aaaaaaaaaa aaaaaaaaaa aaaaaaaaaa aaaaaaaaaa aaaaaaaaaa aaaaaaaaaa      60
aaaaaaaaaa aaaaaaaaaa aaaaaaaaaa aaaaaaaaaa aaaaaaaaaa aaaaaaaaaa     120
aaaaaaaaaa aaaaaaaaaa aaaaaaaaaa aaaaaaaaaa aaaaaaaaaa aaaaaaaaaa     180
aaaaaaaaaa aaaaaaaaaa aaaaaaaaaa aaaaaaaaaa aaaaaaaaaa aaaaaaaaaa     240
aaaaaaaaaa aaaaaaaaaa aaaaaaaaaa aaaaaaaaaa aaaaaaaaaa aaaaaaaaaa     300
aaaaaaaaaa aaaaaaaaaa aaaaaaaaaa aaaaaaaaaa aaaaaaaaaa aaaaaaaaaa     360
aaaaaaaaaa aaaaaaaaaa aaaaaaaaaa aaaaaaaaaa aaaaaaaaaa aaaaaaaaaa     420
aaaaaaaaaa aaaaaaaaaa aaaaaaaaaa aaaaaaaaaa aaaaaaaaaa aaaaaaaaaa     480
aaaaaaaaaa aaaaaaaaaa                                                 500
```